(12) United States Patent
Foulon et al.

(10) Patent No.: US 8,362,067 B2
(45) Date of Patent: Jan. 29, 2013

(54) 3-AMINOALKYL-1,3-DIHYDRO-2H-INDOL-2-ONE DERIVATIVES, PREPARATION THEREOF AND THERAPEUTIC USE THEREOF

(75) Inventors: Loïc Foulon, Paris (FR); Laurent Goullieux, Paris (FR); Brigitte Pouzet, Paris (FR); Claudine Serradeil-Le Gal, Paris (FR); Gerard Valette, Paris (FR)

(73) Assignee: Sanofi, Paris (FR)

( * ) Notice: Subject to any disclaimer, the term of this patent is extended or adjusted under 35 U.S.C. 154(b) by 246 days.

(21) Appl. No.: 12/858,976

(22) Filed: Aug. 18, 2010

(65) Prior Publication Data

US 2011/0059955 A1    Mar. 10, 2011

Related U.S. Application Data

(63) Continuation of application No. PCT/FR2009/000179, filed on Feb. 18, 2009.

(30) Foreign Application Priority Data

Feb. 19, 2008 (FR) ...................................... 08 00866

(51) Int. Cl.
  C07D 209/46  (2006.01)
  C07D 403/00  (2006.01)
  A01N 43/38   (2006.01)
  A61K 31/40   (2006.01)

(52) U.S. Cl. .......................... 514/418; 544/359; 548/472
(58) Field of Classification Search .................. 548/472; 544/359; 514/418
  See application file for complete search history.

(56) References Cited

U.S. PATENT DOCUMENTS

| 5,618,833 A | 4/1997 | Foulon et al. |
| 6,864,277 B2 * | 3/2005 | Roux et al. ..................... 514/418 |

FOREIGN PATENT DOCUMENTS

| AU | 684791 | 1/1998 |
| EP | 0061741 A2 | 10/1982 |
| EP | 0469984 B1 | 10/1995 |
| WO | WO 93/15051 | 8/1993 |
| WO | WO 95/18105 | 7/1995 |
| WO | WO 97/15556 | 5/1997 |
| WO | WO 98/25901 | 6/1998 |
| WO | WO 01/55130 | 8/2001 |
| WO | WO 01/55134 | 8/2001 |
| WO | WO 01/64666 | 9/2001 |
| WO | WO 01/98295 | 12/2001 |
| WO | WO 03/008407 | 1/2003 |
| WO | WO 2006/005609 | 1/2006 |
| WO | WO 2006/080574 | 8/2006 |
| WO | WO 2006/100082 | 9/2006 |
| WO | WO 2008/025735 | 3/2008 |
| WO | WO 2009/115685 A1 | 9/2009 |

OTHER PUBLICATIONS

Woll, P. J., et al., Multiple Neuropeptides Mobilise Calcium in Small Cell Lung Cancer: Effects of Vasopressin Bradykinin, Cholecystokinin, Galanin and Neurotensin, Biochemical and Biophysical Research Communications pp. 66-73, vol. 164, No. 1, (1989).
Arsenijevic, Y., et. al., Vasopressin-Binding Sites in the Pig Putuitary Gland: Competition by Novel Vasopressin Antagonists Suggest the Existence of an Unusual Receptor Subtype in the Anterior Lobe, J. Endocrinology, vol. 141, pp. 383-391, (1994).
Bernardini, et. al., In Vivo and in Vitro Effects of Arginine-Vasopressin Receptor Antagonists on the Hypothalamic Pituitary-Adrenal Axis in the Rat, Neuroendocrinology, vol. 60, pp. 503-508, (1994).
Bertherat, J., et. al., Ectopic Expression of the Pituitary V3 Vasopressin Receptor Reveals New Aspects of the Ectopic ACTH Syndrome, Eur. J. Endocrino., (1996), vol. 135, pp. 173-174.
Birnbaumer, M., et. al., Molecular Cloning of the Receptor for Human Antidiuretic Hormone, Nature, vol. 357 pp. 333-335, (1992).
Wittert, G. A., et. al., Arginine Vasopressin in Cushing's Disease, The Lancet, (1990), vol. 335, pp. 991-994. Dickstein, G., et al., Plasma Corticotropin and Cortisol Responses to Ovine Corticotropin-Releasing Hormone (CRH), Arginine Vasopressin (AVP), CRH plus AVP. and CRH plus Metyrapone in Patients with Cushing's Disease, Journal of Clinical Endocrinology and Metabolism, vol. 81, No. 8. pp. 2934-2941, (1996).
Egbertson, M. S., et. al., Non-Peptide Fibrinogen Receptor Antagonists, 2. Optimization of a Tyrosine Template as a Mimic for Arg-Gly-Asp, J. Med. Chem., vol. 37, pp. 2537-2551, (1994).
Elands, J., et. al., 125i-Labelled D(CH2)5[Tyr(Me)2,Thr4,Tyr-NH29]OVT: A Selective Oxytocin Receptor Ligand, European Journal of Pharmacology, vol. 147, pp. 197-207, (1987).

(Continued)

*Primary Examiner* — Sreeni Padmanabhan
*Assistant Examiner* — Kendra D Carter
(74) *Attorney, Agent, or Firm* — Ronald G. Ort

(57) ABSTRACT

The present invention relates to novel 3-aminoalkyl-1,3-dihydro-2H-indol-2-one derivatives, to their preparation and to their therapeutic application.
The compounds of the present invention correspond to the formula (I):

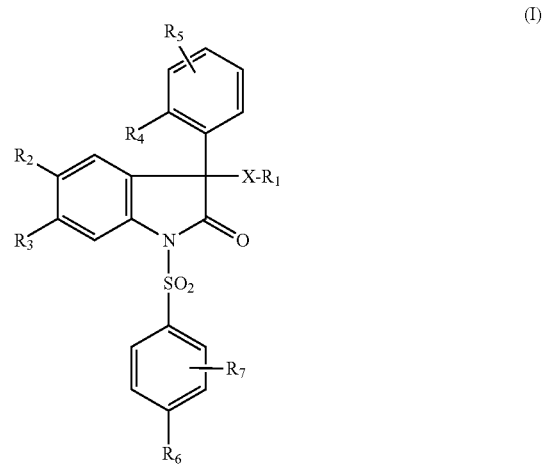

in which the variables are as set forth in the specification.
These compounds exhibit a strong affinity and a high selectivity for human arginine-vasopressin (AVP) $V_{1a}$ receptors and some compounds additionally exhibit a strong affinity for AVP $V_{1b}$ receptors.

8 Claims, No Drawings

OTHER PUBLICATIONS

Gillies, G. E., et. al., Corticotropin Releasing Activity of the New CRF is Potentiated Several Times by Vasopressin, Nature, vol. 299, pp. 355-357, (1982).

Grazzini. E., et. al., Molecular and Functional Characterization of V1b Vasopressin Receptor in Rat Adrenal Medulla, Endocrinology, vol. 137, No. 9, pp. 3906-3914, (1996).

Grazzini, E., et. al., Vasopressin Receptors in Human Adrenal Medulla and Pheochromocytoma, The Journal of Clinical Endocrinology & Metabolism, (1999), vol. 84, pp. 2195-2203.

Guillon, G., et. al., Vasopressin Stimulates Steroid Secretion in Human Adrenal Glands: Comparison with Angiotensin-II Effect, Endocrinology, vol. 136, No. 3, pp. 1285-1295 (1995).

Hulme, C., et. al., Quatemary Substituted PDE4 Inhibitors I: The Snythesis and in Vitro Evaluation of a Novel Series of Oxindoles, Bioorganic & Medicinal Chemistry Letters, vol. 8, (1998), pp. 175-178.

Jard, S., et. al., Vasopressin Antagonist Allow Demonstration of a Novel Type of Vasopressin Receptor in the Rat Adenohypophysis, Molecular Pharmacology, vol. 30, pp. 171-177, (1986).

Jard, S., et. al., Vasopressin and Oxytocin Receptors: An Overview, Progress in Endocrinology, (1988), pp. 1183-118.

Keyzer, Y. D., et. al., Cloning and Characterization of the Human V3 Pituitary Vasopressin Receptor, FEBS Letters, vol. 356, (1994), pp. 215-220.

Laszlo, F. A., et. al., Pharmacology and Clinical Perspectives of Vasopressin Antagonists, Pharmacology Rev., (1991), vol. 43, No. 1, pp. 73-108.

Lee, B., et. al., Effect of AVP and Oxytocin on Insulin Release: Involvement of V1b Receptors, Am. J. Physiol., vol. 269, (Endocrinol. Metab. 32), pp. E1095-E1100, (1995).

Lolait, S. J., et. al., Extrapituitary Expression of the Rat V1b Vasopressin Receptor Gene, Proc. Natl. Aca. Sci USA, Neurobiology, vol. 92, pp. 6783-6787, (1995).

Manning, M., et. al., Discovery, Development, and Some Uses of Vasopressin and Oxytocin Antagonists, J. Lab. Clin. Med., (1989), vol. 114, No. 6, pp. 617-632.

Mazzocchi, G., et. al., Arginine-Vasopressin Stimulates CRH and ACTH Release by Rat Adrenal Medulla, Acting Via the V1 Receptor Subtype and a Protein Kinase C-Dependent Pathway, Peptides, vol. 18, No. 2, pp. 191-195, (1997).

Popp, F. D., et. al., The Chemistry of Isatin, Advances in Heterocyclic Chemistry, vol. 18, pp .1-12, (1975).

Saito, M. et. al., Molecular Cloning and Characterization of Rat V1B Vasopressin Receptor: Evidence for Its Expression in Extra-Pituitary Tissues, Biochemical and Biophysical Research Communications, vol. 212, No. 3, (1995), pp. 751-757.

Sarradeil-Le Gal, C., et. al., Biochemical and Pharmacological Properties of SR 49059, A New, Potent, Nonpeptide Antagonist of Rat and Human Vaspressin V1a Receptors, J. Clin, Invest., (1993), vol. 92, pp. 224-231.

Schwartz, J, et. al., A Potent New Synthetic Analog of Vasopressin With Relative Agonist Specificity for The Pituitary, Endocrinology, vol. 129, No. 2, pp. 1107-1109, (1991).

Sugimoto, T., et. al., Molecular Cloning and Functional Expression of a CDNA Encoding the Human V1b Vasopressin Receptor, The Journal of Biological Chemistry, vol. 269, No. 43, (1994), pp. 27088-27092.

Sullivan, E., et. al., Measurement of [Ca2+] Using the Fluorometric Imaging Plate Reader (FLIPR), Methods in Molecular Biology, vol. 114, pp. 125-133, (1999).

Thibonnier, M., et. al., Molecular Cloning, Sequencing, and Functional Expression of a CDNA Enoding the Human V1a Vasopressin Receptor, The Journal of Biological Chemistry, vol. 269, No. 5, pp. 3304-3310, (1994).

Ventura, M. A., et. al., Gene and cDNA Cloning and Characterization of the Mouse V3/V1b Pituitary Vasopressin Receptor, Journal of Molecular Endocrinology, (1999), vol. 22, pp. 251-260.

\* cited by examiner

3-AMINOALKYL-1,3-DIHYDRO-2H-INDOL-2-ONE DERIVATIVES, PREPARATION THEREOF AND THERAPEUTIC USE THEREOF

FIELD OF THE INVENTION

The present invention relates to novel 3-aminoalkyl-1,3-dihydro-2H-indol-2-one derivatives, to their preparation and to their therapeutic application.

The compounds according to the present invention exhibit a strong affinity and a high selectivity for human arginine-vasopressin (AVP) $V_{1a}$ receptors and some compounds according to the invention additionally exhibit a strong affinity for AVP $V_{1b}$ receptors.

BACKGROUND OF THE INVENTION

AVP is a hormone known for its antidiuretic effect and its effect in regulating arterial pressure. It stimulates several types of receptors: $V_1$ ($V_{1a}$, $V_{1b}$) or $V_2$. These receptors are located in particular in the liver, vessels (coronary, renal, cerebral), platelets, kidney, uterus, adrenal glands, pancreas, central nervous system or pituitary gland. AVP thus exerts cardiovascular, hepatic, pancreatic, antidiuretic and platelet-aggregating effects and effects on the central and peripheral nervous system and on the uterine sphere.

The localization of the various receptors is described in: S. Jard et al., Vasopressin and oxytocin receptors: an overview, in Progress in Endocrinology, H. Imura and K. Shizurne ed., Experta Medica, Amsterdam, 1988, 1183-1188, and in the following articles: J. Lab. Clin. Med., 1989, 114 (6), 617-632 and Pharmacol. Rev., 1991, 43 (1), 73-108.

More particularly, AVP $V_{1a}$ receptors are located in numerous peripheral organs and in the brain. They have been cloned in the rat and man and they regulate the majority of known effects of AVP: platelet aggregation; uterine contractions; vessel contraction; contraction of renal mesangial cells; the secretion of aldosterone, of cortisol, of CRF (corticotropin-releasing factor) and of adrenocorticotrophic hormone (ACTH); hepatic glycogenolysis, cell proliferation and the main central effects of AVP (hypothermia, memory, anxiety, affiliation, and the like).

The adrenal cortex is also rich in $V_{1a}$ receptors involved in the production of gluco- and mineralocorticoids (aldosterone and cortisol). Via these receptors, AVP (circulating or synthesized locally) can bring about production of aldosterone with an effectiveness comparable to that of angiotensin II (G. Guillon et al., Endocrinology, 1995, 136 (3), 1285-1295). Cortisol is a powerful regulator of the production of ACTH, the stress hormone.

Recent studies have also shown that the adrenal glands are capable of directly releasing CRF and/or ACTH via the activation of the $V_{1a}$ and/or $V_{1b}$ receptors carried by the cells of the medulla (G. Mazzocchi et al., Peptides, 1997, 18 (2), 191-195; E. Grazzini et al., J. Clin. Endocrinol. Metab., 1999, 84 (6), 2195-2203).

The $V_{1a}$ receptors are also a more specific label for small cell lung cancers (SCLC) (P. J. Woll et al., Biochem. Biophys. Res. Commun., 1989, 164 (1), 66-73). Thus, the compounds according to the present invention are obvious diagnostic tools and offer a novel therapeutic approach for controlling the proliferation of these tumours and their detection, at an early stage too (radiolabelling; SPECT (Single Photon Emission Computed Tomography); PET scan (Positron Emission Tomography Scan)).

The $V_{1b}$ receptors were initially identified in the adenohypophysis of various animal species (rat, pig, cow, sheep, and the like), including in man (S. Jard et al., Mol. Pharmacol., 1986, 30, 171-177; Y. Arsenijevic et al., J. Endocrinol., 1994, 141, 383-391; J. Schwartz et al., Endocrinology, 1991, 129 (2), 1107-1109; Y. de Keyser et al., FEBS Letters, 1994, 356, 215-220), where they stimulate the release of adrenocorticotrophic hormone by AVP and potentiate the effects of CRF on the release of ACTH (G. E. Gdjjes et al., Nature, 1982, 299, 355). In the hypothalamus, the $V_{1b}$ receptors also induce a direct release of CRF (Neuroendocrinology, 1994, 60, 503-508) and are, in these various respects, implicated in stress situations.

These $V_{1b}$ receptors have been cloned in the rat, man and mouse (Y. de Keyser, FEBS Letters, 1994, 356, 215-220; T. Sugimoto et al., J. Biol. Chem., 1994, 269 (43), 27088-27092; M. Saito et al., Biochem. Biophys. Res. Commun., 1995, 212 (3), 751-757; S. J. Lolait et al., Neurobiology, 1996, 92, 6783-6787; M. A. Ventura et al., Journal of Molecular Endocrinology, 1999, 22, 251-260) and various studies (in situ hybridization, PCR (Polymerase Chain Reaction), and the like) reveal ubiquitous localization of these receptors in various central tissues (brain, hypothalamus and adenohypophysis, in particular) and peripheral tissues (kidney, pancreas, adrenal glands, heart, lungs, intestine, stomach, liver, mesentery, bladder, thymus, spleen, uterus, retina, thyroid, and the like) and in some tumors (hypophyseal or pulmonary tumors, and the like), suggesting a broad biological and/or pathological role of these receptors and potential involvement in various diseases.

By way of examples, in the rat, studies have shown that AVP, via the $V_{1b}$ receptors, regulates the endocrine pancreas, stimulating the secretion of insulin and of glucagon (B. Lee et al., Am. J. Physiol., 269 (Endocrinol. Metab. 32), E1095-E1100, 1995) or the production of catecholamines in the adrenal medulla, which is the site of a local synthesis of AVP (E. Grazzini et al., Endocrinology, 1996, 137 (a), 3906-3914). Thus, in the latter tissue, AVP, via these receptors, would have a crucial role in some types of adrenal pheochromocytomas which secrete AVP and which, for this reason, bring about a sustained production of catecholamines which are the cause of hypertension and which are resistant to angiotensin-II receptor antagonists and to converting enzyme inhibitors. The adrenal cortex is also rich in $V_{1a}$ receptors involved in the production of gluco- and mineralocorticoids (aldosterone and cortisol). Via these receptors, AVP (circulating or synthesized locally) can bring about production of aldosterone with an effectiveness comparable to that of angiotensin II (G. Guillon et al., Endocrinology, 1995, 136 (3), 1285-1295). Cortisol is a powerful regulator of the production of ACTH, the stress hormone.

The $V_{1b}$ receptors are also regarded as a label for ACTH-secreting tumors, which are some pituitary tumors and some bronchial (small cell lung cancers or SCLC), pancreatic, adrenal and thyroid carcinomas, resulting in some cases in Cushing's syndrome (J. Bertherat et al., Eur. J. Endocrinol., 1996, 135, 173; G. A. Wuinert et al., Lancet, 1990, 335, 991-994; G. Dickstein et al., J. Clin. Endocrinol. Metab., 1996, 81 (8), 2934-2941). The $V_{1a}$ receptors are, for their part, a more specific label for small cell lung cancers (SCLC) (P. J. Woll et al., Biochem. Biophys. Res. Commun., 1989, 164 (1), 66-73). Thus, the compounds according to the present invention are obvious diagnostic tools and offer a novel therapeutic approach in the proliferation and detection of these tumors, at an early stage too (radiolabeling; SPECT (Single Photon Emission Computed Tomography); PET Scan (Positron Emission Tomography Scan)).

The lavish presence of the messenger of the $V_{1b}$ receptors in the stomach and intestine suggests involvement of AVP via this receptor in the release of gastrointestinal hormones, such as cholecystokinin, gastrin or secretin (T. Sugimoto et al., Molecular cloning and functional expression of $V_{1b}$ receptor gene, in Neurohypophysis: Recent Progress of Vasopressin and Oxytocin Research; T. Saito, K. Kurokawa and S. Yoshida ed., Elvesier Science, 1995, 409-413).

1,3-Dihydro-2H-indol-2-one derivatives have been disclosed in some patent applications as ligands of the arginine-vasopressin and/or oxytocin receptors: mention may be made of Patent Applications WO 93/15051, EP 636 608, EP 636 609, WO 97/15556, WO 98/25901, WO 01/55130, WO 01/55134, WO 01/64668, WO 01/98295, WO 03/008407, WO 06/080574 and WO 08/025,735.

International application WO 95/18105 relates to compounds of formula:

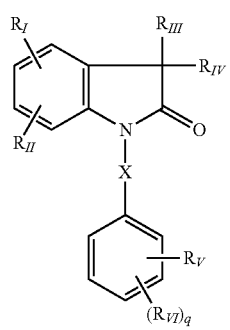

(A)

in which in particular:
X represents $SO_2$;
$R_I$, $R_{II}$, $R_{III}$, $R_{IV}$, $R_V$, $R_{VI}$ and q have different values.

The compounds of formula (A) have an affinity for generally vasopressin and/or oxytocin receptors. In addition, this patent application does not describe any example in which $R_{II}$ is in the 6 position of the phenyl and represents a radical methoxy and $R_{IV}$ is always bonded in the 3 position of the indole-2-one ring via a nitrogen atom.

In particular, 3-[4-[[5,6-dichloro-3-(2-chlorophenyl)-2-oxo-3-[(2-(piperidin-4-yl)ethyl)amino]-2,3-dihydro-1H-indol-1-yl]sulfonyl]phenyl]-1,1-diethylurea (compound α) is described in Example 220 and 3-[4-[[5-chloro-3-(2-chlorophenyl)-6-methyl-2-oxo-3-[(2-(piperidin-4-yl)ethyl)amino]-2,3-dihydro-1H-indol-1-yl]sulfonyl]phenyl]-1,1-diethylurea (compound β) is described in Example 277 of WO 95/018 105.

Compound α exhibits a good affinity for human AVP $V_{1a}$ receptors but also for human AVP $V_2$ receptors and oxytocin receptors; it is therefore not selective for human AVP $V_{1a}$ receptors and for human AVP $V_{1b}$ receptors.

Compound β exhibits a good affinity for human AVP $V_{1a}$ receptors but also for human AVP $V_2$ receptors; it is therefore not selective for human AVP $V_{1a}$ receptors and for human AVP $V_{1b}$ receptors.

DESCRIPTION OF THE INVENTION

Novel compounds have now been found which exhibit a strong affinity and a high selectivity for human AVP $V_{1a}$ receptors and which are antagonists of said receptors and some compounds additionally exhibit a strong affinity for human AVP $V_{1b}$ receptors.

A subject matter of the present invention is compounds corresponding to the formula (I):

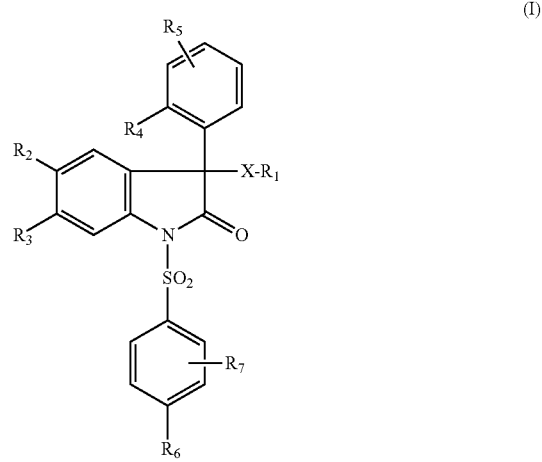

(I)

in which:
X represents a divalent $(C_1-C_5)$alkylene radical which is unsubstituted or substituted one or more times on a carbon atom by a fluorine atom or by a $(C_1-C_3)$alkyl;
$R_1$ represents:
an —$NR_8R_9$ group;
a piperidin-4-yl radical or a piperidin-3-yl radical which is unsubstituted or substituted one or more times by a $(C_1-C_4)$alkyl or a $(C_3-C_5)$cycloalkyl, it being possible for the carbon atoms to be also substituted by one or more fluorine atoms;
$R_2$ represents a halogen atom, an Alk group or an OAlk group;
$R_3$ represents a methoxy;
$R_4$ represents a hydrogen atom, a halogen atom, an Alk group, a hydroxyl or an OAlk group;
$R_5$ represents a hydrogen atom, a halogen atom, an Alk group, a hydroxyl, an OAlk group, a —$CO_2$Alk group or a —$CH_2OH$ radical;
$R_6$ represents a hydrogen atom, an Alk group, a hydroxyl, an OAlk group, a $(C_3-C_5)$cycloalkyloxy or an —$NR_{10}CONR_{11}R_{12}$ group;
$R_7$ represents a hydrogen atom, a halogen atom, an Alk group, a hydroxyl or an OAlk group;
or else $R_7$ is in the 3 position of the phenyl and, together with $R_6$, represents a trimethylene radical;
$R_8$ and $R_9$ each independently represent a hydrogen atom or a $(C_1-C_4)$alkyl;
or else $R_8$ and $R_9$, together with the nitrogen atom to which they are bonded, constitute a saturated or unsaturated 3- to 10-membered heterocyclic radical, said heterocyclic radical being unsubstituted or substituted one or more times by an amino, a dimethylamino, a hydroxyl, an Alk group, a $(C_3-C_5)$cycloalkyl, an OAlk group or an —$SO_2$Alk radical, it being possible for the carbon atoms to be also substituted by one or more fluorine atoms;
$R_{10}$ represents a hydrogen atom or a $(C_1-C_4)$alkyl;
$R_{11}$ and $R_{12}$ each independently represent a hydrogen atom or a $(C_1-C_4)$alkyl;
Alk represents a $(C_1-C_4)$alkyl which is unsubstituted or substituted one or more times by a fluorine atom.

The compounds of formula (I) can comprise one or more asymmetric carbon atoms. They can thus exist in the form of enantiomers or of diastereoisomers. These enantiomers or diastereoisomers, and also their mixtures, including racemic mixtures, come within the invention.

The compounds of formula (I) can exist in the form of bases or of addition salts with acids. Such addition salts come within the invention.

These salts are advantageously prepared with pharmaceutically acceptable acids but the salts of other acids of use in the purification or isolation of the compounds of formula (I) also come within the invention.

The compounds of formula (I) can exist in the form of hydrates or of solvates, namely in the form of combinations or associations with one or more molecules of water or with a solvent. Such hydrates and solvates also come within the invention.

According to the present invention, the N-oxides of the compounds comprising an amine also come within the invention.

The term "halogen atom" is understood to mean a bromine, chlorine, fluorine or iodine atom.

The term "$(C_1-C_3)$alkyl" or "$(C_1-C_4)$alkyl" respectively is understood to mean a linear or branched alkyl radical of one to three carbon atoms or of one to four carbon atoms respectively, such as the methyl, ethyl, propyl, isopropyl, butyl, isobutyl, sec-butyl or tert-butyl radical.

The term "$(C_1-C_5)$alkylene" is understood to mean a divalent radical of one to five carbon atoms, such as the methylene, ethylene, trimethylene, tetramethylene or pentamethylene radical.

The term "$(C_1-C_4)$alkoxy" is understood to mean a linear or branched alkoxy radical of one to four carbon atoms, such as the methoxy, ethoxy, propoxy, isopropoxy, butoxy, sec-butoxy or tert-butoxy radical.

The term "$(C_3-C_5)$cycloalkyl" is understood to mean a cyclopropyl, cyclobutyl or cyclopentyl radical.

The term "saturated or unsaturated 3- to 10-membered heterocyclic radical" is understood to mean a fused or bridged, mono-, di- or tricyclic, nonaromatic heterocyclic radical which can comprise a second heteroatom, such as nitrogen, oxygen or sulfur. These radicals comprise in particular the following radicals: 1-aziridinyl, 1-azetidinyl, 1-pyrrolidinyl, 1-piperidinyl, 1-piperazinyl, 1-hexahydroazepinyl, 4-morpholinyl, 4-thiomorpholinyl, 2-azabicyclo[2.2.2]oct-5-en-2-yl, 2-methyl-2-azoniabicyclo[2.2.2]oct-5-en-2-yl, 2-azaadamant-2-yl, 1,2,3,6-tetrahydropyridin-1-yl, 2-azabicyclo[2.2.1]heptan-2-yl, 2-azabicyclo[2.2.2]octan-2-yl, 1-azoniabicyclo[2.2.2]octan-1-yl, 1,4-diazepan-1-yl, 2,5-diazabicyclo[2.2.1]hept-2-yl, 3,8-diazabicyclo[3.2.1]oct-3-yl, 2,5-diazabicyclo[2.2.2]oct-2-yl, 1,4-diazabicyclo[3.2.1]oct-4-yl, hexahydropyrrolo[1,2-a]pyrazin-2(1H)-yl or octahydro-2H-pyrido[1,2-a]pyrazin-2-yl.

According to the present invention, preference is given to the compounds of formula (I) in which:
X represents a divalent $(C_1-C_5)$alkylene radical which is unsubstituted or substituted one or more times on a carbon atom by a fluorine atom or by a $(C_1-C_3)$alkyl;
$R_1$ represents:
an —$NR_8R_9$ group;
a piperidin-4-yl radical or a piperidin-3-yl radical which is unsubstituted or substituted by a methyl;
$R_2$ represents a halogen atom, a methyl or a methoxy;
$R_3$ represents a methoxy;
$R_4$ represents a hydrogen atom, a fluorine atom, a methyl or a methoxy;
$R_5$ represents a hydrogen atom, a halogen atom, a —$CO_2$Alk group or a —$CH_2OH$ radical;
$R_6$ represents a hydrogen atom, an Alk group, an OAlk group, a hydroxyl, a cyclopentyloxy or an —NHCON(Et)$_2$ group;
$R_7$ represents a hydrogen atom, a halogen atom, a methyl, a methoxy or a $CF_3$ radical;
or else $R_7$ is in the 3 position of the phenyl and, together with $R_6$, constitutes a trimethylene radical;
$R_8$ and $R_9$ each represent a methyl;
or else $R_8$ and $R_9$, together with the nitrogen atom to which they are bonded, constitute a heterocyclic radical chosen from: pyrrolidin-1-yl, piperidin-1-yl, morpholin-4-yl, piperazin-1-yl, 1,4-diazepan-1-yl, 2,5-diazabicyclo[2.2.1]hept-2-yl, 3,8-diazabicyclo[3.2.1]oct-3-yl, 2,5-diazabicyclo[2.2.2]oct-2-yl, 1,4-diazabicyclo[3.2.1]oct-4-yl, hexahydropyrrolo[1,2-a]pyrazin-2(1H)-yl or octahydro-2H-pyrido[1,2-a]pyrazin-2-yl, said heterocyclic radical being unsubstituted or substituted once or twice by a fluorine atom, an amino, a dimethylamino, a hydroxyl, an Alk group, a cyclobutyl or an —$SO_2$Me radical;
Alk represents a $(C_1-C_4)$alkyl which is unsubstituted or substituted one or more times by a fluorine atom;
in the form of the base or of an addition salt with an acid, and also in the hydrate or solvate form.

Preference is particularly given to the compounds of formula (I) in which:
X represents a divalent $(C_1-C_5)$alkylene radical;
$R_1$ represents:
a dimethylamino, a 3-aminopyrrolidin-1-yl, a 3-dimethylaminopyrrolidin-1-yl, a piperidin-1-yl, a 3,3-difluoropiperidin-1-yl, a 4,4-difluoropiperidin-1-yl, a 4-hydroxypiperidin-1-yl, a morpholin-4-yl, a 4-methylpiperazin-1-yl, a piperazin-1-yl, a 4-ethylpiperazin-1-yl, a 1,4-diazepan-1-yl, a 2,5-diaza-bicyclo[2.2.1]hept-2-yl, a 4-isopropylpiperazin-1-yl, a 3-methylpiperazin-1-yl, a 3,4-dimethylpiperazin-1-yl, a 4-cyclobutylpiperazin-1-yl, a 5-methyl-2,5-diazabicyclo[2.2.1]hept-2-yl, a 3,5-dimethylpiperazin-1-yl, a 4-methyl-1,4-diazepan-1-yl, an 8-methyl-3,8-diazabicyclo[3.2.1]oct-3-yl, a 2,6-dimethylpiperazin-1-yl, a 3-isopropylpiperazin-1-yl, a 2,2-dimethylpiperazin-1-yl, a 2,5-diazabicyclo[2.2.2]oct-2-yl, a 2,5-dimethylpiperazin-1-yl, a 2,2,4-trimethylpiperazin-1-yl, a 1,4-diazabicyclo[3.2.1]oct-4-yl, a 2-isopropylpiperazin-1-yl, a hexahydropyrrolo[1,2-a]pyrazin-2(1H)-yl, an octahydro-2H-pyrido-[1,2-a]pyrazin-2-yl, a 3-trifluoromethylpiperazin-1-yl, a 4-methylsulfonyl-piperazin-1-yl or a 4-(dimethylamino)piperidin-1-yl;
a piperidin-4-yl, a 1-methylpiperidin-4-yl, a 1-methylpiperidin-3-yl or a piperidin-3-yl;
$R_2$ represents a chlorine, fluorine or bromine atom, a methyl or a methoxy;
$R_3$ represents a methoxy;
$R_4$ represents a hydrogen atom, a fluorine atom, a methyl or a methoxy;
$R_5$ represents a hydrogen atom, a 3-chloro, a 5-fluoro, a 6-fluoro, a 5-methoxycarbonyl or a 5-hydroxymethyl;
$R_6$ represents a hydrogen atom, a methyl, an isopropyl, a methoxy, an ethoxy, an isopropoxy, a butyloxy, a tert-butyloxy, a cyclopentyloxy, a 1,1,2,2-tetrafluoroethyloxy, a 2,2-diethylureido, a difluoromethoxy, a trifluoromethoxy or a hydroxyl;
$R_7$ represents a hydrogen atom, a 3-methyl, a 2-methoxy, a 3-methoxy, a 3-fluoro, a 3-chloro or a 3-$CF_3$;
or else $R_7$ is in the 3 position of the phenyl and, together with $R_6$, constitutes a trimethylene radical;
in the form of the base or of an addition salt with an acid, and also in the hydrate or solvate form.

Preference is more particularly given to the compounds of formula (I) in which:

X represents a divalent trimethylene or pentamethylene radical;

$R_1$ represents:
  a dimethylamino, a 3-aminopyrrolidin-1-yl, a piperidin-1-yl, a 4,4-difluoro-piperidin-1-yl, a 4-hydroxypiperidin-1-yl, a 4-(dimethylamino)piperidin-1-yl, a morpholin-4-yl, a 4-methylpiperazin-1-yl, a piperazin-1-yl, a 3,4-dimethylpiperazin-1-yl, a 5-methyl-2,5-diazabicyclo[2.2.1]hept-2-yl, a 4-methyl-1,4-diazepan-1-yl, an 8-methyl-3,8-diazabicyclo[3.2.1]oct-3-yl or a 1,4-diazabicyclo[3.2.1]oct-4-yl;
  a piperidin-4-yl;

$R_2$ represents a chlorine, fluorine or bromine atom or a methyl;

$R_3$ represents a methoxy;

$R_4$ represents a hydrogen atom or a fluorine atom;

$R_5$ represents a hydrogen atom, a 5-methoxycarbonyl or a 5-hydroxymethyl;

$R_6$ represents a hydrogen atom, a methyl, a methoxy, an isopropoxy, an ethoxy, a butyloxy, a 1,1,2,2-tetrafluoroethyloxy, a 2,2-diethylureido, a difluoromethoxy, a trifluoromethoxy or a hydroxyl;

$R_7$ represents a hydrogen atom, a 2-methoxy, a 3-methoxy, a 3-methyl or a 3-fluoro;

in the form of the base or of an addition salt with an acid, and also in the hydrate or solvate form.

Mention may in particular be made, among the compounds of formula (I) which are subject matters of the invention, of the following compounds:

5-chloro-1-[(2,4-dimethoxyphenyl)sulfonyl]-3-(2-fluorophenyl)-6-methoxy-3-(3-(piperidin-4-yl)propyl)-1,3-dihydro-2H-indol-2-one, dextrorotatory isomer;

5-chloro-1-[(2,4-dimethoxyphenyl)sulfonyl]-3-(2-fluorophenyl)-6-methoxy-3-(3-(piperidin-4-yl)propyl)-1,3-dihydro-2H-indol-2-one, levorotatory isomer;

5-chloro-3-[3-(dimethylamino)propyl]-3-(2-fluorophenyl)-1-[(4-isopropoxyphenyl)sulfonyl]-6-methoxy-1,3-dihydro-2H-indol-2-one, dextrorotatory isomer;

3-{3-[(3R)-3-aminopyrrolidin-1-yl]propyl}-5-chloro-3-(2-fluorophenyl)-1-[(4-isopropoxyphenyl)sulfonyl]-6-methoxy-1,3-dihydro-2H-indol-2-one, dextrorotatory isomer;

3-{3-[(3S)-3-aminopyrrolidin-1-yl]propyl}-5-chloro-3-(2-fluorophenyl)-1-[(4-isopropoxyphenyl)sulfonyl]-6-methoxy-1,3-dihydro-2H-indol-2-one, dextrorotatory isomer;

3-{3-[(3R)-3-aminopyrrolidin-1-yl]propyl}-5-chloro-1-[(4-ethoxy-3-methoxy-phenyl)sulfonyl]-3-(2-fluorophenyl)-6-methoxy-1,3-dihydro-2H-indol-2-one, dextrorotatory isomer;

3-{3-[(3S)-3-aminopyrrolidin-1-yl]propyl}-5-chloro-1-[(4-ethoxy-3-methoxy-phenyl)sulfonyl]-3-(2-fluorophenyl)-6-methoxy-1,3-dihydro-2H-indol-2-one, dextrorotatory isomer;

5-chloro-1-[(2,4-dimethoxyphenyl)sulfonyl]-3-(2-fluorophenyl)-6-methoxy-3-(3-(piperidin-1-yl)propyl)-1,3-dihydro-2H-indol-2-one, dextrorotatory isomer;

5-chloro-3-[3-(4,4-difluoropiperidin-1-yl)propyl]-1-[(4-ethoxy-3-methoxy-phenyl)sulfonyl]-3-(2-fluorophenyl)-6-methoxy-1,3-dihydro-2H-indol-2-one, dextrorotatory isomer;

5-chloro-1-[(4-ethoxy-3-methoxyphenyl)sulfonyl]-3-(2-fluorophenyl)-3-[3-(4-hydroxypiperidin-1-yl)propyl]-6-methoxy-1,3-dihydro-2H-indol-2-one, dextrorotatory isomer;

5-chloro-1-[(4-ethoxy-3-methoxyphenyl)sulfonyl]-3-(2-fluorophenyl)-6-methoxy-3-(3-(morpholin-4-yl)propyl)-1,3-dihydro-2H-indol-2-one, dextrorotatory isomer;

5-chloro-1-[(2,4-dimethoxyphenyl)sulfonyl]-3-(2-fluorophenyl)-6-methoxy-3-[3-(4-methylpiperazin-1-yl)propyl]-1,3-dihydro-2H-indol-2-one, dextrorotatory isomer;

5-chloro-3-(2-fluorophenyl)-1-[(4-isopropoxyphenyl)sulfonyl]-6-methoxy-3-[3-(4-methylpiperazin-1-yl)propyl]-1,3-dihydro-2H-indol-2-one, dextrorotatory isomer;

5-chloro-1-[(4-ethoxy-3-methoxyphenyl)sulfonyl]-3-(2-fluorophenyl)-6-methoxy-3-[3-(4-methylpiperazin-1-yl)propyl]-1,3-dihydro-2H-indol-2-one, dextrorotatory isomer;

5-chloro-1-[(3,4-dimethoxyphenyl)sulfonyl]-3-(2-fluorophenyl)-6-methoxy-3-[3-(4-methylpiperazin-1-yl)propyl]-1,3-dihydro-2H-indol-2-one, dextrorotatory isomer;

5-chloro-1-[(2,4-dimethoxyphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-3-(2-fluorophenyl)-1-[(4-isopropoxyphenyl)sulfonyl]-6-methoxy-3-(3-(piperazin-1-yl)propyl)-1,3-dihydro-2H-indol-2-one, dextrorotatory isomer;

5-chloro-1-[(4-ethoxy-3-methoxyphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-1-[(3,4-dimethoxyphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-1-[(3,4-dimethylphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-3-(2-fluorophenyl)-6-methoxy-1-[(4-methoxy-3-methylphenyl)sulfonyl]-3-(3-(piperazin-1-yl)propyl)-1,3-dihydro-2H-indol-2-one;

5-chloro-1-[(4-ethoxyphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-1-[(4-ethoxy-3-methylphenyl)sulfonyl]-3-(2-fluorophenyl)-6-methoxy-3-(3-(piperazin-1-yl)propyl)-1,3-dihydro-2H-indol-2-one;

5-chloro-1-{[4-(difluoromethoxy)phenyl]sulfonyl}-3-(2-fluorophenyl)-6-methoxy-3-(3-(piperazin-1-yl)propyl)-1,3-dihydro-2H-indol-2-one, dextrorotatory isomer;

5-chloro-3-(2-fluorophenyl)-6-methoxy-3-(3-(piperazin-1-yl)propyl)-1-{[4-(tri-fluoromethoxy)phenyl]sulfonyl}-1,3-dihydro-2H-indol-2-one, dextrorotatory isomer;

5-chloro-3-(2-fluorophenyl)-6-methoxy-1-(phenylsulfonyl)-3-(3-(piperazin-1-yl)propyl)-1,3-dihydro-2H-indol-2-one, dextrorotatory isomer;

5-chloro-1-(2,3-dihydro-1H-inden-5-ylsulfonyl)-3-(2-fluorophenyl)-6-methoxy-3-(3-(piperazin-1-yl)propyl)-1,3-dihydro-2H-indol-2-one, dextrorotatory isomer;

5-chloro-1-{[3-fluoro-4-(1-methylethoxy)phenyl]sulfonyl}-3-(2-fluorophenyl)-6-methoxy-3-[3-(4-methylpiperazin-1-yl)propyl]-1,3-dihydro-2H-indol-2-one, dextrorotatory isomer;

5-chloro-3-(2-fluorophenyl)-6-methoxy-3-[3-(4-methylpiperazin-1-yl)propyl]-1-{[4-(1,1,2,2-tetrafluoroethoxy)phenyl]sulfonyl}-1,3-dihydro-2H-indol-2-one, dextrorotatory isomer;

3-(2-fluorophenyl)-6-methoxy-5-methyl-1-{[4-(1-methylethoxy)phenyl]sulfonyl}-3-[3-(4-methylpiperazin-1-yl)propyl]-1,3-dihydro-2H-indol-2-one, dextrorotatory isomer;

5-fluoro-3-(2-fluorophenyl)-6-methoxy-1-{[4-(1-methylethoxy)phenyl]sulfonyl}-3-[3-(4-methylpiperazin-1-yl)propyl]-1,3-dihydro-2H-indol-2-one, dextrorotatory isomer;

5-bromo-3-(2-fluorophenyl)-6-methoxy-1-{[4-(1-methylethoxy)phenyl]sulfonyl}-3-[3-(4-methylpiperazin-1-yl)propyl]-1,3-dihydro-2H-indol-2-one, dextrorotatory isomer;

3-[4-({3-[3-(dimethylamino)propyl]-3-(2-fluorophenyl)-6-methoxy-5-methyl-2-oxo-2,3-dihydro-1H-indol-1-yl}sulfonyl)-2-fluorophenyl]-1,1-diethylurea, dextrorotatory isomer;

3-[4-({3-[3-(dimethylamino)propyl]-3-(2-fluorophenyl)-6-methoxy-5-methyl-2-oxo-2,3-dihydro-1H-indol-1-yl}sulfonyl)-2-methylphenyl]-1,1-diethylurea, dextrorotatory isomer;

5-chloro-3-(2-fluorophenyl)-6-methoxy-3-[3-(8-methyl-3,8-diazabicyclo[3.2.1]oct-3-yl)propyl]-1-{[4-(1-methylethoxy)phenyl]sulfonyl}-1,3-dihydro-2H-indol-2-one, dextrorotatory isomer;

5-chloro-3-(2-fluorophenyl)-6-methoxy-3-[3-(5-methyl-2,5-diazabicyclo[2.2.1]hept-2-yl)propyl]-1-{[4-(1-methylethoxy)phenyl]sulfonyl}-1,3-dihydro-2H-indol-2-one, dextrorotatory isomer;

5-chloro-3-(2-fluorophenyl)-1-[(4-hydroxyphenyl)sulfonyl]-6-methoxy-3-[3-(4-methylpiperazin-1-yl)propyl]-1,3-dihydro-2H-indol-2-one, dextrorotatory isomer;

5-chloro-3-(2-fluorophenyl)-6-methoxy-3-[3-(4-methyl-1,4-diazepan-1-yl)propyl]-1-{[4-(1-methylethoxy)phenyl]sulfonyl}-1,3-dihydro-2H-indol-2-one, dextrorotatory isomer;

5-chloro-3-(2-fluorophenyl)-6-methoxy-1-{[4-(1-methylethoxy)phenyl]sulfonyl}-3-(5-(piperidin-1-yl)pentyl)-1,3-dihydro-2H-indol-2-one, dextrorotatory isomer;

5-chloro-3-[5-(dimethylamino)pentyl]-3-(2-fluorophenyl)-6-methoxy-1-{[4-(1-methylethoxy)phenyl]sulfonyl}-1,3-dihydro-2H-indol-2-one, dextrorotatory isomer;

5-chloro-3-{3-[(3S)-3,4-dimethylpiperazin-1-yl]propyl}-3-(2-fluorophenyl)-6-methoxy-1-{[4-(1-methylethoxy)phenyl]sulfonyl}-1,3-dihydro-2H-indol-2-one, dextrorotatory isomer;

5-chloro-6-methoxy-1-{[4-(1-methylethoxy)phenyl]sulfonyl}-3-[3-(4-methyl-piperazin-1-yl)propyl]-3-phenyl-1,3-dihydro-2H-indol-2-one, dextrorotatory isomer;

5-chloro-3-{3-[(5S)-1,4-diazabicyclo[3.2.1]oct-4-yl]propyl}-3-(2-fluorophenyl)-6-methoxy-1-{[4-(1-methylethoxy)phenyl]sulfonyl}-1,3-dihydro-2H-indol-2-one, dextrorotatory isomer;

1-[(4-butoxyphenyl)sulfonyl]-5-chloro-3-(2-fluorophenyl)-6-methoxy-3-[3-(4-methylpiperazin-1-yl)propyl]-1,3-dihydro-2H-indol-2-one, dextrorotatory isomer;

5-chloro-3-[3-[4-(dimethylamino)piperidin-1-yl]propyl]-3-(2-fluorophenyl)-1-[(4-isopropoxyphenyl)sulfonyl]-6-methoxy-1,3-dihydro-2H-indol-2-one;

1-[(3-fluoro-4-isopropoxyphenyl)sulfonyl]-3-(2-fluorophenyl)-5,6-dimethoxy-3-[3-(4-methylpiperazin-1-yl)propyl]-1,3-dihydro-2H-indol-2-one;

5-fluoro-1-[(3-fluoro-4-isopropoxyphenyl)sulfonyl]-3-(2-fluorophenyl)-6-methoxy-3-[3-(4-methylpiperazin-1-yl)propyl]-1,3-dihydro-2H-indol-2-one;

3-(2-fluorophenyl)-5,6-dimethoxy-1-[(4-methoxy-3-methylphenyl)sulfonyl]-3-[3-(4-methylpiperazin-1-yl)propyl]-1,3-dihydro-2H-indol-2-one;

methyl 3-[5-chloro-1-[(4-isopropoxyphenyl)sulfonyl]-6-methoxy-3-[3-(4-methylpiperazin-1-yl)propyl]-2-oxo-2,3-dihydro-1H-indol-3-yl]-4-fluorobenzoate;

5-chloro-3-[2-fluoro-5-(hydroxymethyl)phenyl]-1-[(4-isopropoxyphenyl)sulfonyl]-6-methoxy-3-[3-(4-methylpiperazin-1-yl)propyl]-1,3-dihydro-2H-indol-2-one;

in the form of the base or of addition salts with acids, and also in the hydrate or solvate form.

In that which follows, the term "protective group Pg" is understood to mean a group which makes it possible, on the one hand, to protect a reactive functional group, such as a hydroxyl or an amine, during a synthesis and, on the other hand, to regenerate the reactive functional group intact at the end of the synthesis. Examples of protective groups and of protecting and deprotecting methods are given in "Protective Groups in Organic Synthesis", Green et al., 4$^{th}$ Edition, John Wiley & Sons Inc., New York, 2007.

The term "leaving group" is understood to mean, in that which follows, a group which can be easily split from a molecule by cleavage of a heterolytic bond, with departure of an electron pair. This group can thus be easily replaced by another group during a substitution reaction, for example. Such leaving groups are, for example, halogens or an activated hydroxyl group, such as a methanesulfonate, benzenesulfonate, p-toluenesulfonate, triflate, acetate, and the like. Examples of leaving groups and references for their preparation are given in "Advanced Organic Chemistry", M. B. Smith and J. March, 6th Edition, Wiley Interscience, 2007, pp. 496-501.

In accordance with the invention, the compounds of formula (I) can be prepared according to a process which is characterized in that:

a compound of formula:

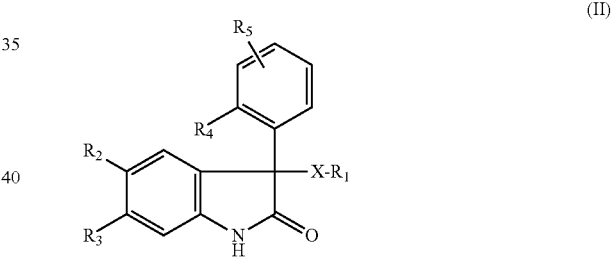

(II)

in which X, $R_1$, $R_2$, $R_3$, $R_4$ and $R_5$ are as defined for a compound of formula (I), is reacted, in the presence of a base, with a sulfonyl halide of formula:

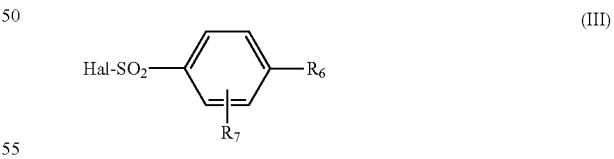

(III)

in which $R_6$ and $R_7$ are as defined for a compound of formula (I) and Hal represents a halogen atom.

The compound of formula (I) is optionally converted into one of its salts with inorganic or organic acids.

The reaction is carried out in the presence of a strong base, such as a metal hydride, for example sodium hydride, or an alkali metal alkoxide, for example potassium tert-butoxide, in an anhydrous solvent, such as N,N-dimethylformamide or tetrahydrofuran, and at a temperature of between −70° C. and +60° C. The reaction is preferably carried out using a compound of formula (III) in which Hal=Cl.

According to an alternative form of the process, the compounds of formula (I) can be prepared according to a process which is characterized in that:
a compound of formula:

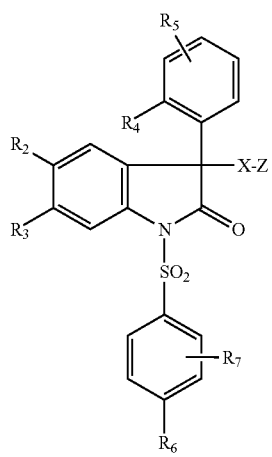

in which X, $R_2$, $R_3$, $R_4$, $R_5$, $R_6$ and $R_7$ are as defined for a compound of formula (I) and Z represents a leaving group, such as a halogen atom or a methanesulfonate or p-toluenesulfonate group, is reacted with a compound of formula:

in which $R_1$ is as defined for a compound of formula (I).

The compound of formula (I) is optionally converted into one of its salts with inorganic or organic acids.

The reaction is carried out in the presence of an alkali metal carbonate, such as sodium carbonate, and in the presence of an alkali metal halide, such as sodium iodide, in a solvent, such as acetonitrile or N,N-dimethylformamide, and at a temperature between ambient temperature and the reflux temperature of the solvent.

The compounds of formula (I) thus obtained can subsequently be separated from the reaction medium and purified according to conventional methods, for example by crystallization or chromatography.

The compounds of formula (I) thus obtained are isolated in the free base or salt form according to conventional techniques.

The compounds of formula (II) are prepared by reaction of a 1,3-dihydro-2H-indol-2-one compound of formula:

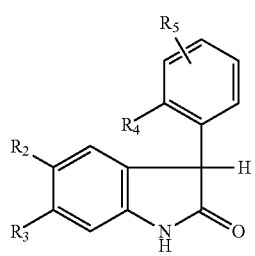

in which $R_2$, $R_3$, $R_4$ and $R_5$ are as defined for a compound of formula (I), with a compound of formula:

in which X et $R_1$ are as defined for a compound of formula (I) and Z represents a leaving group, such as a halogen atom, preferably iodine or bromine, or a methanesulfonate or p-toluenesulfonate group.

The reaction is carried out in the presence of a strong base, such as an alkali metal alkoxide, for example potassium tert-butoxide, in a solvent, such as tetrahydrofuran or N,N-dimethylformamide, and at a temperature between −50° C. and ambient temperature.

The compounds of formula (II) can also be prepared by reaction of a compound of formula:

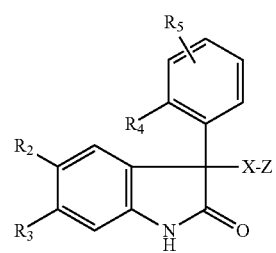

in which $R_2$, $R_3$, $R_4$ and $R_5$ are as defined for a compound of formula (I) and Z represents a leaving group as described above, with a compound of formula $R_1H$ (V). The reaction is carried out according to the operating conditions described above for the reaction of a compound of formula (IV) with a compound of formula (V).

The compounds of formula (III) are commercially available, are known or are prepared by known methods, such as those described in EP 0 469 984 B and WO 95/18105. For example, the compounds of formula (III) can be prepared by halogenation of the corresponding benzenesulfonic acids or their salts, for example their sodium or potassium salts. The reaction is carried out in the presence of a halogenating agent, such as phosphorus oxychloride, thionyl chloride, phosphorus trichloride, phosphorus tribromide or phosphorus pentachloride, without solvent or in a solvent, such as a halogenated hydrocarbon or N,N-dimethylformamide and at a temperature between −10° C. and 200° C.

The compounds of formula (III) can also be prepared by reaction of chlorosulfonic acid with a compound of formula:

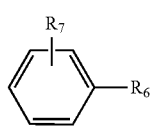

in which $R_6$ and $R_7$ are as defined for a compound of formula (I). The reaction is carried out according to the procedures described in Chlorosulfonic Acid; R. J. Cremlyn; The Royal Society of Chemistry, 2002.

The compounds of formula (IV) are prepared by reaction of a compound of formula:

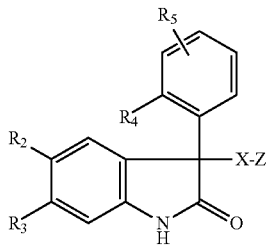

(VIII)

in which X, $R_2$, $R_3$, $R_4$ and $R_5$ are as defined for a compound of formula (I) and Z represents a leaving group as described above, with a compound of formula (III). The reaction is carried out according to the operating conditions described above for the reaction of a compound of formula (II) with a compound of formula (III).

The compounds of formula (V) are commercially available, are known or are prepared according to methods known to a person skilled in the art.

The compounds of formula (VI) are known and are prepared according to known methods, such as those described in WO 95/18105 or in WO 01/55130, which use the chemistry of commercial isatins, which are known or prepared according to known methods, such as described by Katritzky et al. in "Advances in Heterocyclic Chemistry", Academic Press, 1975. Vol 18, pp. 1-58. The 3-hydroxyindolinones which are direct precursors of the compounds (VI) are reduced according to known methods which employ reducing agents, such as triethylsilane, in trifluoroacetic acid or in the presence of Lewis acid, such as the boron trifluoride/diethyl ether complex (Bioorg. Med. Chem. Lett., 175-178).

The compounds of formula (VI) can also be prepared according to SCHEME 1 below in which R represents a $(C_1-C_4)$alkyl.

SCHEME 1

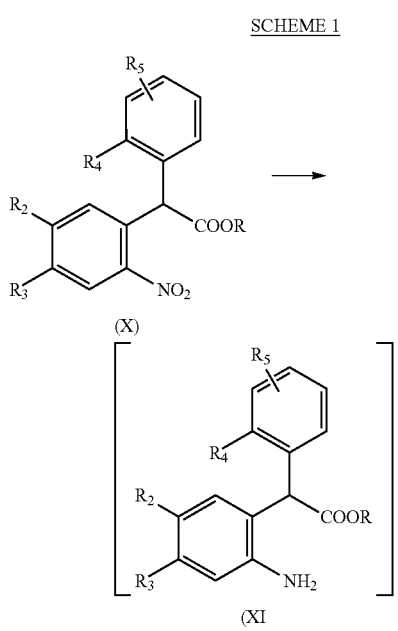

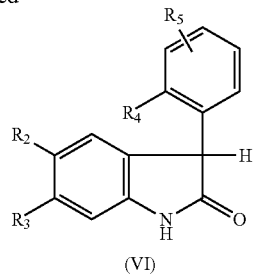

(VI)

According to SCHEME 1, the compounds of formula (VI) are obtained by cyclization of the amine of formula (XI) generated in situ by reduction of the nitro group of the compounds of formula (X). The reaction is carried out in the presence of a metal, such as tin or iron, in an acidic medium, such as acetic acid, in a solvent, such as methanol, and at a temperature between ambient temperature and 100° C.

The compounds of formula (VII) are commercially available or are prepared according to known methods.

The compounds of formula (VIII) are prepared by reaction of a compound of formula:

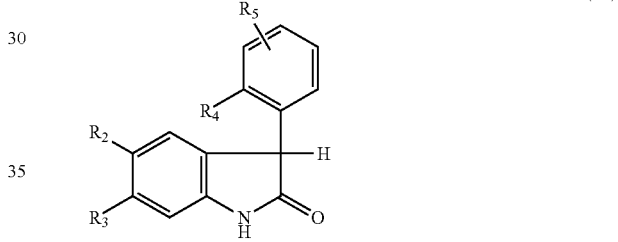

(VI)

in which $R_2$, $R_3$, $R_4$ and $R_5$ are as defined for a compound of formula (I), with a compound of formula:

Hal—X—Z     (XII)

in which X is as defined for a compound of formula (I), Z is as defined above and Hal represents a halogen atom.

The reaction is carried out in the presence of a strong base, such as an alkali metal alkoxide, for example potassium tert-butoxide, in a solvent, such as tetrahydrofuran or N,N-dimethylformamide, and at a temperature between −50° C. and ambient temperature.

The compounds of formula (IX) are known or are prepared according to known methods.

The compounds of formula (X) are prepared by reaction of compounds of formula:

(XIII)

in which $R_2$ and $R_3$ are as defined for a compound of formula (I) with a compound of formula:

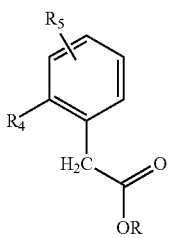

(XIV)

in which $R_4$ and $R_5$ are as defined for a compound of formula (I).

The reaction is carried out in the presence of a strong base, such as an alkali metal alkoxide, for example potassium tert-butoxide, or such as a metal hydride, such as sodium hydride, in an anhydrous solvent, such as N,N-dimethylformamide, and at a temperature between −50° C. and ambient temperature.

The compounds of formulae (XII), (XIII) and (XIV) are prepared according to methods well known to a person skilled in the art.

The N-oxides of the compounds comprising an amine are prepared according to known methods known to a person skilled in the art by reaction of the amine with organic peracids, such as peracetic acid, trifluoroperacetic acid, performic acid, perbenzoic acid or its derivatives, such as 3-chloroperbenzoic acid, at temperatures between 0° C. and 90° C., preferably at temperatures below 50° C.

Conventional separating techniques can be used to obtain the compounds of formula (I) in the form of optically pure isomers: for example fractional recrystallizations of a salt formed from the racemic base with an optically active acid, the principle of which is well known, or conventional techniques for preparative supercritical chromatography on a chiral phase can be used.

The optically pure compounds of formula (I) can also be prepared from an optically pure intermediate compound of use in the preparation of the compounds of formula (I) according to the techniques described in WO 03/008407.

The preparation of some compounds in accordance with the invention is described in the following EXAMPLES. These examples are not limiting and serve only to illustrate the present invention. The numbers of the compounds given in the examples refer to those given in TABLE (IV) below, in which the chemical structures and the physical properties of a few compounds according to the invention are illustrated.

The following abbreviations are used in the Preparations and in the Examples:
ether: diethyl ether
iso ether: diisopropyl ether
DMSO: dimethyl sulfoxide
DMF: N,N-dimethylformamide
THF: tetrahydrofuran
DCM: dichloromethane
AcOEt: ethyl acetate
DIPEA: diisopropylethylamine
TFA: trifluoroacetic acid
2N hydrochloric ether: 2N solution of hydrochloric acid in diethyl ether
M.p.: melting point
AT: ambient temperature
B.p.: boiling point
HPLC: high performance liquid chromatography
Silica H: silica gel 60H, sold by Merck (Darmstadt)
Buffer solution pH=2: solution of 16.66 g of $KHSO_4$ and 32.32 g of $K_2SO_4$ in 1 liter of water.

The proton nuclear magnetic resonance ($^1H$ NMR) spectra are recorded in $d_6$-DMSO. The chemical shifts δ are expressed as parts per million (ppm). The following abbreviations are used for the interpretation of the spectra: s: singlet, d: doublet, t: triplet, q: quartet, bup: broad unresolved peak, mt: multiplet, bs: broad singlet, dd: double doublet.

The optical rotations are measured on a Perkin-Elmer 241 polarimeter.

The mixtures of solvents are quantified in ratios by volume.

The compounds according to the invention are analyzed by coupled LC/UV/MS (liquid chromatography/UV detection/mass spectrometry). The molecular peak ($MH^+$) and the retention time (rt) in minutes are measured.

System 1 at pH 3: Method 1 (M1)
Instrument (Agilent): HPLC chain: series 1100;
Mass spectrometer: MSD SL (Agilent)
Software: Chemstation version B.01.03 from Agilent LC/UV
Column: Symmetry C18 3.5 µm (2.1×50 mm) (Waters)
Column temperature: 25° C.
Eluents: A: $H_2O_2$+0.005% TFA
B: $CH_3CN$+0.005% TFA
Flow rate: 0.4 ml/min
Gradient:

| Time (min) | % (v/v) A/B |
|---|---|
| 0 | 100/0 |
| 10 | 10/90 |
| 15 | 10/90 |

UV detection: 220 nm
Injection volume: 2 µl of a 0.5 mg/ml solution
MS
Ionization mode: Positive electrospray $ESI^+$ mode
Mass range: 90-1500 uma
System 2 at pH 7: Method 2 (M2)
Instrument (Agilent): HPLC chain: series 1100;
Mass spectrometer: MSD SL (Agilent)
Software: Chemstation version B.01.03 from Agilent LC/UV
Column: X Terra C18 3.5 µm (2.1×50 mm) (Waters)
Column temperature: 30° C.
Eluents: A: Ammonium acetate buffer, 10 mM, pH 7
B: $CH_3CN$
Flow rate: 0.4 ml/min
Gradient:

| Temps (min.) | % (v/v) A/B |
|---|---|
| 0 | 100/0 |
| 10 | 10/90 |
| 15 | 10/90 |

UV detection: 220 nm
Injection volume: 2 µl of a 0.5 mg/ml solution
MS
Ionization mode: Positive electrospray $ESI^+$ mode
Mass range: 90-1500 uma
System 3 at pH 2.2: Method 3 (M3)
Instrument (Waters): HPLC chain: Alliance 2695;
UV detector: PDA 996

Mass spectrometer: Platform LCZ (Micromass)
Software: MassLynx version 4.0 from Waters-Micromass
LC/UV
Column: Symmetry C18 3.5 μm (2.1×50 mm) (Waters)
Column temperature: 40° C.
Eluents: A: $H_2O_2$+0.05% TFA
B: $CH_3CN$+0.035% TFA
Flow rate: 0.5 ml/min
Gradient:

| Temps (min.) | % (v/v) A/B |
|---|---|
| 0.0 | 100/0 |
| 6.0 | 0/100 |
| 7.0 | 0/100 |
| 7.1 | 100/0 |
| 10.0 | 100/0 |

UV detection: 220 nm
Injection volume: 2 μl of a 0.5 mg/ml solution
MS
Ionization mode: Positive electrospray ESI+ mode
Mass range: 120-1500 uma
System 4 at pH 3: Method 4 (M4)
Instrument (Agilent): HPLC chain: series 1100;
Mass spectrometer: MSD SL (Agilent)
Software: Chemstation version B.01.03 from Agilent
LC/UV
Column: Symmetry C18 3.5 μm (2.1×50 mm) (Waters)
Column temperature: 25° C.
Eluents: A: $H_2O$+0.005% TFA
B: $CH_3CN$+0.005% TFA
Flow rate: 0.4 ml/min
Gradient:

| Time (min.) | % (v/v) A/B |
|---|---|
| 0 | 100/0 |
| 10 | 0/100 |
| 15 | 0/100 |

UV detection: 220 nm
Injection volume: 2 μl of a 0.5 mg/ml solution
MS
Ionization mode: Positive electrospray ESI+ mode
Mass range: 90-1500 uma
System 5 at pH 3: Method 5 (M5)
Instrument (Agilent): HPLC chain: series 1100;
Mass spectrometer: MSD SL (Agilent)
Software: Chemstation version B.01.03 from Agilent
LC/UV
Column: Symmetry C18 3.5 μm (2.1×50 mm) (Waters)
Column temperature: 25° C.
Eluents: A: $H_2O$+0.005% TFA
B: $CH_3CN$+0.005% TFA
Flow rate: 0.4 ml/min
Gradient:

| Time (min.) | % (v/v) A/B |
|---|---|
| 0 | 100/0 |
| 30 | 0/100 |
| 35 | 0/100 |

UV detection: 220 nm
Injection volume: 2 μl of a 0.5 mg/ml solution
MS
Ionization mode: Positive electrospray ESI+ mode
Mass range: 90-1500 uma
System 6 at pH 2.2: Method 6 (M6)
Instrument (Waters): HPLC chain: Alliance 2695;
UV detector: PDA 996
Mass spectrometer: ZQ (Micromass)
Software: MassLynx version 4.1 from Waters-Micromass
LC/UV
Phenomenex Luna C18(2) —HST 2.5 μm 2.0×30 mm
Column temperature: 50° C.
Eluents: A: $H_2O$+0.05% TFA
B: $CH_3CN$+0.035% TFA
Flow rate: 1 ml/min
Gradient:

| Time (min.) | % (v/v) A/B |
|---|---|
| 0.0 | 100/0 |
| 2.5 | 0/100 |
| 3.5 | 0/100 |
| 3.6 | 100/0 |
| 5 | 100/0 |

UV detection: 220 nm
Injection volume: 2 μl of a 0.5 mg/ml solution
MS
Ionization mode: Positive electrospray ESI+ mode
Mass range: 120-1500 uma

PREPARATIONS

1. Preparations of the Compounds of Formula (VI)

Preparation 1.1

5-Chloro-3-(2-chlorophenyl)-6-methoxy-1,3-dihydro-2H-indol-2-one $R_2$=Cl; $R_3$=OMe; $R_4$=Cl; $R_5$=H     (VI)

A—Methyl(5-chloro-4-methoxy-2-nitrophenyl)(2-chlorophenyl)acetate

A suspension of 0.6 g of 60% sodium hydride in oil in 10 ml of DMF is cooled to −5° C., a solution of 1.03 g of 1-chloro-5-fluoro-2-methoxy-4-nitrobenzene (prepared according to EP 061 741) and 0.93 g of ethyl (2-chlorophenyl)acetate in 25 ml of DMF is added dropwise and the mixture is left stirring for 1 hour while allowing the temperature to rise to 3° C. A saturated $NH_4Cl$ solution is added, extraction is carried out with AcOEt, the organic phase is washed with water and dried over $Na_2SO_4$, and the solvents are evaporated under vacuum. The residue is chromatographed on silica gel, elution being carried out with a cyclohexane/AcOEt (97/3; v/v) mixture. The expected compound is obtained in the liquid form.

19

B—5-Chloro-3-(2-chlorophenyl)-6-methoxy-1,3-dihydro-2H-indol-2-one 0.8 g of iron and then 3.7 ml of AcOH are added to a mixture of 1.1 g of the compound from the preceding stage in 15 ml of MeOH and the mixture is heated at reflux for 16 hours. The solvents are partially concentrated under vacuum, a 5% NaHCO$_3$ solution and then AcOEt are added and the mixture is left stirring at AT. The reaction mixture is filtered, the filtrate is separated by settling, the organic phase is washed with a 5% NaHCO$_3$ solution and dried over Na$_2$SO$_4$, and the solvent is evaporated under vacuum. The residue is taken up in iso ether and the precipitate formed is filtered off and dried at 50° C. under vacuum. The expected compound is obtained, M.p.=249° C.

Preparation 1.2

5-Chloro-3-(2-fluorophenyl)-6-methoxy-1,3-dihydro-2H-indol-2-one

R$_2$=Cl; R$_3$=OMe; R$_4$=F; R$_5$=H    (VI)

A—Methyl 5-chloro-4-methoxy-2-nitrophenyl)(2-fluorophenyl)acetate

A suspension of 2.92 g of 60% sodium hydride in oil in 50 ml of DMF is cooled to −20° C., a solution of 5 g of 1-chloro-5-fluoro-2-methoxy-4-nitrobenzene (prepared according to EP 061 741) and 4.5 g of methyl(2-fluorophenyl)acetate in 60 ml of DMF is added dropwise and the mixture is left stirring for 1 hour while allowing the temperature to rise to 3° C. A saturated NH$_4$Cl solution is added, the reaction mixture is extracted with AcOEt, the organic phase is washed with water and dried over Na$_2$SO$_4$, and the solvents are evaporated under vacuum. The residue is chromatographed on silica gel, elution being carried out with a cyclohexane/AcOEt (97/3; v/v) mixture. The expected compound is obtained in the solid form, M.p.=87° C.

$^1$H NMR: d$_6$-DMSO (250 MHz): δ (ppm): 3.70, s, 3H, 4.01, s, 3H, 5.78, s, 1H

B—5-Chloro-3-(2-fluorophenyl)-6-methoxy-1,3-dihydro-2H-indol-2-one 0.8 g of iron and then 3.7 ml of AcOH are added to a mixture of 1.1 g of the compound from the preceding stage in 15 ml of MeOH and the mixture is heated at reflux for 16 hours. The solvents are partially concentrated under vacuum, a 5% NaHCO$_3$ solution and then AcOEt are added and the mixture is left stirring at AT. The reaction mixture is filtered, the filtrate is separated by settling, the organic phase is washed with a 5% NaHCO$_3$ solution and dried over Na$_2$SO$_4$, and the solvent is evaporated under vacuum. The residue is taken up in iso ether and the precipitate formed is filtered off and dried at 50° C. under vacuum. The expected compound is obtained, M.p.=214° C.

$^1$H NMR: d$_6$-DMSO (250 MHz): δ (ppm): 3.86, s, 3H, 4.99, s, 1H, 6.66, s, 1H, 6.96, s, 1H, 7.14-7.43, mt, 4H, 10.71, s, 1H.

The compounds (VI), collated in Table I below, are prepared from appropriate and known ortho-fluoronitrobenzenes (XIII) and alkyl phenylacetates (XIV) according to the procedures described in the above Preparations:

TABLE I

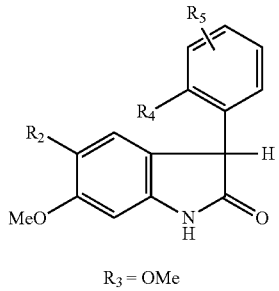

(VI)

R$_3$ = OMe

| Preparations | R$_2$ | R$_4$ | R$_5$ | M.p. ° C. MH$^+$; rt (min) (Conditions) |
|---|---|---|---|---|
| 1.3 | Cl | Me | H | — 288; 7.73 (M 4) |
| 1.4 | Cl | F | 6-F | — 310; 8.02 (M 4) |
| 1.5 | Br | F | H | — 337; 2.24 (M 6) |
| 1.5a | Cl | F | 5-CO$_2$Me | 220 350; 7.95 (M 4) |

Preparation 1.6

5-Fluoro-3-(2-fluorophenyl)-6-methoxy-1,3-dihydro-2H-indol-2-one

R$_2$=F; R$_3$=OMe; R$_4$=F; R$_5$=H    (VI)

A—5-Fluoro-6-methoxyisatin

A1. N-(4-Fluoro-3-methoxyphenyl)-2-(hydroxyimino)ethanamide 118.4 g of sodium sulfate, 26.3 g of hydroxylamine chloride and 20.89 g of chloral hydrate are added, in this order, to a suspension of 14.7 g of 4-fluoro-3-methoxyaniline in 695 ml of water and 35 ml of 2N hydrochloric acid. The reaction mixture is heated at 55° C. for 6 hours. It is cooled to approximately 15° C. The expected compound is obtained and is filtered off, washed and dried.

MH$^+$=213; rt=5.94 min; (M 4).

A2. 5-Fluoro-6-methoxyisatin 19.43 g of the compound obtained in the preceding stage are added, slowly and portionwise, to 125 ml of concentrated sulfuric acid heated to approximately 50° C. The mixture is heated at approximately 60° C. for 20 minutes before cooling and then running under 2 l of water at a temperature of 45° C. The mixture is allowed to cool to approximately 20° C. with stirring overnight. The expected compound is obtained and is filtered off, washed and dried.

M.p.=260° C.; MH$^+$=196; rt=1.52 min; (M 6).

B—5-Fluoro-3-(2-fluorophenyl)-3-hydroxy-6-methoxy-1,3-dihydro-2H-indol-2-one 13.45 g of 2-bromofluorobenzene are slowly added to 76.5 ml of a 15% solution, cooled to 0° C., of the isopropylmagnesium chloride/magnesium chloride complex in THF. After stirring at 0° C. for 1 hour, a mixture of 6 g of the compound obtained in the preceding stage in 50 ml of THF is slowly introduced. The temperature is subsequently allowed to rise to 20° C. overnight. The medium is run onto 20 ml of 1N hydrochloric acid and extracted with 150 ml of AcOEt. Filtration is carried out on a Buchner funnel and separation by settling is allowed to take place. The organic phase is dried over $Na_2SO_4$ and evaporated to dryness. The solid residue is taken up in isopropyl ether. The expected compound is obtained by filtering and drying.

$MH^+$=292; rt=4.31 min; (M 3).

C—5-Fluoro-3-(2-fluorophenyl)-6-methoxy-1,3-dihydro-2H-indol-2-one 31.6 ml of triethylsilane and then 2.53 ml of trifluoroborane/diethyl ether are added to 11 g of the compound obtained in the preceding stage in 127 ml of 1,2-dichloroethane. The mixture is heated at 75° C. for 1 hour 30 minutes. It is cooled to 20° C. and evaporated under reduced pressure, and the residue is taken up in 20 ml of AcOEt. The expected compound is obtained by filtering and drying.

$MH^+$=276; rt=4.73 min; (M 3).

The compounds (VI), collated in Table II below, are obtained from appropriate isatins (prepared as described above) and appropriate phenylmagnesium compounds (commercially available or prepared as above or more conventionally with magnesium filings) according to the procedure described in the above Preparation:

TABLE II (VI)

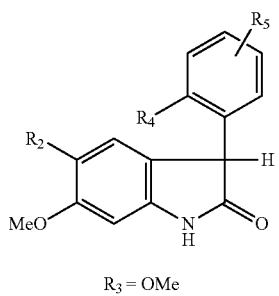

$R_3$ = OMe

| Preparations | $R_2$ | $R_4$ | $R_5$ | M.P. ° C. $MH^+$; rt (min) (Conditions) |
|---|---|---|---|---|
| 1.7 | Cl | F | 5-F | 225 310; 7.52 (M 4) |
| 1.8 | Cl | H | H | 248 274; 7.43 (M 4) |
| 1.9 | Cl | F | 3-Cl | 225 326; 7.98 (M 4) |
| 1.10 | Me | F | H | — 272; 5.02 (M 4) |
| 1.11 | OMe | F | H | — 288; 4.17 (M 4) |

2a. Preparations of compounds of formula (VIII)

Preparation 2a.1

5-Chloro-3-(4-chlorobutyl)-3-(2-chlorophenyl)-6-methoxy-1,3-dihydro-2H-indol-2-one

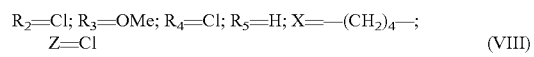

$R_2$=Cl; $R_3$=OMe; $R_4$=Cl; $R_5$=H; X=—$(CH_2)_4$—; Z=Cl (VIII)

A solution of 0.46 g of the compound from Preparation 1.1 in 11 ml of DMF is cooled to −50° C. under an argon atmosphere, 0.19 g of potassium tert-butoxide is added and the mixture is left stirring while allowing the temperature to rise to −20° C. The reaction mixture is cooled to −50° C., a solution of 0.19 ml of 1-bromo-4-chlorobutane in 5 ml of DMF is added dropwise and the mixture is left stirring for 16 hours while allowing the temperature to rise to 10° C. A saturated $NH_4Cl$ solution is added, extraction is carried out with AcOEt, the organic phase is washed with water and dried over $Na_2SO_4$, and the solvent is evaporated under vacuum. The residue is chromatographed on silica gel, elution being carried out with the gradient of the cyclohexane/AcOEt mixture from 100/0 (v/v) to 60/40 (v/v). The expected compound is obtained, M.p.=80° C.

Preparation 2a.2

5-Chloro-3-(3-chloropropyl)-3-(2-fluorophenyl)-6-methoxy-1,3-dihydro-2H-indol-2-one, dextrorotatory isomer and levorotatory isomer

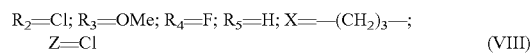

$R_2$=Cl; $R_3$=OMe; $R_4$=F; $R_5$=H; X=—$(CH_2)_3$—; Z=Cl (VIII)

A solution of 6 g of the compound from Preparation 1.2 in 200 ml of DMF is cooled to −50° C. under an argon atmosphere, 2.65 g of potassium tert-butoxide are added and the mixture is left stirring while allowing the temperature to rise to −20° C. The reaction mixture is cooled to −50° C., 2.29 ml of 1-chloro-3-iodopropane are added dropwise and the mixture is left stirring for 16 hours while allowing the temperature to rise to 15° C. A saturated $NH_4Cl$ solution is added, extraction is carried out with AcOEt, the organic phase is washed with water and dried over $Na_2SO_4$, and the solvent is evaporated under vacuum. The residue is taken up in iso ether and the precipitate formed is filtered off. The expected compound is obtained, M.p.=179° C.

The enantiomers of the compound thus obtained are separated by chiral phase liquid chromatography under the following conditions:

Equipment: Waters Delta Prep 4000 chromatography system;
Chiral column: CHIRALPAK AS-VCSP:
Mobile phase: 100% acetonitrile;
Flow rate: 120 ml/minute;
Pressure: 50 bar;
UV detection: 254 nm.

After separation of the enantiomers, the following are obtained:
the dextrorotatory isomer:
$\alpha_D^{20}$=+79° (c=1; AcOEt);
$^1H$ NMR: $d_6$-DMSO (250 MHz): δ (ppm): 1.21-1.43, mt, 1H, 1.43-1.65, mt, 1H, 2.16-2.47, mt, 2H, 3.61, t, 2H, 3.861, s, 3H, 6.664, s, 1H, 6.96, s, 1H, 7.03-7.136, mt, 1H, 7.23-7.41, mt, 2H, 7.57-7.66, mt, 1H, 10.80, s, 1H;

the levorotatory isomer:

$\alpha_D^{20}$=−77° (c=1; AcOEt).

The racemic or chiral compounds of formula (VIII), collated in Table III below, are obtained from appropriate compounds described above of formula (VI) and appropriate compounds of formula (XII) under similar conditions:

TABLE III (VIII)

[Structure: indolin-2-one with R$_2$ and MeO on benzene ring, R$_4$/R$_5$ substituted phenyl at 3-position, and X—Cl group]

Z = Cl
R$_3$ = OMe

| Preparation | X | R$_2$ | R$_4$ | R$_5$ | $\alpha_D^{20}$ (c; solvent) (c = 1, solvent) | M.p. °C. MH$^+$; rt (min) (Conditions) |
|---|---|---|---|---|---|---|
| 2a.3 | (CH$_2$)$_3$ | Cl | Me | H | +71.8° (AcOEt) | 84 364; 9.11 (M 4) |
| 2a.4 | (CH$_2$)$_3$ | Cl | F | 6-F | +117.3° (AcOEt) | 90 386; 8.48 (M 4) |
| 2a.5 | (CH$_2$)$_3$ | Cl | F | 4-F | +57.8° (AcOEt) | 138 386; 8.50 (M 4) |
| 2a.6 | (CH$_2$)$_3$ | Br | F | H | Racemate | — 412; 5.66 (M 3) |
| 2a.7 | (CH$_2$)$_3$ | F | F | H | +115.3° (AcOEt) | — 351; 7.88 (M 4) |
| 2a.8 | (CH$_2$)$_3$ | Cl | F | 5-F | +82° (AcOEt) | — 386; 8.92 (M 4) |
| 2a.9 | (CH$_2$)$_3$ | Cl | H | H | Racemate | 200 350; 8.44 (M 4) |
| 2a.10 | (CH$_2$)$_3$ | Cl | F | 3-Cl | +95° (AcOEt) | — 402; 9.38 (M 4) |
| 2a.11 | (CH$_2$)$_3$ | Me | F | H | +84.9° (AcOEt) | — 348; 8.30 (M 4) |
| 2a.12 | (CH$_2$)$_3$ | OMe | F | H | +86.6° (AcOEt) | — 364; 7.64 (M 4) |
| 2a.13 | (CH$_2$)$_4$ | Cl | F | H | Racemate | — 382; 9.05 (M 4) |
| 2a.14 | (CH$_2$)$_5$ | Cl | F | H | +66° (c = 1, MeOH) | — 396; 9.45 (M 4) |
| 2a.15 | (CH$_2$)$_2$ | Cl | F | H | Racemate | — 354; 8.69 (M 4) |
| 2a.16 | (CH$_2$)$_3$ | Cl | F | 5-CO$_2$Me | +132.4° (c = 0.5, AcOEt) | — 426; 8.78 (M 4) |

2. Preparations of the compounds of formula (II)

Preparation 2.1 tert-Butyl 4-[3-[5-chloro-3-(2-fluorophenyl)-6-methoxy-2-oxo-2,3-dihydro-1H-indol-3-yl]propyl]piperidine-1-carboxylate (II):

R$_2$═Cl; R$_3$═OMe; R$_4$═F; R$_5$═H; X═—(CH$_2$)$_3$—

A solution of 2.5 g of the compound from Preparation 1.2 in 60 ml of DMF is cooled to −40° C. under an argon atmosphere, 1.09 g of potassium tert-butoxide are added and the solution is left stirring while allowing the temperature to rise to −15° C. The reaction mixture is cooled to −50° C., a solution of 3.28 g of tert-butyl 4-(3-iodopropyl)piperidine-1-carboxylate (prepared according to J. Med. Chem., 1994, 37(16), 2537-2551) in 40 ml of DMF is added dropwise and the mixture is left stirring for 16 hours while allowing the temperature to rise to 12° C. A saturated NH$_4$Cl solution is added, extraction is carried out with AcOEt, the organic phase is washed with water and dried over Na$_2$SO$_4$, and the solvent is evaporated under vacuum. The residue is chromatographed on silica gel, elution being carried out with the gradient of the cyclohexane/AcOEt mixture from 95/5 (v/v) to 70/30 (v/v). The expected compound is obtained, M.p.=203° C.

$^1$H NMR: d$_6$-DMSO (250 MHz): δ (ppm): 0.73-0.96, mt, 3H, 0.99-1.22, mt, 4H, 1.36, s, 9H, 1.40-1.54, mt, 2H, 1.99-2.17, mt, 1H, 2.18-2.36, mt, 1H, 2.53-2.72, mt, 2H, 3.76-3.95, mt, 5H, 6.64, s, 1H, 6.94, s, 1H, 7.0-7.12, mt, 1H, 7.20-7.40, mt, 2H, 7.58-7.68, mt, 1H, 10.73, mt, 1H.

The enantiomers of the compound thus obtained are separated by chiral phase supercritical fluid chromatography under the following conditions:

Equipment: Berger Prep SFC supercritical fluid chromatography system

Chiral column: Chiralpak IC 5 μm

Mobile phase: CO$_2$/MeOH (65/35; v/v)

Flow rate: 50 ml/minute;

Pressure: 100 bar;

UV detection: 220 nm;

After separation of the enantiomers, the following are obtained:

the dextrorotatory isomer: MH$^+$=517; rt=10.2 min; (M 4) $\alpha_D^{20}$=+53° (c=1; MeOH);

the levorotatory isomer: MH$^+$=517; rt=10.3 min; (M 4) $\alpha_D^{20}$=−48° (c=1; MeOH).

The compounds of formula (II) which are dextrorotatory isomers, which compounds are collated in TABLE IV below, are prepared from an appropriate known compound of formula (VI) and appropriate known compounds of formula (VII) according to the procedure described in Preparation 2.1:

TABLE IV
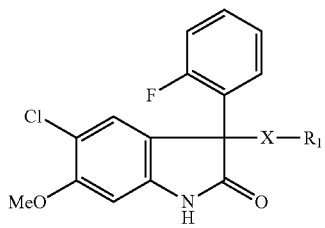
(II): $R_2$ = Cl
$R_3$ = OMe
$R_4$ = F
$R_5$ = H
| Preparation | X | $R_1$ | MH⁺; rt (min) Conditions $\alpha_D^{20}$ (c; solvent) |
|---|---|---|---|
| 2.1.1 | $(CH_2)_2$ | 4-methylpiperidine-N-Boc | 503; 6.1 (M 4) +43° (c = 1, MeOH) |
| 2.1.2 | $CH_2$ | 4-methylpiperidine-N-Boc | 489; 9.47 (M 4) +45° (c = 1, MeOH) |
| 2.1.3 | $CH_2$ | (3R)-3-methylpiperidine-N-Boc | 489; 9.68 (M 4) +86° (c = 0.5, MeOH) |
| 2.1.4 Diastereoisomer 1 | $(CH_2)_3$ | 3-piperidinyl-N-Cbz | 551; 9.70 (M 4) +36° (c = 0.25, MeOH) |
| 2.1.5 Diastereoisomer 2 | $(CH_2)_3$ | 3-piperidinyl-N-Cbz | 551; 9.73 (M 4) +32° (c = 0.25, MeOH) |

Preparation 2.2

5-Chloro-3-(2-chlorophenyl)-3-[4-(dimethylamino)butyl]-6-methoxy-1,3-dihydro-2H-indol-2-one

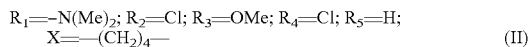

$R_1$=—$N(Me)_2$; $R_2$=Cl; $R_3$=OMe; $R_4$=Cl; $R_5$=H;
$X$=—$(CH_2)_4$—     (II)

A mixture of 0.3 g of the compound from Preparation 2a.1, 8 ml of a 2M solution of dimethylamine in THF, 2 ml of a 40% aqueous dimethylamine solution, 0.5 g of $Na_2CO_3$ and 0.4 g of NaI in 10 ml of acetonitrile is heated at 50° C. for 48 hours in a closed container. The reaction mixture is cooled to 15° C., water is added, extraction is carried out with AcOEt, the organic phase is washed with water and dried over $Na_2SO_4$, and the solvent is evaporated under vacuum. The residue is chromatographed on silica gel, elution being carried out with the gradient of the DCM/MeOH mixture from 100/0 (v/v) to 80/20 (v/v). The expected compound is obtained, M.p.=86° C.

Preparation 2.2.1

5-Chloro-3-phenyl-3-[3-(4-(tert-butyloxycarbonyl)piperazin-1-yl)propyl]-6-methoxy-1,3-dihydro-2H-indol-2-one (II):

$R_1$ = 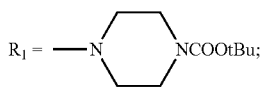 NCOOtBu;

$R_2$=Cl; $R_3$=OMe; $R_4$=H; $R_5$=H; $X$=—$(CH_2)_3$—

5.9 g of 4-(tert-butoxycarbonyl)piperazine, 1.68 g of sodium carbonate and 1.58 g of sodium iodide are added to 3.7 g of the compound from Preparation 2a.9 in 45 ml of DMF. The medium is heated with stirring for 3 hours, cooled, run onto 450 ml of water and extracted with AcOEt. The organic phase is evaporated to dryness and the residue is purified by chromatography on silica, elution being carried out with the gradient of the DCM/MeOH mixture from 100/0 (v/v) to 90/10 (v/v). The expected compound is obtained, M.p.=72° C.

The enantiomers of the compound thus obtained are separated by chiral phase supercritical fluid chromatography under conditions similar to those of Example 1.

The levorotatory enantiomer of compound 2.2.1:

$\alpha_D^{20}$=−75.1° (AcOEt);

$MH^+$=500; rt=5.75 min; (M 4)

and the dextrorotatory enantiomer of compound 2.2.1:

$\alpha_D^{20}$=+70.3° (AcOEt);

$MH^+$=500; rt=5.83 min; (M 4)

are obtained.

The compounds of formula (II), collated in the following Table V, are obtained from appropriate compounds described above of formula (VIII) and appropriate compounds of formula (V) according to the procedure described in Preparation 2.2.1:

TABLE V

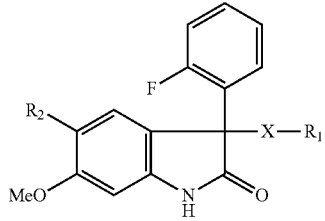

(II): $R_3$ = OMe
$R_4$ = F
$R_5$ = H

| Preparation | Precursor compound (VIII) | $R_2$ | X | $R_1$ | $MH^+$; rt (min) (Conditions) $\alpha_D^{20}$ (c; solvent) |
|---|---|---|---|---|---|
| 2.2.2 | 2a.6 | Br | $(CH_2)_3$ | —N⟨⟩N—COOtBu | 562; 4.42 (M 3) +40° (c = 1, MeOH) |
| 2.2.3 | 2a.13 | Cl | $(CH_2)_4$ | —N⟨⟩ | 431; 5.12 (M 4) +55° (c = 1, MeOH) |

Preparation 2.3

5-Chloro-3-(2-fluorophenyl)-3-[3-(dimethylamino)propyl]-6-methoxy-1,3-dihydro-2H-indol-2-one, single isomer $R_1$=—$N(Me)_2$; $R_2$=Cl; $R_3$=OMe; $R_4$=F; $R_5$=H; X=—$(CH_2)_3$—     (II)

A mixture of 0.59 g of the dextrorotatory compound obtained in Preparation 2a.2, 20 ml of a 2M solution of dimethylamine in THF, 0.5 g of sodium carbonate and 0.4 g of sodium iodide in 10 ml of acetonitrile is heated at 50° C. for 48 hours in a closed container. The reaction mixture is cooled to 15° C., water is added, extraction is carried out with AcOEt, the organic phase is washed with water and dried over $Na_2SO_4$, and the solvent is evaporated under vacuum. The residue is chromatographed on silica gel, elution being carried out with the gradient of the DCM/MeOH mixture from 100/0 (v/v) down to 80/20 (v/v). The expected compound is obtained in the form of a white resin.

$MH^+$=377; rt=5.66 min; (M 1).

$^1$H NMR: $d_6$-DMSO (400 MHz): δ (ppm): 0.88-1.00, mt, 1H, 1.17-1.28, mt, 1H, 2.01, s, 6H, 1.60-1.85, mt, 4H, 3.86, s, 3H, 6.66, s, 1H, 6.94, s, 1H, 7.05-7.40, mt, 3H, 7.60-7.66, mt, 1H, 10.77, s, 1H.

Preparation 2.4

5-Chloro-3-(2-fluorophenyl)-6-methoxy-3-[3-(4-methylpiperazin-1-yl)propyl]-1,3-dihydro-2H-indol-2-one, single isomer (II):

$R_1$ = —N⟨piperazine⟩N-Me;

$R_2$=Cl; $R_3$=OMe; $R_4$=F; $R_5$=H; X=—$(CH_2)_3$—

A mixture of 0.15 g of the dextrorotatory compound obtained in Preparation 2a.2, 0.14 ml of 1-methylpiperazine, 0.05 g of $Na_2CO_3$ and 0.067 g of NaI in 2 ml of DMF is heated at 100° C. for 3 hours. The reaction mixture is cooled to 15° C., water is added, extraction is carried out with AcOEt, the organic phase is washed with water and dried over $Na_2SO_4$, and the solvent is evaporated under vacuum. The residue is chromatographed on silica gel, elution being carried out with the gradient of the DCM/MeOH mixture from 100/0 (v/v) to 70/30 (v/v). The expected compound is obtained.

$^1$H NMR: $d_6$-DMSO (250 MHz): δ (ppm): 0.85-1.07, mt, 1H, 1.13-1.34, mt, 1H, 2.00-2.45, mt, 12H, 2.111, s, 3H, 3.856, s, 3H, 6.651, s, 1H, 6.926, s, 1H, 7.01-7.12, mt, 1H, 7.21-7.40, mt, 2H, 7.56-7.66, mt, 1H, 10.73, s, 1H.

The compounds of formula (II), collated in the following Table VI are obtained from appropriate compounds described above of formula (VIII) and appropriate compounds of formula (V) according to the procedures described in the above Preparations:

TABLE VI (II)

$R_3$ = OMe

| Preparation | $R_2$ | $R_4$ | $R_5$ | X | $R_1$ | $MH^+$; rt (min) Conditions |
|---|---|---|---|---|---|---|
| 2.5 | Cl | F | H | $(CH_2)_3$ | —N⟨pyrrolidine-3-yl⟩N—C(=O)—$CF_3$ | 514; 4.34 (M 3) |
| 2.6 | Cl | F | H | $(CH_2)_3$ | —N⟨pyrrolidine-3-yl⟩N—C(=O)—$CF_3$ | 514; 4.30 (M 3) |
| 2.7 | Cl | F | H | $(CH_2)_3$ | —N⟨piperidine⟩ | 417; 5.89 (M 1) |

TABLE VI-continued
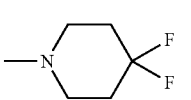
$R_3 = OMe$
| Preparation | $R_2$ | $R_4$ | $R_5$ | X | $R_1$ | MH+; rt (min) Conditions |
|---|---|---|---|---|---|---|
| 2.8 | Cl | F | H | (CH$_2$)$_3$ | 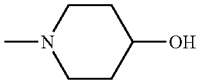 | 453; 4.24 (M 3) |
| 2.9 | Cl | F | H | (CH$_2$)$_3$ | 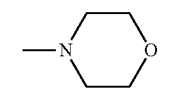 | 433; 4.00 (M 3) |
| 2.10 | Cl | F | H | (CH$_2$)$_3$ | 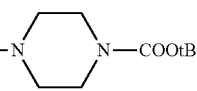 | 419; 5.23 (M 1) |
| 2.11 | Cl | F | H | (CH$_2$)$_3$ | 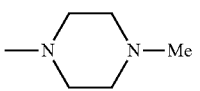 | 518; 6.62 (M 1) |
| 2.12 | Cl | F | H | (CH$_2$)$_3$ | 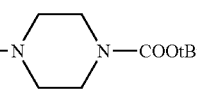 | 432; 5.55 (M 1) |
| 2.13 | Cl | F | H | (CH$_2$)$_3$ | 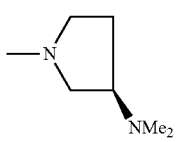 | 518; 6.43 (M 1) |
| 2.14 | Cl | F | H | (CH$_2$)$_3$ | 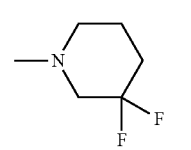 | 446; 4.43 (M 4) |
| 2.15 | Cl | F | H | (CH$_2$)$_3$ | 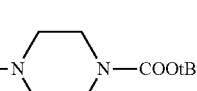 | 453; 4.27 (M 3) |
| 2.16 | Cl | Me | H | (CH$_2$)$_3$ | 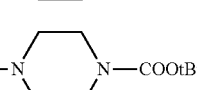 | 514; 5.94 (M 4) |
| 2.17 | Cl | F | 5-F | (CH$_2$)$_3$ | 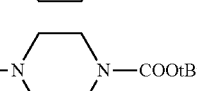 | 536; 4.45 (M 3) |
| 2.18 | Cl | F | 6-F | (CH$_2$)$_3$ | 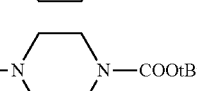 | 536; 5.95 (M 4) |

TABLE VI-continued

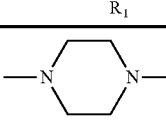

(II)

R$_3$ = OMe

| Prep-aration | R$_2$ | R$_4$ | R$_5$ | X | R$_1$ | MH$^+$; rt (min) Conditions |
|---|---|---|---|---|---|---|
| 2.19 | Cl | F | 3-Cl | (CH$_2$)$_3$ | 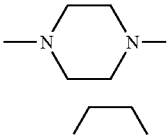 —N⌒N—COOtBu | 552; 4.59 (M 3) |
| 2.20 | Me | F | H | (CH$_2$)$_3$ | —N⌒N—COOtBu | 498; 5.76 (M 4) |
| 2.21 | Me | F | H | (CH$_2$)$_3$ | —N⌒N—Me | 412; 4.70 (M 4) |
| 2.22 | Me | F | H | (CH$_2$)$_3$ | —N(Me)Me | 357; 5.01 (M 4) |
| 2.23 | OMe | F | H | (CH$_2$)$_3$ | —N⌒N—COOtBu | 514; 5.59 (M 4) |
| 2.24 | OMe | F | H | (CH$_2$)$_3$ | —N⌒N—Me | 428; 4.97 (M 4) |
| 2.25 | Cl | F | H | (CH$_2$)$_3$ | —N⌒N—CH$_2$CF$_3$ | 500; 6.16 (M 4) |
| 2.26 | Cl | F | H | (CH$_2$)$_3$ | —N⌒N—iPr | 460; 4.98 (M 4) |
| 2.27 | Cl | F | H | (CH$_2$)$_5$ | —N(Me)Me | 405; 5.90 (M 4) |
| 2.28 | Cl | F | H | (CH$_2$)$_3$ | —N⌒N—Et | 446; 5.45 (M 4) |
| 2.29 | Cl | F | H | (CH$_2$)$_3$ | —N⌒N—Boc (diazepane) | 532; 5.78 (M 4) |
| 2.30 | Cl | F | H | (CH$_2$)$_5$ | —N(piperidine) | 445; 6.12 (M 4) |

TABLE VI-continued

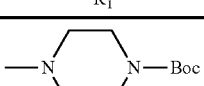

(II)

$R_3 = OMe$

| Preparation | $R_2$ | $R_4$ | $R_5$ | X | $R_1$ | MH+; rt (min) Conditions |
|---|---|---|---|---|---|---|
| 2.31 | Cl | F | H | $(CH_2)_2$ | —N⌒N—Boc | 504; 6.36 (M 4) |
| 2.32 | Cl | F | 5-CO$_2$Me | $(CH_2)_3$ | —N⌒N—Me | 490; 5.60 (M 4) |

Preparation 2.33

5-Chloro-3-[2-fluoro-5-(hydroxymethyl)phenyl]-6-methoxy-3-[3-(4-methyl-piperazin-1-yl)propyl]-1,3-dihydro-2H-indol-2-one, single isomer (II):

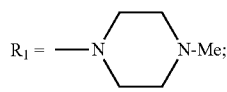

$R_2$=Cl; $R_3$=OMe; $R_4$=F; $R_5$=5-CH$_2$OH; X=—(CH$_2$)$_3$—

1.5 ml of 1M diisobutylaluminum hydride in toluene are added to the solution, cooled to −50° C., of 0.22 g of methyl 3-{5-chloro-6-methoxy-3-[3-(4-methylpiperazin-1-yl)propyl]-2-oxo-2,3-dihydro-1H-indol-3-yl}-4-fluorobenzoate, single isomer, (Preparation 2.32) in 4 ml of DCM. The temperature is allowed to slowly return to 20° C. over 24 hours. The mixture is cooled to −10° C., an aqueous sodium carbonate solution is added, extraction is carried out with DCM, the organic phase is dried over Na$_2$SO$_4$ and the solvent is evaporated under vacuum. The residue is chromatographed on silica gel, elution being carried out with the gradient of the DCM/MeOH mixture from 90/10 (v/v) to 80/20 (v/v). The expected compound is obtained in the resin form.

MH+=462; rt=5.00 min; (M4).

3. Preparations of the compounds of formula (III)

Preparation 3.1

2,4-Dimethoxybenzenesulfonyl chloride $R_6$=—OMe; $R_7$=2-OMe; Hal=Cl.     (III)

This compound is prepared according to J. Am. Chem. Soc., 1952, 74, 2008.

Preparation 3.2

4-Ethoxy-3-methoxybenzenesulfonyl chloride $R_6$=—OEt; $R_7$=3-OMe; Hal=Cl.     (III)

A—1-Ethoxy-2-methoxybenzene 28 g of cesium carbonate and then 25.77 ml of iodoethane are added to a mixture of 10 g of 2-methoxyphenol in 100 ml of DMF and the mixture is heated at 50° C. for 8 hours. 450 ml of water are added to the reaction mixture, extraction is carried out with AcOEt, the organic phase is washed with water and dried over Na$_2$SO$_4$, and the solvent is evaporated under vacuum. The residue is distilled under vacuum and the expected compound is obtained, B.p.=102-105° C. under 24 mbar.

B—4-Ethoxy-3-methoxybenzenesulfonyl chloride 10 g of the compound obtained in the preceding stage are cooled to −10° C., 21.84 ml of chlorosulfonic acid and then 13.68 g of phosphorus pentachloride are added dropwise and the mixture is left stirring at −5° C. for 1 hour. The reaction mixture is run onto 250 ml of ice and water and extracted with DCM, the organic phase is dried over Na$_2$SO$_4$ and the solvent is evaporated under vacuum. The residue is chromatographed on silica gel, elution being carried out with the gradient of the cyclohexane/AcOEt mixture from 95/5 (v/v) to 85/15 (v/v). The expected compound is obtained, M.p.=93° C.

$^1$H NMR: CDCl$_3$ (250 MHz): δ (ppm): 1.55, t, 3H, 3.99, s, 3H, 4.23, q, 2H, 6.97-7.02, mt, 1H, 7.46-7.48, mt, 1H, 7.66-7.71, mt, 1H.

Preparation 3.3

4-(1,1,2,2-Tetrafluoroethoxy)benzenesulfonyl chloride $R_6$=—OCF$_2$CHF$_2$; $R_7$=H; Hal=Cl.     (III)

1.94 g of (1,1,2,2-tetrafluoroethoxy)benzene are added dropwise to 5.83 g of chlorosulfonic acid cooled to 5° C. The reaction mixture is run onto 250 ml of ice and water and extracted with DCM, the organic phase is dried over MgSO$_4$ and the solvent is evaporated under vacuum. The residue is chromatographed on silica gel, elution being carried out with the gradient of the heptane/DCM mixture from 8/2 (v/v) to 1/1 (v/v). The expected compound is obtained.

$^1$H NMR: CDCl$_3$ (300 MHz): δ (ppm): 5.99, t, 1H, 7.49, d, 2H, 8.13, d, 2H.

Preparation 3.4

3-Methoxy-4-(1-methylethoxy)benzenesulfonyl chloride

R$_6$=—OiPr; R$_7$=3-OMe; Hal=Cl.  (III)

A—1-Methoxy-2-(1-methylethoxy)benzene 16.7 g of potassium carbonate and then 12 ml of 2-iodopropane are added to a mixture of 10 g of 2-methoxyphenol (commercial) in 100 ml of acetonitrile and the mixture is heated at reflux for 8 hours. 200 ml of water are added to the reaction mixture, extraction is carried out with AcOEt, the organic phase is washed with a 1N NaOH solution and with a saturated NaCl solution and dried over MgSO$_4$, and the solvent is evaporated under vacuum. The expected compound is obtained in the form of an oil.

B—Sodium 3-methoxy-4-(1-methylethoxy)benzenesulfonate 2.7 ml chlorosulfonic acid are added dropwise to a solution, cooled to 0° C., of 6.6 g of the preceding compound in 25 ml of DCM. The mixture is stirred at 0° C. for 30 minutes and is then run onto 100 ml of ice and water. The organic phase is removed, the aqueous phase is basified with 40% sodium hydroxide solution and the precipitate formed is filtered off.

C—3-Methoxy-4-(1-methylethoxy)benzenesulfonyl chloride 2 drops of DMF and then 3.1 ml of oxalyl chloride are added to a suspension of 3.2 g of the preceding compound in 60 ml of DCM. After stirring at AT for 18 hours, the mixture is concentrated and chromatographed on silica gel, elution being carried out with the gradient of the heptane/iPr$_2$O mixture from 95/5 (v/v) to 7/3 (v/v).

$^1$H NMR: CDCl$_3$ (300 MHz): δ (ppm): 1.30, d, 6H, 3.78, s, 3H, 4.77, mt, 1H, 6.59, d, 1H, 7.24, s, 1H, 7.58, d, 1H.

Preparation 3.5

4-(1-Methylethoxy)-3-(trifluoromethyl)benzenesulfonyl chloride

R$_6$=—OiPr; R$_7$=3-CF$_3$; Hal=Cl.  (III)

The compound is obtained from 2-(trifluoromethyl)phenol by using the procedure of Preparation 3.4.

$^1$H NMR: CDCl$_3$ (300 MHz): δ (ppm): 1.32, d, 6H, 4.59, m, 1H, 7.22, d, 1H, 7.92, d, 1H, 8.12, s, 1H.

Preparation 3.6

4-(3,3-Diethylureido)-3-methylbenzenesulfonyl chloride

A—1,1-Diethyl-3-(o-tolyl)urea 7.75 g of potassium carbonate and 7.1 ml of N,N-diethylcarbamoyl chloride are added to 5 g of o-methylaniline in solution in 25 ml of DMF. The medium is stirred at 60° C. for 4 hours. The medium, cooled to 20° C., is run onto ice and extracted with AcOEt, and the organic phase is washed with 1N hydrochloric acid and then with 0.5N sodium hydroxide solution, dried over Na$_2$SO$_4$ and concentrated under reduced pressure to give the expected product in the solid form.

$^1$H NMR: CDCl$_3$ (300 MHz): δ (ppm): 1.11, t, 6H, 2.17, s, 3H, 3.33, q, 4H, 6.96-7.23, m, 4H, 7.66, s, 1H.

B—4-(3,3-Diethylureido)-3-methyl-benzenesulfonyl chloride 6.6 g of 1,1-diethyl-3-(o-tolyl)urea (prepared in A) are added to 42.5 ml of chlorosulfonic acid cooled to 0° C. After stirring for 2 hours at a temperature in the region of 5° C., the mixture is run onto ice and extracted with AcOEt, and the organic phase is dried over Na$_2$SO$_4$ and concentrated under reduced pressure. The residue is washed with a DCM/pentane mixture to give, after drying at 40° C., the expected compound in the solid form.

$^1$H NMR: d$_6$-DMSO (250 MHz): δ (ppm): 1.17, t, 6H, 2.17, s, 3H, 3.32, q, 4H, 6.42, s, 1H, 7.67-7.79, m, 2H, 8.26, d, 1H.

Preparation 3.7

4-(3,3-Diethylureido)-3-fluorobenzenesulfonyl chloride

A—1,1-Diethyl-3-(2-fluorophenyl)urea 7.46 g of potassium carbonate and 6.84 ml of N,N-diethylcarbamoyl chloride are added to 5 g of o-fluoroaniline in solution in 25 ml of DMF. The medium is stirred at 60° C. for 2 hours. The medium, cooled to 20° C., is run onto ice and extracted with ethyl acetate, and the organic phase is washed with 1N hydrochloric acid and then with 0.5N sodium hydroxide solution, dried over sodium sulfate and concentrated under reduced pressure to give the expected compound in the solid form.

$^1$H NMR: d$_6$-DMSO (400 MHz): δ (ppm): 1.1: t, 6H, 3.33, q, 4H, 7.06-7.12, m, 1H, 7.13-7.20, m, 1H, 7.41-7.49, m, 1H, 7.49, s, 1H.

B—4-(3,3-Diethylureido)-3-fluorobenzenesulfonyl chloride 1 g of 1,1-diethyl-3-(2-fluorophenyl)urea (prepared in A) is added to 9.5 ml of chlorosulfonic acid cooled to 0° C. After stirring for 4 hours at a temperature in the region of 15° C., the mixture is run onto ice and extracted with AcOEt, and the organic phase is dried over Na$_2$SO$_4$ and concentrated under reduced pressure. The residue is washed with a DCM/pentane mixture to give, after drying at 40° C., the expected compound in the solid form.

$^1$H NMR: d$_6$-DMSO (250 MHz): δ (ppm): 1.16, t, 6H, 3.31, q, 4H, 6.80, d, 1H, 7.60-7.74, m, 2H, 8.47, q, 1H.

The compounds of formula (III) collated in TABLE VII below are prepared according to the procedures described in the above Preparations:

TABLE VII

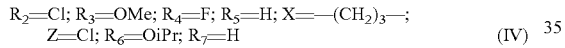

(III)

| Preparations | $R_6$ | $R_7$ | Hal |
|---|---|---|---|
| 3.8 | —OiPr | H | Cl |
| 3.9 | —OMe | 3-OMe | Cl |
| 3.10 | —Me | 3-Me | Cl |
| 3.11 | —OMe | 3-Me | Cl |
| 3.12 | —OEt | H | Cl |
| 3.13 | —OEt | 3-Me | Cl |
| 3.14 | —OCHF$_2$ | H | Cl |
| 3.15 | —OCF$_3$ | H | Cl |

4. Preparations of the compounds of formula (IV)

Preparation 4.1

5-Chloro-3-(3-chloropropyl)-3-(2-fluorophenyl)-6-methoxy-1-{[4-(1-methyl-ethoxy)phenyl]sulfonyl}-1,3-dihydro-2H-indol-2-one, single isomer $R_2$=Cl; $R_3$=OMe; $R_4$=F; $R_5$=H; X=—(CH$_2$)$_3$—; Z=Cl; $R_6$=OiPr; $R_7$=H         (IV)

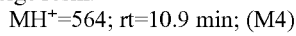

3.7 g of potassium tert-butoxide and then 7.7 g of 4-(1-methylethoxy)-benzenesulfonyl chloride (commercial) are added to a solution of 11 g of the dextrorotatory isomer resulting from Preparation 2a.2 in 100 ml of THF at AT and the mixture is left stirring for 3 hours. 200 ml of 10% aqueous ammonium chloride solution are added, extraction is carried out with AcOEt, the organic phase is dried over MgSO$_4$ and the solvent is evaporated under vacuum. The residue is chromatographed on silica gel, elution being carried out with the gradient of the heptane/AcOEt mixture from 99/1 (v/v) to 1/1 (v/v). The expected compound is obtained in the form of a beige resin.
MH$^+$=564; rt=10.9 min; (M4)

Preparation 4.2

1-[(4-(tert-Butoxy)phenyl)sulfonyl]-5-chloro-3-(3-chloropropyl)-3-(2-fluoro-phenyl)-6-methoxy-1,3-dihydro-2H-indol-2-one, single isomer $R_2$=Cl; $R_3$=OMe; $R_4$=F; $R_5$=H; X=—(CH$_2$)$_3$—; Z=Cl; $R_6$=OtBu; $R_7$=H         (IV)

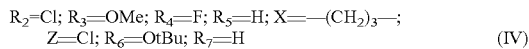

A—1-{[4-(Benzyloxy)phenyl]sulfonyl}-5-chloro-3-(3-chloropropyl)-3-(2-fluorophenyl)-6-methoxy-1,3-dihydro-2H-indol-2-one The compound is obtained from 4-(benzyloxy)benzenesulfonyl (commercial) by using the procedure of Preparation 4.1.
MH$^+$=614; rt=6.93 min; (M3)

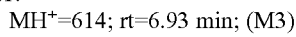

B—5-Chloro-3-(3-chloropropyl)-3-(2-fluorophenyl)-1-[(4-hydroxyphenyl)-sulfonyl]-6-methoxy-1,3-dihydro-2H-indol-2-one 122 mg of 10% palladium-on-charcoal and then 189 mg of ammonium formate are added to a solution of 0.61 g of the preceding compound in 40 ml of THF/MeOH (1/1). After stirring for 1 hour at AT, the reaction mixture is filtered through talc and the filtrate is concentrated under vacuum. The residue is taken up in AcOEt and the solution is washed with a 10% ammonium chloride and with a saturated NaCl solution, dried over MgSO$_4$ and concentrated under vacuum. The residue is chromatographed on silica gel, elution being carried out with the gradient of the heptane/AcOEt mixture from 4/1 (v/v) to 2/3 (v/v). The expected compound is obtained in the form of a beige resin.
MH$^+$=524; rt=6.02 min; (M4)

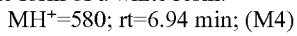

C—1-[(4-(tert-Butoxy)phenyl)sulfonyl]-5-chloro-3-(3-chloropropyl)-3-(2-fluorophenyl)-6-methoxy-1,3-dihydro-2H-indol-2-one The expected compound is obtained by using the method described in J. Org. Chem., 2006, 71, 9580.

85 mg of scandium triflate and then 2.65 g of di(tert-butyl) dicarbonate are added to a suspension of 1.82 g of the preceding compound in 15 ml of DCM. After stirring at AT for 18 hours, the mixture is concentrated under vacuum and the residue is chromatographed on silica gel, elution being carried out with the gradient of the heptane/DCM mixture from 1/1 (v/v) to 1/9 (v/v). The expected compound is obtained in the form of a white resin.
MH$^+$=580; rt=6.94 min; (M4)

Example 1

Compound No. 1 and Compound No. 2

5-Chloro-1-[(2,4-dimethoxyphenyl)sulfonyl]-3-(2-fluorophenyl)-6-methoxy-3-(3-(piperidin-4-yl)propyl)-1,3-dihydro-2H-indol-2-one hydrochloride, dextrorotatory isomer and levorotatory isomer A—tert-Butyl 4-[3-[5-chloro-1-[(2,4-dimethoxyphenyl)sulfonyl]-3-(2-fluoro-phenyl)-6-methoxy-2-oxo-2,3-dihydro-1H-indol-3-yl]propyl]piperidin-1-carboxylate A solution of 0.28 g of the compound from Preparation 2.1 in 10 ml of THF is cooled to −30° C., 0.073 g of potassium tert-butoxide is added and the mixture is left stirring while allowing the temperature to rise to 0° C. The reaction mixture is cooled to −60° C., 0.147 g of the compound from Preparation 3.1 is added and the mixture is left stirring at 20° C. overnight. The reaction mixture is hydrolyzed by addition of water, extraction is carried out with AcOEt, the organic phase is dried over Na$_2$SO$_4$ and the solvent is evaporated under vacuum. The expected compound is obtained.

B—5-Chloro-1-[(2,4-dimethoxyphenyl)sulfonyl]-3-(2-fluorophenyl)-6-methoxy-3-(3-piperidin-4-ylpropyl)-1,3-dihydro-2H-indol-2-one hydrochloride, dextrorotatory isomer and levorotatory isomer The compound from the preceding stage is taken up in a 2N hydrochloric ether solution and left stirring at 20° C. for 16 hours. The precipitated formed is filtered off and the expected compound is obtained in the racemic form, M.p.=155° C.

The enantiomers of the compound thus obtained are separated by chiral phase supercritical fluid chromatography under the following conditions:
Equipment: Mettler Toledo APS1010 SFC System;
Chiral column: Chiralpak AD-H;
Mobile phase: $CO_2$/(MeOH+0.5% propan-2-ylamine): (70/30; v/v);
Flow rate: 50 ml/minute;
Pressure/Temperature: 100 bar/40° C.;
UV detection: 220 nm.

The two enantiomers are obtained, respectively taken up in a 2N hydrochloric ether solution to give:
Compound No. 1: dextrorotatory isomer: M.p.=163° C.; $\alpha_D^{20}$=+105.7° (c=1; MeOH);
$^1$H NMR: $d_6$-DMSO (250 MHz): δ (ppm): 0.61-0.85, mt, 2H, 0.98-1.20, mt, 4H, 1.26-1.56, mt, 3H, 1.99-2.15, mt, 1H, 2.26-2.42, mt, 1H, 2.67-2.86, mt, 2H; 3.10-3.22, mt, 2H, 3.65, s, 3H, 3.88, s, 3H, 3.93, s, 3H, 6.72-6.79, mt, 2H, 6.99-7.1, mt, 2H, 7.104, s, 1H, 7.23-7.43, mt, 2H, 7.59-7.69, mt, 2H, 7.88-7.94, mt, 1H, 8.43, mt, 2H.

Compound No. 2: levorotatory isomer: M.p.=175° C.; $\alpha_D^{20}$=-104.5° (c=1; MeOH);
$^1$H NMR: $d_6$-DMSO (250 MHz): δ (ppm): 0.61-0.85, mt, 2H, 0.99-1.19, mt, 4H, 1.27-1.57, mt, 3H, 1.99-2.16, mt, 1H, 2.26-2.85, mt, 2H, 3.10-3.22, mt, 2H, 3.65, s, 3H, 3.88, s, 3H, 6.72-6.79, mt, 2H, 6.99-7.1, mt, 1H, 7.104, s, 1H, 7.23-7.43, mt, 2H, 7.59-7.69, mt, 2H, 7.88-7.94, mt, 1H, 8.43, mt, 2H.

Example 2

Compound No. 3

5-Chloro-3-[3-(dimethylamino)propyl]-3-(2-fluorophenyl)-1-[(4-isopropoxy-phenyl)sulfonyl]-6-methoxy-1,3-dihydro-2H-indol-2-one hydrochloride, dextrorotatory isomer A solution of 0.17 g of the compound from Preparation 2.3 in 2 ml of THF is cooled to −30° C., 0.54 ml of 1M potassium tert-butoxide in solution in THF is added and the mixture is left stirring while allowing the temperature to rise to 0° C. The reaction mixture is cooled to −60° C., 0.127 g of 4-isopropoxybenzenesulfonyl chloride is added and the mixture is left stirring at 20° C. overnight. The reaction mixture is hydrolyzed by addition of water, extraction is carried out with AcOEt, the organic phase is dried over $Na_2SO_4$ and the solvent is evaporated under vacuum. The residue is chromatographed on silica gel, elution being carried out with the gradient of the DCM/MeOH mixture from 100/0 (v/v) to 90/10 (v/v). The expected product is obtained in the form of a white resin, M.p.=173° C.
$\alpha_D^{20}$=+88.1° (c=1; AcOEt).

Example 3

Compound No. 4

3-[3-[(3R)-Aminopyrrolidin-1-yl]propyl]-5-chloro-3-(2-fluorophenyl)-1-[(4-isopropoxyphenyl)sulfonyl]-6-methoxy-1,3-dihydroindol-2-one hydrochloride, dextrorotatory isomer A solution of 0.177 g of the compound from Preparation 2.5 in 3 ml of THF is cooled to −30° C., 0.48 ml of a 1M solution of potassium tert-butoxide in THF is added and the mixture is left stirring while allowing the temperature to rise to 0° C. The reaction mixture is cooled to −60° C., 0.112 g of 4-isopropoxybenzenesulfonyl chloride is added and the mixture is left stirring at 20° C. overnight. The reaction mixture is hydrolyzed by addition of water, extraction is carried out with AcOEt, the organic phase is dried over $Na_2SO_4$ and the solvent is evaporated under vacuum. The residue is chromatographed on silica gel, elution being carried out with the gradient of the DCM/MeOH mixture from 100/0 (v/v) to 98/2 (v/v). N-[(1R)-[3-[5-Chloro-3-(2-fluorophenyl)-1-[(4-isopropoxyphenyl)sulfonyl]-6-methoxy-2-oxo-2,3-dihydro-1H-indol-3-yl]propyl]pyrrolidin-3-yl]-2,2,2-trifluoroacetamide is obtained. The compound thus obtained is taken up in a 12N solution of HCl in ethanol, heating is carried out at 80° C. for 2 hours and the mixture is concentrated under vacuum. The residue is taken up in a hydrochloric ether solution and the precipitate formed is filtered off. The expected compound is obtained, M.p.=215° C.
$\alpha_D^{20}$=+122° (c=1; MeOH).

Example 4

Compound No. 13

5-Chloro-3-(2-fluorophenyl)-1-[(4-isopropoxyphenyl)sulfonyl]-6-methoxy-3-[3-(4-methylpiperazin-1-yl)propyl]-1,3-dihydroindol-2-one hydrochloride, dextrorotatory isomer A solution of 0.128 g of the compound from Preparation 2.4 in 2 ml of THF is cooled to −30° C., 0.066 g of potassium tert-butoxide is added and the mixture is left stirring while allowing the temperature to rise to 0° C. The reaction mixture is cooled to −30° C., 0.09 g of 4-isopropoxybenzenesulfonyl chloride is added and the mixture is left stirring at 10° C. overnight. The reaction mixture is hydrolyzed by addition of water, extraction is carried out with AcOEt, the organic phase is dried over $Na_2SO_4$ and the solvent is evaporated under vacuum. The residue is chromatographed on silica gel, elution being carried out with the DCM/MeOH mixture. The product thus obtained is taken up in 2N hydrochloric ether and the precipitate formed is filtered off and dried. The expected compound is obtained, M.p.=205° C. MH$^+$=630; rt=7.09 min (M1).
$\alpha_D^{20}$=+114.8° (c=1; MeOH).
$^1$H NMR: $d_6$-DMSO (400 MHz): δ (ppm): 1.24-1.38, mt, 8H, 2.18-2.30, mt, 1H, 2.35-2.46, mt, 1H, 2.782, s, 3H, 2.95-3.89, mt, 10H, 3.986, s, 3H, 4.76-4.84, mt, 1H, 6.909, q, 1H, 7.105, s, 1H, 7.171, d, 2H, 7.23-7.30, mt, 1H, 7.32-7.41, mt, 1H, 7.62-7.70, mt, 2H, 8.014, d, 2H, 10.72-11.96, mt, 2H.

Example 5

Compound No. 14

5-Chloro-[(4-ethoxy-3-methoxyphenyl)sulfonyl]-3-(2-fluorophenyl)-6-methoxy-3-[3-(4-methylpiperazin-1-yl)propyl]-1,3-dihydro-indol-2-one hydrochloride, dextrorotatory isomer A solution of 0.128 g of the compound from Preparation 2.4 in 2 ml of THF is cooled to −30° C., 0.066 g of potassium tert-butoxide is added and the mixture is left stirring while allowing the temperature to rise to 0° C. The reaction mixture is cooled to −30° C., 0.097 g of 4-ethoxy-3-methoxybenzenesulfonyl chloride (described in Chem. Ber., 1906, 39, 2777) is added and the mixture is left stirring at 10° C. overnight.

The reaction mixture is hydrolyzed by addition of water, extraction is carried out with AcOEt, the organic phase is dried over $Na_2SO_4$ and the solvent is evaporated under vacuum. The residue is chromatographed on silica gel, elution being carried out with the DCM/MeOH mixture. The product thus obtained is taken up in 2N hydrochloric ether and the precipitate formed is filtered off and dried. The expected compound is obtained, M.p.=180° C.

$\alpha_D^{20}$=+106.2° (c=1; MeOH).

$MH^+$=646; rt=6.76 min (M1).

$^1$H NMR: $d_6$-DMSO (400 MHz): δ (ppm): 1.15-1.34, mt, 2H, 1.369, t, 3H, 2.18-2.31, mt, 1H, 2.34-2.45, mt, 1H, 2.788, s, 3H, 2.93-3.34, mt, 2H, 3.42-3.77, mt, 8H, 3.798, s, 3H, 3.978, s, 3H, 4.16, q, 2H, 6.986, q, 1H, 7.111, s, 1H, 7.19-7.24, mt, 1H, 7.25-7.31, mt, 1H, 7.33-7.41, mt, 1H, 7.491, d, 1H; 7.681, t, 1H, 7.742, q, 1H, 10.96-11.9, mt, 2H.

Example 6

Compound No. 17

5-Chloro-3-(2-fluorophenyl)-1-[(4-isopropoxyphenyl)sulfonyl]-6-methoxy-3-[3-(piperazin-1-yl)propyl]-1,3-dihydroindol-2-one hydrochloride, dextrorotatory isomer A—tert-Butyl 4-[3-[5-chloro-3-(2-fluorophenyl)-1-[(4-isopropoxyphenyl)-sulfonyl]-6-methoxy-2-oxo-2,3-dihydro-1H-indol-3-yl]propyl]piperazine-1-carboxylate A solution of 0.2 g of the compound from Preparation 2.11 in 3 ml of THF is cooled to −30° C., 0.086 g of potassium tert-butoxide is added and the mixture is left stirring while allowing the temperature to rise to 0° C. The reaction mixture is cooled to −30° C., 0.107 g of 4-isopropoxybenzenesulfonyl chloride (commercial) is added and the mixture is left stirring at 10° C. overnight. The reaction mixture is hydrolyzed by addition of water, extraction is carried out with AcOEt, the organic phase phase is dried over $Na_2SO_4$ and the solvent is evaporated under vacuum. The residue is chromatographed on silica gel, elution being carried out with the DCM/MeOH mixture, and the expected compound is obtained in the resin form.

B—5-Chloro-3-(2-fluorophenyl)-1-[(4-isopropoxyphenyl)sulfonyl]-6-methoxy-3-[3-(piperazin-1-yl)propyl]-1,3-dihydroindol-2-one hydrochloride, dextrorotatory isomer The expected compound of the preceding stage is dissolved in the minimum of DCM, 2N hydrochloric ether is added, the mixture is left stirring at 20° C. for 16 hours and the precipitate formed is filtered off and dried. The expected compound is obtained, M.p.=232° C.

$\alpha_D^{20}$=+120.8° (c=1; MeOH), $MH^+$=616; rt=6.51 min; (M1).

$^1$H NMR: $d_6$-DMSO (400 MHz): δ (ppm): 1.15-1.39, mt, 8H, 2.17-2.26, mt, 1H, 2.35-2.52, mt, 1H, 3.03-3.75, mt, 10H, 3.99, s, 3H, 4.75-4.85, mt, 1H, 6.91, q, 1H, 7.109, s, 1H, 7.15-7.41, mt, 4H, 7.63-7.72, mt, 2H, 7.95-8.06, mt, 2H, 9.4-9.8, mt, 2H, 11.1-11.5, mt, 1H.

Example 7

Compound No. 55

5-Chloro-3-(2-fluorophenyl)-6-methoxy-3-[3-(4-methyl-1,4-diazepan-1-yl)-propyl]-1-{[4-(1-methylethoxy)phenyl]sulfonyl}-1,3-dihydro-2H-indol-2-one, dextrorotatory isomer A—tert-Butyl 4-{3-[5-chloro-3-(2-fluorophenyl)-6-methoxy-1-{[4-(1-methyl-ethoxy)phenyl]sulfonyl}-2-oxo-2,3-dihydro-1H-indol-3-yl]propyl}-1,4-diazepane-1-carboxylate 106 mg of tert-butyl 1,4-diazepane-1-carboxylate, 61 mg of potassium carbonate and 37 mg of potassium iodide are added to a solution of 250 mg of the single isomer resulting from Preparation 4.1 in 3 ml of acetonitrile and then the mixture is brought to 120° for 30 min under microwave radiation (CEM Discover) in a closed tube. The mixture is filtered and then the filtrate is concentrated. The residue is chromatographed on silica gel, elution being carried out with the gradient of the DCM/MeOH mixture from 100/0 (v/v) to 95/5 (v/v), and the expected compound is obtained in the resin form.

$MH^+$=730; rt=7.90 min; (M4).

B—5-Chloro-3-[3-(1,4-diazepan-1-yl)propyl]-3-(2-fluorophenyl)-6-methoxy-1-{[4-(1-methylethoxy)phenyl]sulfonyl}-1,3-dihydro-2H-indol-2-one hydrochloride 285 mg of the preceding compound are dissolved in the minimum of DCM, 2 ml of 2N hydrochloric ether are added, the mixture is left stirring at 20° C. for 16 hours and diluted with 20 ml of ether, and the precipitate formed is filtered off and dried.

$MH^+$=630; rt=6.24 min; (M4).

C—5-Chloro-3-(2-fluorophenyl)-6-methoxy-3-[3-(4-methyl-1,4-diazepan-1-yl)propyl]-1-{[4-(1-methyl-ethoxy)phenyl]sulfonyl}-1,3-dihydro-2H-indol-2-one hydrochloride 33 μl of a 40% aqueous formaldehyde solution and 123 mg of sodium triacetoxyborohydride are added to a solution of 280 mg of the preceding compound in the minimum of DCM and then the mixture is stirred at AT for 4 hours. The reaction mixture is hydrolyzed by addition of a 10% aqueous sodium bicarbonate solution, extraction is carried out with AcOEt, the organic phase is dried over $MgSO_4$ and the solvent is evaporated under vacuum. The residue is chromatographed on silica gel, elution being carried out with the gradient of the DCM/MeOH mixture from 100/0 (v/v) to 90/10 (v/v), and the expected compound is obtained in its basic form. The latter is taken up in 3 ml of DCM, 2N hydrochloric ether is then added, the mixture is then diluted with 20 ml of ether and the precipitate formed is filtered off and dried. $MH^+$=644; rt=6.32 min; (M4).

Example 8

Compound No. 72

1-[(4-tert-Butoxyphenyl)sulfonyl]-5-chloro-3-(2-fluorophenyl)-6-methoxy-3-(3-(piperazin-1-yl)propyl)-1,3-dihydro-2H-indol-2-one, dextrorotatory isomer A—Benzyl 4-(3-{1-[(4-tert-butoxyphenyl)sulfonyl]-5-chloro-3-(2-fluorophenyl)-6-methoxy-2-oxo-2,3-dihydro-1H-indol-3-yl}propyl)piperazine-1-carboxylate 71 μl of benzyl piperazine-1-carboxylate, 42 mg of potassium carbonate and 50 mg of potassium iodide are added to a solution of 171 mg of the single isomer resulting from Preparation 4.2 in 3 ml of acetonitrile and then the mixture is brought to 120° for 1 hour under microwave radiation (CEM Discover) in a closed tube. The mixture is filtered and then the filtrate is concentrated. The residue is chromatographed on silica gel, elution being carried out with the gradient of the heptane/AcOEt mixture from 4/1 (v/v) to 1/1 (v/v). The expected compound is obtained in the form of a white resin.
MH$^+$=764; rt=5.51 min; (M3).

B—1-[(4-tert-Butoxyphenyl)sulfonyl]-5-chloro-3-(2-fluorophenyl)-6-methoxy-3-(3-piperazin-1-ylpropyl)-1,3-dihydro-2H-indol-2-one 50 mg of 10% palladium-on-charcoal and then 66 mg of ammonium formate are added to a solution of 200 mg of the preceding compound in 10 ml of THF/MeOH (1/1). After stirring at AT for 1 hour, the reaction mixture is filtered through talc and the filtrate is concentrated under vacuum. The residue is taken up in AcOEt and the solution is washed with a 10% ammonium chloride solution and with aqueous sodium chloride solution, dried over MgSO$_4$ and concentrated under vacuum. The residue is chromatographed on silica gel, elution being carried out with the gradient of the DCM/MeOH mixture from 100/0 (v/v) to 90/10 (v/v). The expected compound is obtained in the form of a white precipitate.
MH$^+$=630; rt=6.79 min; (M4).

Example 9

Compound No. 59

5-Chloro-3-(2-fluorophenyl)-6-methoxy-3-[3-(4-methylpiperazin-1-yl)propyl]-1-{[4-(1,1,2,2-tetrafluoroethoxy)phenyl]sulfonyl}-1,3-dihydro-2H-indol-2-one hydrochloride, dextrorotatory isomer 29 μl of a 40% aqueous formaldehyde solution and 104 mg of sodium triacetoxyborohydride are added to a solution of 236 mg of Compound No. 58 in 5 ml of DCM and then the mixture is stirred at AT for 2 hours. The reaction mixture is hydrolyzed by addition of a 10% aqueous sodium bicarbonate solution, extraction is carried out with AcOEt, the organic phase is dried over MgSO$_4$ and the solvent is evaporated under vacuum. The residue is taken up in 3 ml of DCM, then 0.5 ml of 2N hydrochloric ether is added, dilution is then carried out with 20 ml of ether and the precipitate formed is filtered off and dried.
The expected compound is obtained.
M.p.=164° C.; MH$^+$=688; rt=7.11 min; (M4).
$\alpha_D^{20}$=+148° (c=1; MeOH).
$^1$H NMR: d$_6$-DMSO (400 MHz): δ (ppm): 1.35, m, 2H, 2.23-2.33, mt, 1H, 2.46-2.51, mt, 1H, 2.79, s, 3H, 2.90-3.90, mt, 10H, 4.01, s, 3H, 6.74-6.86, mt, 1H, 6.89-7.17, mt, 1H, 7.22-7.30, mt, 1H, 7.31-7.39, mt, 1H, 7.60-7.75, mt, 4H, 8.21-8.29, mt, 2H, 11.2-12.2, m, 2H.

Example 10

Compound No. 63

5-Chloro-1-{[3-fluoro-4-(1-methylethoxy)phenyl]sulfonyl}-3-(2-fluorophenyl)-6-methoxy-3-[3-(4-methylpiperazin-1-yl)propyl]-1,3-dihydro-2H-indol-2-one hydrochloride, dextrorotatory isomer 18 μl of a 40% aqueous formaldehyde solution and 65 mg of sodium triacetoxyborohydride are added to a solution of 139 mg of Compound No. 62 in 5 ml of DCM and then the mixture is stirred at AT for 2 hours. The reaction mixture is hydrolyzed by addition of a 10% aqueous sodium bicarbonate solution, extraction is carried out with AcOEt, the organic phase is dried over MgSO$_4$ and the solvent is evaporated under vacuum. The residue is taken up in 3 ml of DCM, 0.5 ml of 2N hydrochloric ether is then added, dilution is then carried out with 20 ml of ether and the precipitate formed is filtered off and dried.
The expected compound is obtained.
M.p.=188° C.; MH$^+$=648; rt=6.68 min; (M4).
$\alpha_D^{20}$=+145° (c=1; MeOH).
$^1$H NMR: d$_6$-DMSO (400 MHz): δ (ppm): 1.12-1.52, mt, 8H, 2.21-2.34, mt, 1H, 2.36-2.51, mt, 1H, 2.79, s, 3H, 2.88-3.90, mt, 10H, 4.00, s, 3H, 4.82-4.94, mt, 1H, 6.86-6.95, mt, 1H, 7.14, s, 1H, 7.24-7.31, mt, 1H, 7.32-7.41, mt, 1H, 7.46-7.53, mt, 1H, 7.62-7.75, mt, 2H, 7.79-8.0, mt, 2H, 11.1-12.1, m, 2H.

Example 11

Compound No. 118

3-(2-Fluorophenyl)-1-[(4-isopropoxyphenyl)sulfonyl]-6-methoxy-5-methyl-3-[3-(4-methylpiperazin-1-yl)propyl]-1,3-dihydroindol-2-one, dextrorotatory isomer A solution of 0.135 g of the compound from Preparation 2.29 in 3.3 ml of THF is cooled to 0° C., 0.041 g of potassium tert-butoxide and then 0.085 g of 4-isopropoxybenzenesulfonyl chloride are added and the mixture is left stirring at 20° C. for 3 hours. The reaction mixture is hydrolyzed by addition of water, extraction is carried out with AcOEt, the organic phase is dried over Na$_2$SO$_4$ and the solvent is evaporated under vacuum. The residue is chromatographed on silica gel, elution being carried out with the DCM/MeOH mixture. The expected compound is obtained in the form of a white resin.
M.p.=70° C.; MH$^+$=610; rt=13.23 min; (M5).
$\alpha_D^{20}$=+69.6° (c=0.54; AcOEt).
$^1$H NMR: d$_6$-DMSO (400 MHz): δ (ppm): 0.55-0.65, m, 2H, 1.30, d, 6H, 2.00-2.40, m, 18H, 3.90, s, 3H, 4.71-4.78, mt, 1H, 6.23, s, 1H, 6.96-7.16, mt, 3H, 7.24-7.63, mt, 4H, 7.96-7.98, mt, 2H

Example 12

Compound No. 119

5-Fluoro-3-(2-fluorophenyl)-1-[(4-isopropoxyphenyl)sulfonyl]-6-methoxy-3-[3-(4-methylpiperazin-1-yl)propyl]-1,3-dihydroindol-2-one, dextrorotatory isomer 30 μl of a 40% aqueous formaldehyde solution and 20 μl of acetic acid are added to a solution, cooled to 0° C., of 203 mg of Compound No. 115 in 3 ml of the DCM/MeOH (66/34, v/v) mixture. After stirring at 0° C. for 10 min, 192 mg of sodium triacetoxyborohydride are added. The mixture is stirred at RT overnight. The reaction mixture is hydrolyzed by addition of a 10% aqueous sodium bicarbonate solution, extraction is carried out with AcOEt, the organic phase is dried over MgSO$_4$ and the solvent is evaporated under vacuum. The residue is chromatographed on silica gel, elution being carried out with the DCM/MeOH mixture. The expected compound is obtained in the form of the white resin.
M.p.=72° C.; MH$^+$=614; rt=6.94 min; (M4).
$\alpha_D^{20}$=+74° (c=0.53; AcOEt).
$^1$H NMR: d$_6$-DMSO (400 MHz): δ (ppm): 0.51-0.68, m, 2H, 1.30, d, 6H, 1.91-2.31, m, 15H, 3.96, s, 3H, 4.71-4.80, mt, 1H, 6.95-8.00, mt, 10H

Example 13

Compound No. 136

3-[4-({3-[3-(Dimethylamino)propyl]-3-(2-fluorophenyl)-6-methoxy-5-methyl-2-oxo-2,3-dihydro-1H-indol-1-yl}sulfonyl)-2-fluorophenyl]-1,1-diethylurea, dextrorotatory isomer A solution of 0.17 g of the compound from Preparation 2.30 in 5 ml of THF is cooled to 0° C., 0.059 g of potassium tert-butoxide and then 0.162 g of 4-(3,3-diethylureido)-3-fluorobenzenesulfonyl chloride are added and the mixture is left stirring overnight at 20° C. The reaction mixture is hydrolyzed by addition of water, extraction is carried out with AcOEt, the organic phase is dried over $Na_2SO_4$ and the solvent is evaporated under vacuum. The residue is chromatographed on silica gel, elution being carried out with the DCM/MeOH mixture. The expected compound is obtained in the form of a white resin.

M.p.=82° C.; $MH^+$=629; rt=6.87 min; (M4).

$\alpha_D^{20}$=+86.9° (c=0.52; AcOEt).

$^1H$ NMR: $d_6$-DMSO (400 MHz): δ (ppm): 0.65-0.70, m, 2H, 1.10, t, 6H, 1.89, s, 6H, 2.04, s, 3H, 2.11-2.23, mt, 4H, 3.34-3.39, mt, 4H, 3.91, s, 3H; 6.74, s, 1H, 6.96-7.36, mt, 3H, 7.50, s, 1H, 7.61-7.96, 4H, 8.35, s, 1H.

The chemical structures and the physical properties of a few examples of compounds according to the invention, obtained by following the procedures described in the above Examples, are illustrated in the following tables.

In these tables:

Me, Et, iPr, Bu and tBu respectively represent methyl, ethyl, isopropyl, n-butyl and tert-butyl groups.

TABLE VIII (I):

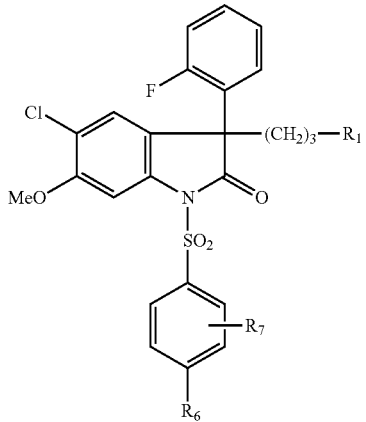

$R_2$ = Cl
$R_3$ = OMe
$R_4$ = F
$R_5$ = H
X = $(CH_2)_3$

| Compound No. | $R_1$ | $R_6$ | $R_7$ | Salt/Base $\alpha_D^{20}$ (c; solvent) | M.p. ° C. $MH^+$; rt (Conditions) |
|---|---|---|---|---|---|
| 1 | ![piperidine]—⟨NH⟩ | —OMe | 2-OMe | HCl +105.7° (c = 1; MeOH) | 163° C. 617; 6.42 (M1) |
| 2 | ![piperidine]—⟨NH⟩ | —OMe | 2-OMe | HCl −104.5° (c = 1; MeOH) | 175° C. 617; 6.42 (M1) |
| 3 | —N(Me)$_2$ | —OiPr | H | HCl +88.1° (c = 1; AcOEt) | 173° C. 575; 9.58 (M2) |
| 4 | ![pyrrolidine-NH2] | —OiPr | H | HCl +122° (c = 1; MeOH) | 215° C. 616; 5.98 (M2) |

TABLE VIII-continued (I):

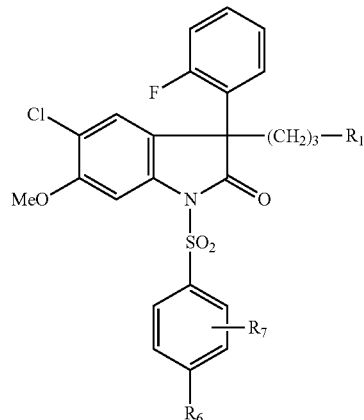

$R_2 = Cl$
$R_3 = OMe$
$R_4 = F$
$R_5 = H$
$X = (CH_2)_3$

| Compound No. | $R_1$ | $R_6$ | $R_7$ | Salt/Base $\alpha_D^{20}$ (c; solvent) | M.p. °C. MH+; rt (Conditions) |
|---|---|---|---|---|---|
| 5 | ![pyrrolidine-NH2] | —OiPr | H | HCl +116.3° (c = 1; MeOH) | 206° C. 616; 6.24 (M4) |
| 6 | ![pyrrolidine-NH2] | —OEt | 3-OMe | HCl +120.2° (c = 1; MeOH) | 210° C. 632; 8.50 (M2) |
| 7 | ![pyrrolidine-NH2] | —OEt | 3-OMe | HCl +110.2° (c = 1; MeOH) | 238° C. 632; 5.88 (M1) |
| 8 | ![piperidine] | —OMe | 2-OMe | Base +88° (c = 1; AcOEt) | 105° C. 617; 6.59 (M1) |
| 9 | ![4,4-difluoropiperidine] | —OEt | 3-OMe | Base +61.5° (c = 1; AcOEt) | 88° C. 667; 7.26 (M1) |
| 10 | ![4-hydroxypiperidine] | —OEt | 3-OMe | Base +60.8° (c = 1; AcOEt) | 102° C. 647; 6.64 (M1) |
| 11 | ![morpholine] | —OEt | 3-OMe | Base +64.8° (c = 1; AcOEt) | 153° C. 633; 6.65 (M1) |
| 12 | ![N-methylpiperazine] | —OMe | 2-OMe | Base +71.6° (c = 1; AcOEt) | 123° C. 632; 6.90 (M1) |

TABLE VIII-continued (I):

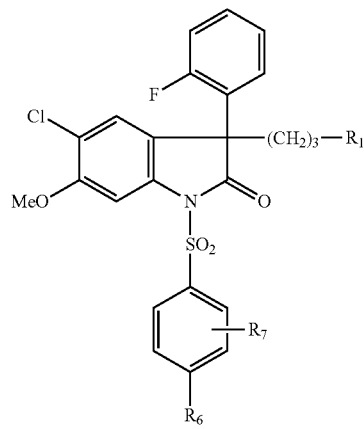

$R_2$ = Cl
$R_3$ = OMe
$R_4$ = F
$R_5$ = H
X = $(CH_2)_3$

| Compound No. | $R_1$ | $R_6$ | $R_7$ | Salt/Base $\alpha_D^{20}$ (c; solvent) | M.p. °C. $MH^+$; rt (Conditions) |
|---|---|---|---|---|---|
| 13 | —N(piperazine)N—Me | —OiPr | H | HCl +114.8° (c = 1; MeOH) | 205° C. 630; 7.09 (M1) |
| 14 | —N(piperazine)N—Me | —OEt | 3-OMe | HCl +106.2° (c = 1; MeOH) | 180° C. 646; 6.76 (M1) |
| 15 | —N(piperazine)N—Me | —OMe | 3-OMe | Base +60.3° (c = 1; AcOEt) | 90° C. 632; 6.44 (M1) |
| 16 | —N(piperazine)NH | —OMe | 2-OMe | HCl +122° (c = 1; MeOH) | 243° C. 618; 6.38 (M1) |
| 17 | —N(piperazine)NH | —OiPr | H | HCl +120.8° (c = 1; MeOH) | 232° C. 616; 6.51 (M1) |
| 18 | —N(piperazine)NH | —OEt | 3-OMe | HCl +114.2° (c = 1; MeOH) | 220° C. 632; 6.51 (M1) |
| 19 | —N(piperazine)NH | —OMe | 3-OMe | HCl +111.3° (c = 1; MeOH) | 190° C. 618; 6.57 (M1) |
| 20 | —N(piperazine)NH | —Me | 3-Me | HCl +123.7° (c = 1; MeOH) | 192° C. 586; 6.40 (M1) |
| 21 | —N(piperazine)NH | —OMe | 3-Me | HCl +132.7° (c = 1; MeOH) | 234° C. 602; 6.53 (M2) |

TABLE VIII-continued (I):

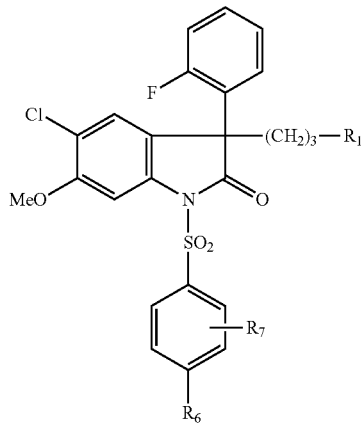

$R_2$ = Cl
$R_3$ = OMe
$R_4$ = F
$R_5$ = H
X = $(CH_2)_3$

| Compound No. | $R_1$ | $R_6$ | $R_7$ | Salt/Base $\alpha_D^{20}$ (c; solvent) | M.p. ° C. MH+; rt (Conditions) |
|---|---|---|---|---|---|
| 22 | —N⟨piperazine⟩NH | —OEt | H | HCl +123.5° (c = 1; MeOH) | 213° C. 602; 8.94 (M2) |
| 23 | —N⟨piperazine⟩NH | —OEt | 3-Me | HCl +142.6° (c = 1; MeOH) | 226° C. 616; 6.84 (M2) |
| 24 | —N⟨piperazine⟩NH | —OCHF$_2$ | H | HCl +121.8° (c = 1; MeOH) | 218° C. 624; 6.45 (M1) |
| 25 | —N⟨piperazine⟩NH | —OCF$_3$ | H | HCl +135° (c = 1; MeOH) | 220° C. 642; 6.86 (M1) |
| 26 | —N⟨piperazine⟩NH | H | H | HCl +123.5° (c = 1; MeOH) | 238° C. 558; 6.58 (M1) |
| 27 | —N⟨piperazine⟩NH | R6 + R7 = —(CH$_2$)$_3$— | | HCl +129° (c = 1; MeOH) | 242° C. 598; 7.06 (M1) |
| 28 | —N⟨pyrrolidine⟩NMe$_2$ | —OMe | 3-Me | Base +71.2° (c = 0.5; MeOH) | 76° C. 630; 5.62 (M4) |
| 29 | —N⟨piperazine⟩N—Me | —OMe | 3-Me | Base +67.3° (c = 0.53; MeOH) | 96° C. 616; 6.18 (M4) |
| 30 | —N⟨piperazine⟩NH | —OMe | 3-F | HCl +121.8° (c = 0.5; MeOH) | 170° C. 606; 6.49 (M4) |

TABLE VIII-continued (I):

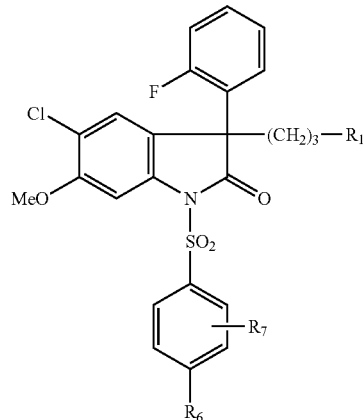

R₂ = Cl
R₃ = OMe
R₄ = F
R₅ = H
X = (CH₂)₃

| Compound No. | $R_1$ | $R_6$ | $R_7$ | Salt/Base $\alpha_D^{20}$ (c; solvent) | M.p. °C. MH⁺; rt (Conditions) |
|---|---|---|---|---|---|
| 31 | 1-methyl-3,3-difluoropiperidin-3-yl | —NHCO—NEt₂ | 3-Me | Base +52° (c = 1; MeOH) | 150° C. 721; 7.77 (M1) |
| 32 | —N(Me)₂ | —NHCO—NEt₂ | 3-Me | Base +65° (c = 1; MeOH) | 122° C. 645; 7.03 (M1) |
| 33 | 4-(2,2,2-trifluoroethyl)piperazin-1-yl | —OiPr | H | HCl +114° (c = 1; MeOH) | 272° C. 698; 7.71 (M4) |
| 34 | 4-ethylpiperazin-1-yl | —OiPr | H | HCl +131° (c = 1; MeOH) | 316° C. 644; 7.03 (M4) |
| 35 | 4-methyl-1,4-diazepan-1-yl | —OiPr | H | HCl +153° (c = 1; MeOH) | 175° C. 630; 6.24 (M4) |
| 36 | 4-methylpiperazin-1-yl | —OMe | H | HCl +125° (c = 1; MeOH) | — 602; 6.63 (M4) |
| 37 | 4-methylpiperazin-1-yl | H | 3-Cl | HCl +151° (c = 1; MeOH) | 228° C. 606; 6.91 (M4) |
| 38 | 4-methylpiperazin-1-yl | H | 3-OMe | HCl +132° (c = 1; MeOH) | 147° C. 602; 6.14 (M4) |

TABLE VIII-continued (I):

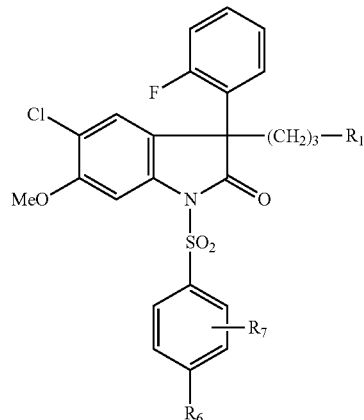

R₂ = Cl
R₃ = OMe
R₄ = F
R₅ = H
X = (CH₂)₃

| Compound No. | R₁ | R₆ | R₇ | Salt/Base $\alpha_D^{20}$ (c; solvent) | M.p. ° C. MH⁺; rt (Conditions) |
|---|---|---|---|---|---|
| 39 | ![structure: N-methyl bicyclic diamine] | —OiPr | H | HCl +160° (c = 1; MeOH) | 200° C. 628; 6.38 (M4) |
| 40 | —N(piperazine)N—Me | —iPr | H | HCl +143° (c = 1; MeOH) | 173° C. 614; 6.70 (M4) |
| 41 | —N(piperazine)N—Me | —OH | H | — +69° (c = 1; MeOH) | 169° C. 588; 15.3 (M2) |
| 42 | —N(piperazine)N—iPr | —OiPr | H | HCl +146° (c = 1; MeOH) | 194° C. 658; 6.76 (M4) |
| 43 | —N(piperazine)N—Me | —OBu | H | HCl +129° (c = 1; MeOH) | 156° C. 644; 14.4 (M5) |
| 44 | —N(piperidine)N—Me (4-methylpiperazine variant) | —OiPr | H | HCl +109° (c = 1; MeOH) | 160° C. 629; 15.1 (M5) |
| 45 | —N(piperazine with Me)NH | —OiPr | H | HCl +137° (c = 1; MeOH) | 190° C. 630; 6.46 (M4) |
| 46 | —N(piperazine)NH | —OH | H | HCl +97° (c = 1; DMF) | 292° C. 574; 6.21 (M4) |

TABLE VIII-continued (I):

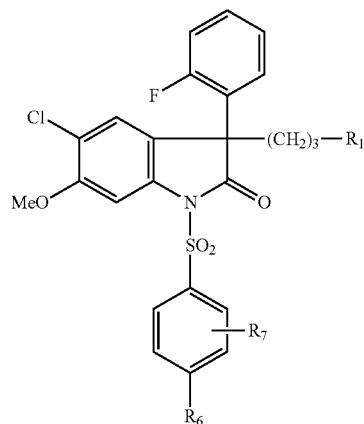

R$_2$ = Cl
R$_3$ = OMe
R$_4$ = F
R$_5$ = H
X = (CH$_2$)$_3$

| Compound No. | R$_1$ | R$_6$ | R$_7$ | Salt/Base α$_D^{20}$ (c; solvent) | M.p. °C. MH$^+$; rt (Conditions) |
|---|---|---|---|---|---|
| 47 | —N(piperazine with two Me, one with stereochem)— | —OiPr | H | HCl +135° (c = 1; MeOH) | 203° C. 644; 7.17 (M4) |
| 48 | —N(piperazine)—N—cyclobutyl | —OiPr | H | HCl +127° (c = 1; MeOH) | 182° C. 670; 7.35 (M4) |
| 49 | —N(piperazine)—N—Me | —O—cyclopentyl | H | HCl +160° (c = 1; MeOH) | 211° C. 656; 7.36 (M4) |
| 50 | —N(piperazine)—NH | H | 3-Cl | HCl +175° (c = 1; MeOH) | 193° C. 592; 6.13 (M4) |
| 51 | —N(piperazine)—NH | —H | 3-OMe | HCl +156° (c = 1; MeOH) | 161° C. 588; 5.92 (M4) |
| 52 | —N(diazabicyclic, dimethyl) | —OiPr | H | HCl +151° (c = 1; MeOH) | 184° C. 642; 6.54 (M4) |
| 53 | —N(morpholine) | —OiPr | H | HCl +148° (c = 1; MeOH) | 154° C. 617; 6.92 (M4) |

TABLE VIII-continued (I):

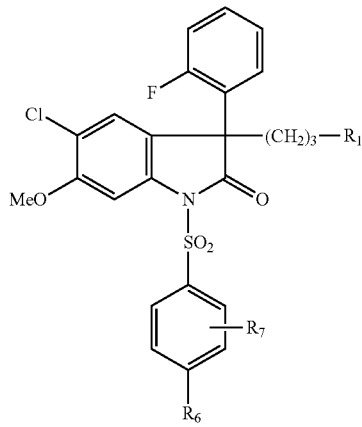

$R_2$ = Cl  
$R_3$ = OMe  
$R_4$ = F  
$R_5$ = H  
X = $(CH_2)_3$

| Compound No. | $R_1$ | $R_6$ | $R_7$ | Salt/Base $\alpha_D^{20}$ (c; solvent) | M.p. ° C. MH+; rt (Conditions) |
|---|---|---|---|---|---|
| 54 | ![](piperazine with two Me) | —OiPr | H | HCl +121° (c = 1; MeOH) | 177° C. 658; 7.17 (M4) |
| 55 | ![](diazepane N,N'-diMe) | —OiPr | H | HCl +145° (c = 1; MeOH) | 202° C. 644; 6.32 (M4) |
| 56 | ![](bicyclic diamine N-Me) | —OiPr | H | HCl +118° (c = 1; MeOH) | 200° C. 656; 7.34 (M4) |
| 57 | | —OEt | H | HCl +126° (c = 1; MeOH) | 211° C. 616; 6.41 (M4) |
| 58 | ![](piperazine NH) | —OCF$_2$CHF$_2$ | H | HCl +135° (c = 1; MeOH) | 199° C. 674; 6.40 (M4) |
| 59 | | —OCF$_2$CHF$_2$ | H | HCl +148° (c = 1; MeOH) | 164° C. 688; 6.66 (M4) |
| 60 | ![](piperazine with two Me, NH) | —OiPr | H | HCl +130° (c = 1; MeOH) | 219° C. 644; 6.55 (M4) |

TABLE VIII-continued (I):

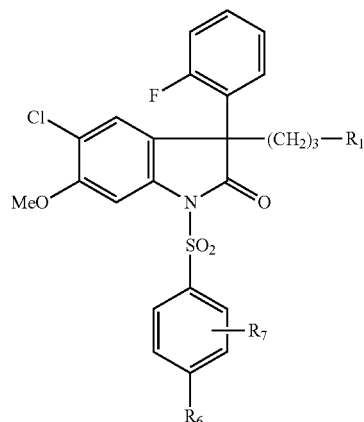

R₂ = Cl
R₃ = OMe
R₄ = F
R₅ = H
X = (CH₂)₃

| Compound No. | R₁ | R₆ | R₇ | Salt/Base $\alpha_D^{20}$ (c; solvent) | M.p. °C. MH⁺; rt (Conditions) |
|---|---|---|---|---|---|
| 61 | (2,6-dimethylpiperazinyl, cis) | —OiPr | H | HCl +147° (c = 1; MeOH) | 226° C. 644; 6.70 (M4) |
| 62 | piperazinyl | —OiPr | 3-F | HCl +126° (c = 1; MeOH) | 174° C. 634; 6.39 (M4) |
| 63 | 4-methylpiperazinyl | —OiPr | 3-F | HCl +145° (c = 1; MeOH) | 207° C. 648; 6.66 (M4) |
| 64 | 3-isopropylpiperazinyl | —OiPr | H | HCl +123° (c = 1; MeOH) | 196° C. 658; 6.72 (M4) |
| 65 | 3-methylpiperazinyl | —OiPr | H | HCl +148° (c = 1; MeOH) | 203° C. 630; 6.49 (M4) |
| 66 | 3,3-dimethylpiperazinyl | —OiPr | H | HCl +122° (c = 1; MeOH) | 203° C. 644; 6.52 (M4) |

TABLE VIII-continued (I):

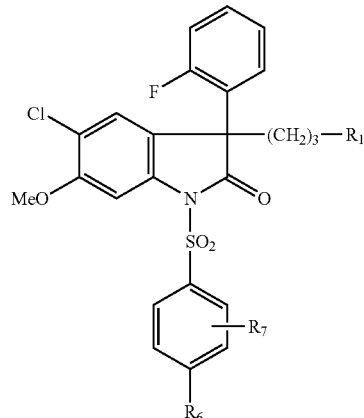

R$_2$ = Cl
R$_3$ = OMe
R$_4$ = F
R$_5$ = H
X = (CH$_2$)$_3$

| Compound No. | R$_1$ | R$_6$ | R$_7$ | Salt/Base α$_D^{20}$ (c; solvent) | M.p. °C. MH$^+$; rt (Conditions) |
|---|---|---|---|---|---|
| 67 | (1-methyl-diazabicyclo[2.2.1]) | —OiPr | H | HCl +151° (c = 1; MeOH) | 210° C. 642; 5.98 (M4) |
| 68 | (2,5-dimethyl-4-methylpiperazinyl) | —OiPr | H | HCl +144° (c = 1; MeOH) | 218° C. 644; 6.48 (M4) |
| 69 | (3-iPr-1,4-dimethylpiperazinyl) | —OiPr | H | HCl +133° (c = 1; MeOH) | 188° C. 672; 7.29 (M4) |
| 70 | (3-Pr-4-methylpiperazinyl) | —OiPr | H | HCl +134° (c = 1; MeOH) | 173° C. 672; 7.40 (M4) |
| 71 | (2,2-dimethyl-4-methylpiperazinyl) | —OiPr | H | HCl +131° (c = 1; MeOH) | 195° C. 658; 7.36 (M4) |
| 72 | (piperazinyl) | —OtBu | H | — +90° (c = 1; DMF) | 630; 6.79 (M4) |

TABLE VIII-continued (I):

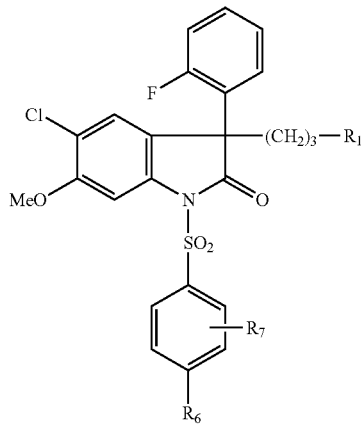

R$_2$ = Cl
R$_3$ = OMe
R$_4$ = F
R$_5$ = H
X = (CH$_2$)$_3$

| Compound No. | R$_1$ | R$_6$ | R$_7$ | Salt/Base $\alpha_D^{20}$ (c; solvent) | M.p. °C. MH$^+$; rt (Conditions) |
|---|---|---|---|---|---|
| 73 | 2,5-dimethyl-1,4-dimethylpiperazinyl (Me groups shown) | —OiPr | H | HCl +130° (c = 1; MeOH) | 201° C. 658; 7.18 (M4) |
| 74 | 3,3-dimethyl-1,4-dimethylpiperazinyl | —OiPr | H | HCl +138° (c = 1; MeOH) | — 658; 6.86 (M4) |
| 75 | methyl-diazabicyclic | —OiPr | H | HCl +166° (c = 1; MeOH) | — 642; 5.79 (M4) |
| 76 | 2-iPr-1-methylpiperazinyl | —OiPr | H | HCl +136° (c = 1; MeOH) | — 658; 6.73 (M4) |
| 77 | methyl-octahydropyrrolo[1,2-a]pyrazinyl | —OiPr | H | HCl +128° (c = 1; MeOH) | — 656; 6.76 (M4) |
| 78 | methyl-octahydropyrido[1,2-a]pyrazinyl | —OiPr | H | HCl +136° (c = 1; MeOH) | — 670; 6.80 (M4) |

TABLE VIII-continued (I):

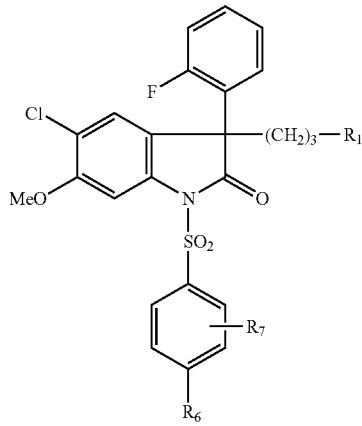

R₂ = Cl
R₃ = OMe
R₄ = F
R₅ = H
X = (CH₂)₃

| Compound No. | $R_1$ | $R_6$ | $R_7$ | Salt/Base $\alpha_D^{20}$ (c; solvent) | M.p. °C. $MH^+$; rt (Conditions) |
|---|---|---|---|---|---|
| 79 | 4-methyl-2-(trifluoromethyl)piperazinyl | —OiPr | H | HCl +121° (c = 1; MeOH) | — 684; 7.55 (M4) |
| 80 | 4-methylpiperazinyl | —OiPr | 3-Cl | HCl +153° (c = 1; MeOH) | — 650; 6.57 (M4) |
| 81 | 4-methylpiperazinyl | —OiPr | 2-OMe | HCl +122° (c = 1; MeOH) | — 646; 6.60 (M4) |
| 82 | 4-methylpiperazinyl | —OiPr | 3-OMe | HCl +128° (c = 1; MeOH) | — 646; 6.61 (M4) |
| 83 | 4-methylpiperazinyl-N-Me | —OiPr | 3-CF₃ | HCl +112° (c = 1; MeOH) | — 698; 7.48 (M4) |
| 84 | 4-methylpiperazinyl-N-Me | —OiPr | 3-OMe | HCl +118° (c = 1; MeOH) | — 660; 6.81 (M4) |
| 85 | 4-methylpiperazinyl-N-Me | —OiPr | 3-Me | HCl +121° (c = 1; MeOH) | — 644; 7.30 (M4) |
| 86 | piperazinyl-N-SO₂Me | —OiPr | H | HCl +124° (c = 1; MeOH) | — 694; 7.47 (M4) |

TABLE VIII-continued
(I):
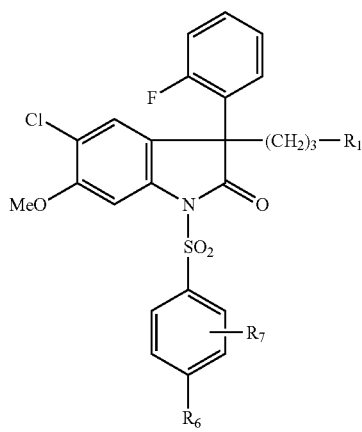
R₂ = Cl
R₃ = OMe
R₄ = F
R₅ = H
X = (CH₂)₃
| Compound No. | R₁ | R₆ | R₇ | Salt/Base $\alpha_D^{20}$ (c; solvent) | M.p. °C. MH⁺; rt (Conditions) |
|---|---|---|---|---|---|
| 87 | ⌇—[piperidine-N-Me] | —OiPr | H | HCl +117° (c = 1; MeOH) | — 629; 7.52 (M4) |
| 88 | ⌇—[piperidine-N-Me] | —OiPr | H | HCl +132° (c = 1; MeOH) | — 629; 7.48 (M4) |
| 89 | —N[piperazine]N—Me | —OCHF₂ | H | HCl +116° (c = 1; MeOH) | — 638; 6.84 (M4) |
| 90 | —N[piperazine]N—iPr | —OCF₂CHF₂ | H | HCl +121° (c = 1; MeOH) | — 716; 7.25 (M4) |
| 91 | —N[piperazine]N—iPr | —OiPr | 3-F | HCl +124° (c = 1; MeOH) | — 676; 7.25 (M4) |
| 92 | —N[piperazine]NH | —OEt | 3-F | HCl +126° (c = 1; MeOH) | — 620; 6.65 (M4) |

TABLE VIII-continued
(I):
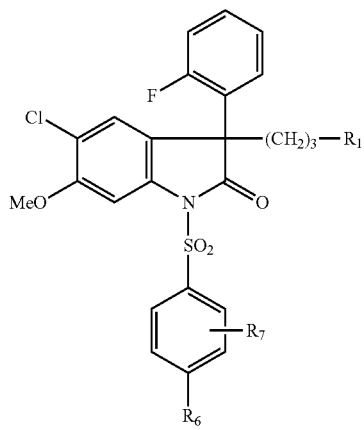
$R_2$ = Cl
$R_3$ = OMe
$R_4$ = F
$R_5$ = H
X = $(CH_2)_3$
| Compound No. | $R_1$ | $R_6$ | $R_7$ | Salt/Base $\alpha_D^{20}$ (c; solvent) | M.p. °C. MH+; rt (Conditions) |
|---|---|---|---|---|---|
| 93 | —N(piperazine)N—Me | —OEt | 3-F | HCl +110° (c = 1; MeOH) | — 634; 6.92 (M4) |
| 94 | —N(piperazine)N—Me | —OtBu | H | — +56° (c = 1; DMF) | — 644; 7.19 (M4) |
| 94a | —N(piperidine)N(Me)$_2$ | —OiPr | H | HCl +142° (c = 1; MeOH) | — 658; 6.05 (M4) |

TABLE IX (I):

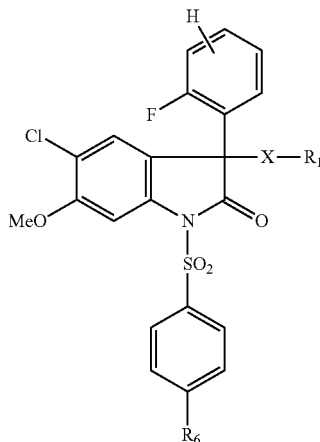

R$_2$ = Cl
R$_3$ = OMe
R$_4$ = F
R$_5$ = H
R$_7$ = H

| Compound No. | R$_1$ | X | R$_6$ | Salt/Base $\alpha_D^{20}$ (c; solvent) | M.p. °C. MH$^+$; rt (Conditions) |
|---|---|---|---|---|---|
| 95 | N-methylpiperidine (N-linked) | (CH$_2$)$_4$ | —OiPr | HCl +111° (c = 1; MeOH) | 140° C. 629; 7.52 (M4) |
| 96 | —N(Me)$_2$ | (CH$_2$)$_5$ | —OiPr | HCl +128° (c = 1; MeOH) | 125° C. 603; 7.43 (M4) |
| 97 | N-methylpiperidine (N-linked) | (CH$_2$)$_5$ | —OiPr | HCl +116° (c = 1; MeOH) | 203° C. 643; 7.16 (M4) |
| 98 | 4-piperidinyl (NH) | (CH$_2$)$_2$ | —OiPr | HCl +102° (c = 1; MeOH) | 162° C. 601; 7.41 (M4) |
| 99 | 1-methyl-4-piperidinyl | (CH$_2$)$_2$ | —OiPr | HCl +112° (c = 1; MeOH) | 162° C. 615; 6.89 (M4) |
| 100 | 1-methyl-4-piperidinyl | CH$_2$ | —OiPr | HCl +139° (c = 1; MeOH) | 189° C. 601; 7.19 (M4) |
| 101 | piperazinyl (NH) | (CH$_2$)$_2$ | —OiPr | HCl +186° (c = 1; MeOH) | 188° C. 602; 6.68 (M4) |
| 102 | (3-methylpiperidinyl, NH) | CH$_2$ | —OiPr | HCl +202° (c = 1; MeOH) | — 587; 13.9 (M5) |

TABLE IX-continued (I):

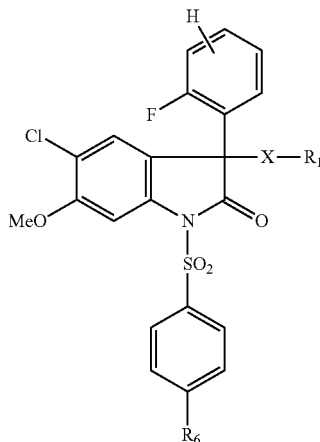

$R_2 = Cl$
$R_3 = OMe$
$R_4 = F$
$R_5 = H$
$R_7 = H$

| Compound No. | $R_1$ | X | $R_6$ | Salt/Base $\alpha_D^{20}$ (c; solvent) | M.p. °C. MH+; rt (Conditions) |
|---|---|---|---|---|---|
| 103 | 4-methylpiperidin-N-Me | $(CH_2)_2$ | $-OCF_2CHF_2$ | HCl +104° (c = 1; MeOH) | — 673; 14.9 (M5) |

TABLE X

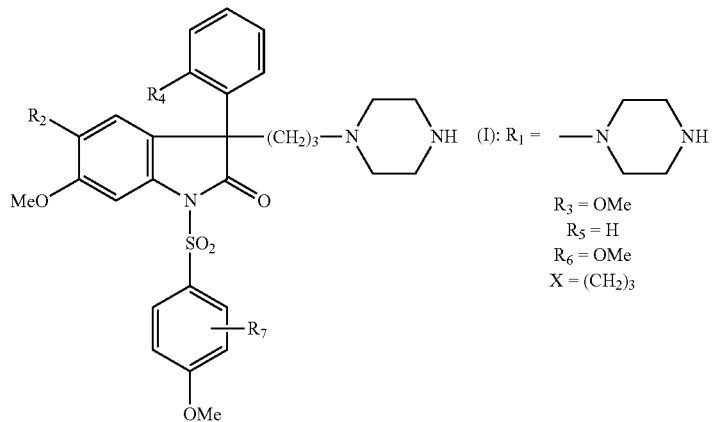

(I): $R_1 =$ piperazinyl-NH $R_3 = OMe$
$R_5 = H$
$R_6 = OMe$
$X = (CH_2)_3$

| Compound No. | $R_2$ | $R_4$ | $R_7$ | Salt/Base $\alpha_D^{20}$ (c; solvent) | M.p. °C. MH+; rt (Conditions) |
|---|---|---|---|---|---|
| 104 | Cl | Me | 3-Me | HCl +147.6° (c = 1; MeOH) | 172° C. 598; 6.32 (M4) |
| 105 | Cl | H | 3-Me | HCl +60.4° (c = 0.52; MeOH) | 170° C. 584; 6.12 (M4) |
| 106 | Me | F | 3-Me | HCl +120.6° (c = 0.5; MeOH) | 164° C. 582; 6.50 (M4) |

TABLE X-continued
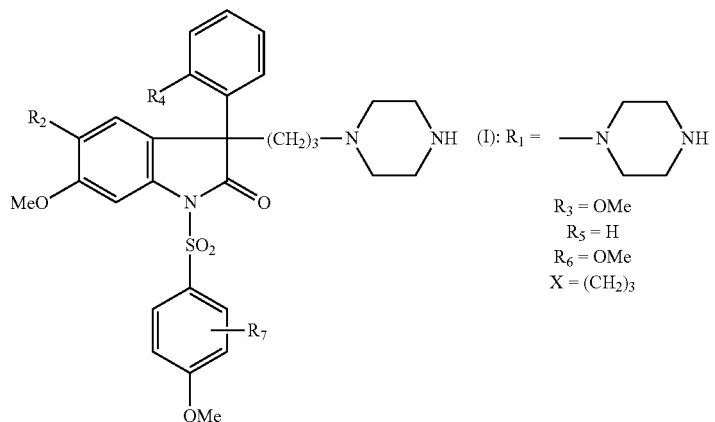
(I): $R_1 =$ piperazine-NH
$R_3 = OMe$
$R_5 = H$
$R_6 = OMe$
$X = (CH_2)_3$
| Compound No. | $R_2$ | $R_4$ | $R_7$ | Salt/Base $\alpha_D^{20}$ (c; solvent) | M.p. °C. MH+; rt (Conditions) |
|---|---|---|---|---|---|
| 107 | F | F | 3-Me | HCl +113.6° (c = 0.5; MeOH) | 152° C. 586; 6.38 (M4) |
| 108 | OMe | F | 3-Me | HCl +96.3° (c = 0.51; MeOH) | 160° C. 598; 6.16 (M4) |
| 109 | Cl | Me | 2-OMe | HCl +131° (c = 1; MeOH) | 184° C. 614; 5.96 (M4) |
| 110 | Cl | H | 2-OMe | HCl +26.1° (c = 0.51; MeOH) | 174° C. 600; 11.1 (M5) |
| 111 | Me | F | 2-OMe | HCl +117.2° (c = 0.53; MeOH) | 222° C. 598; 6.16 (M4) |
| 112 | F | F | 2-OMe | HCl +105.4° (c = 0.5; MeOH) | 178° C. 602; 6.05 (M4) |
| 113 | OMe | F | 2-OMe | HCl +89.8° (c = 0.53; MeOH) | 228° C. 614; 5.73 (M4) |

TABLE XI (I):

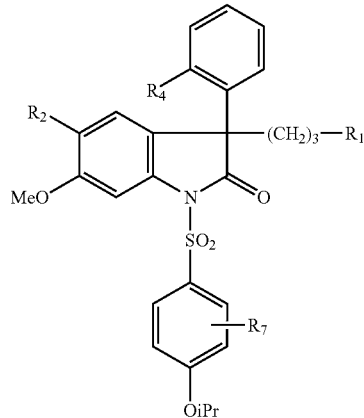

$R_3$ = OMe
$R_5$ = H
$R_6$ = OiPr
X = $(CH_2)_3$

| Compound No. | $R_1$ | $R_2$ | $R_4$ | $R_7$ | Salt/Base $\alpha_D^{20}$ (c; solvent) | M.p. °C. MH+; rt (Conditions) |
|---|---|---|---|---|---|---|
| 114 | —N(piperazine)NH | Cl | H | H | HCl +61.6° (c = 0.5; MeOH) | 204° C. 599; 6.33 (M4) |
| 115 | —N(piperazine)NH | F | F | H | HCl +112.9° (c = 0.54; MeOH) | 162° C. 600; 6.59 (M4) |
| 116 | —N(piperazine)NH | OMe | F | H | HCl +93.2° (c = 0.51; MeOH) | 164° C. 612; 6.26 (M4) |
| 117 | —N(piperazine)N—Me | Cl | H | H | Base −39.7° (c = 1; MeOH) | 97° C. 612; 7.04 (M4) |
| 118 | —N(piperazine)N—Me | Me | F | H | Base +69.6° (c = 0.54; AcOEt) | 70° C. 610; 13.23 (M5) |
| 119 | —N(piperazine)N—Me | F | F | H | Base +74° (c = 0.53; AcOEt) | 72° C. 614; 6.94 (M4) |
| 120 | —N(piperazine)N—Me | OMe | F | H | Base +63.8° (c = 0.5; AcOEt) | 80° C. 626; 6.68 (M4) |
| 121 | —N(piperazine)NH | F | F | 3-F | HCl +109° (c = 0.51; MeOH) | 152° C. 618; 6.83 (M4) |
| 122 | —N(piperazine)N—Me | Cl | H | 3-F | Base −60° (c = 0.5; AcOEt) | 93° C. 629; 7.37 (M4) |

TABLE XI-continued
(I):
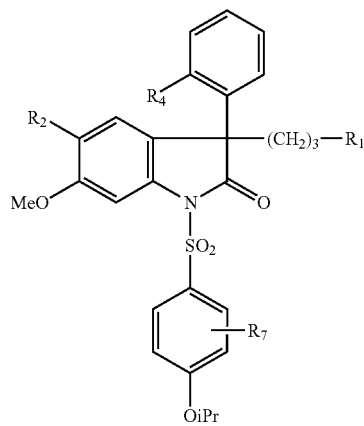
R₃ = OMe
R₅ = H
R₆ = OiPr
X = (CH₂)₃
| Compound No. | R₁ | R₂ | R₄ | R₇ | Salt/Base $\alpha_D^{20}$ (c; solvent) | M.p. °C. MH+; rt (Conditions) |
|---|---|---|---|---|---|---|
| 123 | —N(piperazine)NH-Me | Br | F | H | — +151° (c = 1; DMF) | — 660; 6.82 (M4) |
| 124 | —N(piperazine)N—Me | Br | F | H | — +144° (c = 1; DMF) | — 674; 7.12 (M4) |
| 124a | —N(piperazine)N—Me | OMe | F | 3-F | Base +71.2° (c = 0.5; MeOH) | 74° C. 644; 6.57 (M4) |
| 124b | —N(piperazine)N—Me | F | F | 3-F | Base +78° (c = 0.53; MeOH) | 72° C. 632; 6.92 (M4) |

TABLE XII (I): R₁ = piperazinyl-NH

R₂ = Cl
X = (CH₂)₃

| Compound No. | R₄ | R₅ | R₆ | R₇ | Salt/Base $\alpha_D^{20}$ (c; solvent) | M.p. °C. MH⁺; rt (Conditions) |
|---|---|---|---|---|---|---|
| 125 | F | 5-F | —OMe | 3-Me | HCl +137.3° (c = 0.52; MeOH) | 172° C. 620; 6.23 (M4) |
| 126 | F | 3-Cl | —OMe | 3-Me | HCl +136° (c = 0.5; MeOH) | 174° C. 636; 6.82 (M4) |
| 127 | F | 6-F | —OiPr | H | HCl +161.5° (c = 1; MeOH) | 182° C. 634; 6.78 (M4) |
| 128 | F | 3-Cl | —OiPr | H | HCl +135° (c = 0.51; MeOH) | 170° C. 650; 7.02 (M4) |
| 129 | F | 5-F | —OMe | 2-OMe | HCl +117.6° (c = 0.5; MeOH) | 174° C. 636; 5.91 (M4) |
| 130 | F | 3-Cl | —OMe | 2-OMe | HCl +111.2° (c = 0.51; MeOH) | 174° C. 652; 6.50 (M4) |

TABLE XIII (I): R₁ = N-methylpiperazinyl

X = (CH₂)₃

| Compound No. | R₂ | R₄ | R₅ | R₆ | R₇ | Salt/Base $\alpha_D^{20}$ (c; solvent) | M.p. °C. MH⁺; rt (Conditions) |
|---|---|---|---|---|---|---|---|
| 131 | Me | F | H | —OMe | 3-Me | Base +65° (c = 0.53; AcOEt) | 86° C. 596; 12.5 (M5) |

TABLE XIII-continued

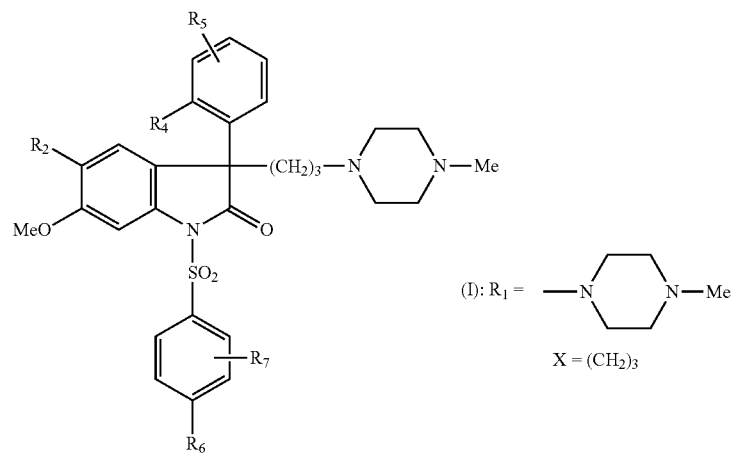

(I): $R_1 = $ —N‿N—Me $X = (CH_2)_3$

| Compound No. | $R_2$ | $R_4$ | $R_5$ | $R_6$ | $R_7$ | Salt/Base $\alpha_D^{20}$ (c; solvent) | M.p. °C. MH+; rt (Conditions) |
|---|---|---|---|---|---|---|---|
| 132 | Cl | F | 3-Cl | —OMe | 3-Me | Base +78.2° (c = 0.51; MeOH) | 86° C. 650; 7.2 (M4) |
| 133 | Me | F | H | —OEt | 3-Me | Base +61.1° (c = 0.54; AcOEt) | 74° C. 610; 13.14 (M5) |
| 134 | Cl | H | H | —OCF$_2$—CHF$_2$ | H | Base −42° (c = 0.5; AcOEt) | 80° C. 670; 7.17 (M4) |
| 134a | OMe | F | H | —OMe | 3-Me | Base +61.2° (c = 0.5; MeOH) | 78° C. 612; 6.05 (M4) |
| 134b | Cl | F | 5-CO$_2$Me | —OiPr | H | Base +96.8° (c = 0.5; MeOH) | 100° C. 688; 13.37 (M5) |
| 134c | Cl | F | 5-CH$_2$OH | —OiPr | H | Base +88.2° (c = 0.5; MeOH) | 97° C. 660; 12.78 (M5) |

TABLE XIV (I):

$R_1 = $ —N(Me)$_2$
$R_2 = $ Me
$R_3 = $ OMe
$R_4 = $ F
$R_5 = $ H
$X = (CH_2)_3$

| Compound No. | $R_6$ | $R_7$ | Salt/Base $\alpha_D^{20}$ (c; solvent) | M.p. °C. MH+; rt (Conditions) |
|---|---|---|---|---|
| 135 | —NHCO—NEt$_2$ | 3-Me | Base +68.2° (c = 0.54; AcOEt) | 98° C. 625; 6.78 (M4) |
| 136 | —NHCO—NEt$_2$ | 3-F | Base +86.9° (c = 0.52; AcOEt) | 82° C. 629; 6.87 (M4) |

The compounds according to the invention have formed the subject of pharmacological assays.

The affinity of the compounds of formula (I) according to the invention for arginine-vasopressin $V_{1a}$ receptors was determined in vitro using the method described by M. Thibonnier et al., J. Biol. Chem., 1994, 269, 3304-3310. This method consists in studying in vitro the displacement of tritiated arginine-vasopressin ([$^3$H]-AVP) at the $V_{1a}$ receptors present on membrane or cell preparations carrying rat or human $V_{1a}$ receptors. The compounds of formula (I) exhibit an affinity for human arginine-vasopressin $V_{1a}$ receptors with IC$_{50}$ values (concentration which inhibits by 50% the binding of tritiated arginine-vasopressin ([$^3$H]-AVP) to its receptors) generally of less than 10 nanomolar (10$^{-8}$ M) in the latter test.

The affinity of the compounds of formula (I) according to the invention for arginine-vasopressin $V_{1b}$ receptors was determined in vitro using the method described by Y. de Keyser et al. in Febs Letters, 1994, 356, 215-220. This method consists in studying in vitro the displacement of tritiated arginine-vasopressin ([$^3$H]-AVP) at the $V_{1b}$ receptors present on cell preparations carrying human $V_{1b}$ receptors. Some compounds studied exhibit in addition an affinity for human $V_{1b}$ receptors with $IC_{50}$ values of less than 30 nanomolar ($3 \times 10^{-8}$ M) in the latter test.

The affinity of the compounds of formula (I) according to the invention for vasopressin $V_2$ receptors was also studied (method described by M. Birnbaumer et al. in Nature (Lond.), 1992, 357, 333-335). The compounds studied have little or no affinity for human $V_2$ receptors with $IC_{50}$ values of greater than $10^{-7}$ M.

The affinity of the compounds according to the invention for oxytocin receptors was determined in an in vitro binding test using the method described by J. Elands et al. in Eur. J. Pharmacol., 1987, 147, 197-207. This method consists in studying in vitro the displacement of a radioiodinated oxytocin analog at the oxytocin receptors in a cell membrane preparation transfected with the human uterine oxytocin receptor.

The compounds studied have little or no affinity for human oxytocin receptors with $IC_{50}$ values generally of greater than $10^{-7}$ M.

The comparative pharmacological results of Compounds Nos. 17, 38, 46, 107 and 108 according to the invention with the compounds α and β of the prior art on the various in vitro tests measuring the affinity at human $V_{1a}$, $V_{1b}$, $V_2$ and oxytocin receptors are illustrated in the following TABLE XV. The results are expressed by the 50% inhibitory concentration ($IC_{50}$) expressed on a nanomolar basis (nM).

TABLE XV

| | BINDING | | | |
|---|---|---|---|---|
| | Human $V_{1a}$ $IC_{50}$ (nM) | Human $V_{1b}$ $IC_{50}$ (nM) | Human $V_2$ $IC_{50}$ (nM) | Human oxytocin $IC_{50}$ (nM) |
| Compound α | 23 | 210 | 19 | 100 |
| Compound β | 18 | 180 | 13 | 69 |
| Compound No. 17 | 2.4 | >1000 | 450 | 390 |
| Compound No. 38 | 1.1 | >1000 | >1000 | 500 |
| Compound No. 46 | 2.4 | 640 | >1000 | 380 |
| Compound No. 107 | 8.5 | 140 | >1000 | >1000 |
| Compound No. 108 | 5 | 320 | >1000 | >1000 |

The agonist or antagonist nature of the compounds is determined in vitro in a test for the measurement of intracellular calcium (FLIPR) on cells expressing human $V_{1a}$ receptors according to the general technique described in Sullivan et al., Methods Mol. Biol., 1999, 114, 125-133, using 1 μM of Fluo4 AM, and in a test for platelet aggregation induced with AVP on human PRP (platelet-rich plasma) according to the methodology described in J. Clin. Invest., 1993, 92, 224-231. The compounds are preincubated 30 minutes before the addition of the arginine-vasopressin in order to determine the agonist and antagonist properties of these molecules. The $IC_{50}$ values of the compounds according to the invention for the $V_{1a}$ receptors measured in these studies are low (less than $2 \times 10^{-8}$ M).

These pharmacological results show that the compounds according to the invention, in particular Compound No. 13 and Compound No. 17, are antagonists of $V_{1a}$ receptors by blocking the pharmacological effects brought about by arginine-vasopressin.

The compounds according to the invention can thus be used in the preparation of medicaments, in particular of medicaments which are antagonists of human arginine-vasopressin $V_{1a}$ receptors and in addition, for some compounds, of human AVP $V_{1b}$ receptors.

Thus, according to another of its aspects, a subject matter of the invention is medicaments which comprise a compound of formula (I) or an addition salt of the latter with a pharmaceutically acceptable acid or also a hydrate or a solvate of the compound of formula (I).

These medicaments find use in therapeutics and are advantageously of use in disorders of the urogenital sphere, in particular in the obstetrical and gynecological fields, in particular as uterine relaxant or tocolytic agent or for controlling uterine hyperactivity or contractions of the uterus before pregnancy has arrived at term, for controlling prenatal labor, or also controlling preparatory labor for the purpose of a cesarean delivery, promoting growth of the fetus in utero, reducing stress and anoxia during contractions, for solving problems of sterility or fertility, controlling births (in particular veterinary use), controlling estrus, weaning or embryo transfer and implantation during in vitro fertilization; treating endometriosis, dysmenorrhea, and also urinary stress or urgency incontinence, benign prostate hypertrophy, disorders of micturition, urogenital infections, urinary lithiases and erectile dysfunctions.

These medicaments are also of use in the treatment or prevention of various vasopressin-dependent conditions, such as cardiovascular conditions, for example hypertension, pulmonary hypertension, cardiac insufficiency, myocardial infarction or coronary vasospasm, in particular in smokers, Raynaud's syndrome, unstable angina and PTCA (percutaneous transluminal coronary angioplasty), cardiac ischemia, hemostasis disturbances or thrombosis; conditions of the central nervous system, such as migraine, cerebral vasospasm, cerebral hemorrhage, trauma and cerebral edema, depression, anxiety, stress, emotional disorders, obsessive-compulsive disorder, panic attacks, psychotic states, aggression, memory or sleep disorders, or cognitive disorders, for example; conditions of the renal system, such as renal vasospasm, necrosis of the renal cortex, nephrogenic diabetes insipidus or diabetic nephropathy; or conditions of the gastric system, such as gastric vasospasm, cirrhosis of the liver, ulcers or the pathology of vomiting, for example nausea, including nausea due to chemotherapy, or travel sickness. The compounds according to the invention can also be used in the treatment of disorders of sexual behavior; in women, the compounds according to the invention can be used to treat primary or secondary dysmenorrhea, premature labor or endometriosis. The compounds according to the invention can also be used in the treatment of cancers, such as small cell lung cancers or breast cancers; hyponatremic encephalopathy; pulmonary syndrome; Ménière's disease; ocular hypertension; glaucoma; cataracts; obesity; type-I and type-II diabetes; atherosclerosis; metabolic syndrome; hyperlipidemia; insulin resistance; or hypertriglyceridemia; in post-operative treatments, in particular after abdominal surgery; autism; hypercortisolemia; hyperaldosteronemia; pheochromocytoma; Cushing's syndrome; preeclampsia; disorders of micturition; or premature ejaculation.

The compounds according to the invention can also be used in the treatment or prevention of any pathology resulting from stress, such as fatigue and its syndromes, ACTH-dependent disorders, cardiac disorders, pain, modifications in gastric emptying, in fecal excretion (colitis, irritable bowel syndrome or Crohn's disease) or in acid secretion, hyperglycemia, immunosuppression, inflammatory processes (rheumatoid arthritis and osteoarthritis), multiple infections, septic shock, cancers, asthma, psoriasis, allergies and various neuropsychiatric disorders, such as anorexia nervosa, bulimia, mood disorders, depression, anxiety, sleep disorders, panic states, phobias, obsession, disorders of pain perception (fibromyalgia), neurodegenerative diseases (Alzheimer's disease, Parkinson's disease or Huntington's disease), substance (alcohol or drug) dependence, withdrawal, hemorrhagic stress, muscle spasms or hypoglycemia. The compounds according to the invention can also be used in the treatment or prevention of chronic stress conditions, such as immunodepression, fertility disorders or dysfunctionings of the hypothalamopituitaryadrenal axis.

The compounds according to the invention can also be used as psychostimulants, resulting in an increase in alertness or emotional reactivity to the surroundings and making adaptation easier.

Finally, the compounds according to the present invention can be used in healing, in analgesia, in anxiolysis, in the prevention of pain, in the prevention of anxiety, depression, schizophrenia, autism or obsessive-compulsive syndrome, in maternal behavior (facilitation of recognition and acceptance of the mother by the child) and social behavior, memory; regulation of food and drink intake, dependence on drugs, withdrawal and sexual motivation; hypertension, hyponatremia, cardiac insufficiency, atherosclerosis, angiogenesis, the proliferation of tumors, Kaposi's sarcoma, to regulate the storage of fat by the adipocyte, to control hyperlipidemia, triglyceridemia and metabolic syndrome.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a solvate or a hydrate of said compound, and at least one pharmaceutically acceptable excipient.

Said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and human beings for the prophylaxis or treatment of the above disorders or diseases.

The appropriate unit administration forms comprise forms by the oral route, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. Use may be made, for the topical application, of the compounds according to the invention in creams, gels, ointments or lotions.

By way of example, a unit administration form of a compound according to the invention in the tablet form can comprise the following components:

| Compound according to the invention | 50.0 mg |
|---|---|
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

Orally, the dose of active principle administered per day can reach from 0.01 to 100 mg/kg, taken all at once or at intervals throughout the day, preferably from 0.02 to 50 mg/kg.

There may be particular cases where higher or lower dosages are appropriate; such dosages do not depart from the scope of the invention. According to the normal practice, the dosage appropriate to each patient is determined by the physician according to the method of administration and the weight and the response of said patient.

The present invention, according to another of its aspects, also relates to a method for the treatment of the pathologies indicated above which comprises the administration, to a patient, of an effective dose of a compound according to the invention or one of its pharmaceutically acceptable salts or its hydrates or solvates.

What is claimed is:
1. A compound corresponding to the formula (I):

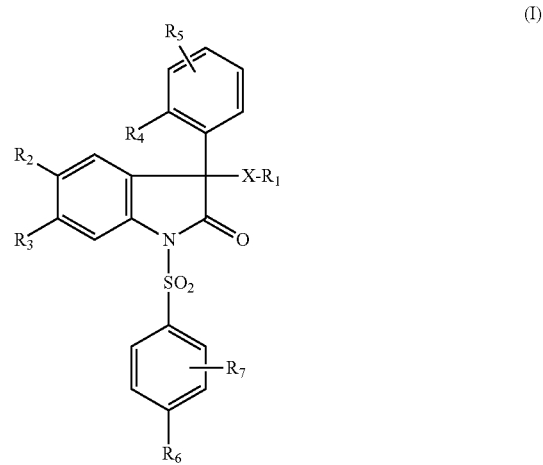

in which:
X represents a divalent ($C_1$-$C_5$)alkylene radical which is unsubstituted or substituted one or more times on a carbon atom by a fluorine atom or by a ($C_1$-$C_3$)alkyl;
$R_1$ represents:
 an —$NR_8R_9$ group;
 a piperidin-4-yl radical or a piperidin-3-yl radical which is unsubstituted or substituted one or more times by a ($C_1$-$C_4$)alkyl or a ($C_3$-$C_5$)cycloalkyl, it being possible for the carbon atoms to be also substituted by one or more fluorine atoms;
$R_2$ represents a halogen atom, an Alk group or an OAlk group;
$R_3$ represents a methoxy;
$R_4$ represents a hydrogen atom, a halogen atom, an Alk group, a hydroxyl or an OAlk group;
$R_5$ represents a hydrogen atom, a halogen atom, an Alk group, a hydroxyl, an OAlk group, a —$CO_2$Alk group or a —$CH_2$OH radical;

R₆ represents a hydrogen atom, an Alk group, a hydroxyl, an OAlk group, a $(C_3\text{-}C_5)$cycloalkyloxy or an —$NR_{10}CONR_{11}R_{12}$ group;

R₇ represents a hydrogen atom, a halogen atom, an Alk group, a hydroxyl or an OAlk group;

or else R₇ is in the 3 position of the phenyl and, together with R₆, represents a trimethylene radical;

R₈ and R₉ each independently represent a hydrogen atom or a $(C_1\text{-}C_4)$alkyl;

or else R₈ and R₉, together with the nitrogen atom to which they are bonded, constitute a saturated or unsaturated 3- to 10-membered heterocyclic radical, said heterocyclic radical being unsubstituted or substituted one or more times by an amino, a dimethylamino, a hydroxyl, an Alk group, a $(C_3\text{-}C_5)$cycloalkyl, an OAlk group or an —$SO_2$Alk radical, it being possible for the carbon atoms to be also substituted by one or more fluorine atoms;

R₁₀ represents a hydrogen atom or a $(C_1\text{-}C_4)$alkyl;

R₁₁ and R₁₂ each independently represent a hydrogen atom or a $(C_1\text{-}C_4)$alkyl;

Alk represents a $(C_1\text{-}C_4)$alkyl which is unsubstituted or substituted one or more times by a fluorine atom;

in the form of the base or of an addition salt with an acid, and also in the form of hydrates or solvates.

2. The compound of formula (I) as claimed in claim 1, in which:

X represents a divalent $(C_1\text{-}C_5)$alkylene radical which is unsubstituted or substituted one or more times on a carbon atom by a fluorine atom or by a $(C_1\text{-}C_3)$alkyl;

R₁ represents:

an —$NR_8R_9$ group;

a piperidin-4-yl radical or a piperidin-3-yl radical which is unsubstituted or substituted by a methyl;

R₂ represents a halogen atom, a methyl or a methoxy;

R₃ represents a methoxy;

R₄ represents a hydrogen atom, a fluorine atom, a methyl or a methoxy;

R₅ represents a hydrogen atom, a halogen atom, a —$CO_2$Alk group or a —$CH_2OH$ radical;

R₆ represents a hydrogen atom, an Alk group, an OAlk group, a hydroxyl, a cyclopentyloxy or an —NHCON(Et)₂ group;

R₇ represents a hydrogen atom, a halogen atom, a methyl, a methoxy or a CF₃ radical;

or else R₇ is in the 3 position of the phenyl and, together with R₆, constitutes a trimethylene radical;

R₈ and R₉ each represent a methyl;

or else R₈ and R₉, together with the nitrogen atom to which they are bonded, constitute a heterocyclic radical chosen from: pyrrolidin-1-yl, piperidin-1-yl, morpholin-4-yl, piperazin-1-yl, 1,4-diazepan-1-yl, 2,5-diazabicyclo[2.2.1]hept-2-yl, 3,8-diazabicyclo[3.2.1]oct-3-yl, 2,5-diazabicyclo[2.2.2]oct-2-yl, 1,4-diazabicyclo[3.2.1]oct-4-yl, hexahydropyrrolo[1,2-a]pyrazin-2(1H)-yl or octahydro-2H-pyrido-[1,2-a]pyrazin-2-yl, said heterocyclic radical being unsubstituted or substituted once or twice by a fluorine atom, an amino, a dimethylamino, a hydroxyl, an Alk group, a cyclobutyl or an —$SO_2$Me radical;

Alk represents a $(C_1\text{-}C_4)$alkyl which is unsubstituted or substituted one or more times by a fluorine atom;

in the form of the base or of an addition salt with an acid, and also in the hydrate or solvate form.

3. The compound of formula (I) as claimed in claim 1, in which:

X represents a divalent $(C_1\text{-}C_5)$alkylene radical;

R₁ represents:

a dimethylamino, a 3-aminopyrrolidin-1-yl, a 3-dimethylaminopyrrolidin-1-yl, a piperidin-1-yl, a 3,3-difluoropiperidin-1-yl, a 4,4-difluoropiperidin-1-yl, a 4-hydroxypiperidin-1-yl, a morpholin-4-yl, a 4-methylpiperazin-1-yl, a piperazin-1-yl, a 4-ethylpiperazin-1-yl, a 1,4-diazepan-1-yl, a 2,5-diaza-bicyclo[2.2.1]hept-2-yl, a 4-isopropylpiperazin-1-yl, a 3-methylpiperazin-1-yl, a 3,4-dimethylpiperazin-1-yl, a 4-cyclobutylpiperazin-1-yl, a 5-methyl-2,5-diazabicyclo[2.2.1]hept-2-yl, a 3,5-dimethylpiperazin-1-yl, a 4-methyl-1,4-diazepan-1-yl, an 8-methyl-3,8-diazabicyclo[3.2.1]oct-3-yl, a 2,6-dimethylpiperazin-1-yl, a 3-isopropylpiperazin-1-yl, a 2,2-dimethylpiperazin-1-yl, a 2,5-diazabicyclo[2.2.2]oct-2-yl, a 2,5-dimethylpiperazin-1-yl, a 2,2,4-trimethylpiperazin-1-yl, a 1,4-diazabicyclo[3.2.1]oct-4-yl, a 2-isopropylpiperazin-1-yl, a hexahydropyrrolo[1,2-a]pyrazin-2(1H)-yl, an octahydro-2H-pyrido-[1,2-a]pyrazin-2-yl, a 3-trifluoromethylpiperazin-1-yl, a 4-methylsulfonyl-piperazin-1-yl or a 4-(dimethylamino)piperidin-1-yl;

a piperidin-4-yl, a 1-methylpiperidin-4-yl, a 1-methylpiperidin-3-yl or a piperidin-3-yl;

R₂ represents a chlorine, fluorine or bromine atom, a methyl or a methoxy;

R₃ represents a methoxy;

R₄ represents a hydrogen atom, a fluorine atom, a methyl or a methoxy;

R₅ represents a hydrogen atom, a 3-chloro, a 5-fluoro, a 6-fluoro, a 5-methoxycarbonyl or a 5-hydroxymethyl;

R₆ represents a hydrogen atom, a methyl, an isopropyl, a methoxy, an ethoxy, an isopropoxy, a butyloxy, a tert-butyloxy, a cyclopentyloxy, a 1,1,2,2-tetrafluoroethyloxy, a 2,2-diethylureido, a difluoromethoxy, a trifluoromethoxy or a hydroxyl;

R₇ represents a hydrogen atom, a 3-methyl, a 2-methoxy, a 3-methoxy, a 3-fluoro, a 3-chloro or a 3-CF₃;

or else R₇ is in the 3 position of the phenyl and, together with R₆, constitutes a trimethylene radical;

in the form of the base or of an addition salt with an acid, and also in the hydrate or solvate form.

4. The compound as claimed in claim 1 of formula (I), in which:

X represents a divalent trimethylene or pentamethylene radical;

R₁ represents:

a dimethylamino, a 3-aminopyrrolidin-1-yl, a piperidin-1-yl, a 4,4-difluoro-piperidin-1-yl, a 4-hydroxypiperidin-1-yl, a 4-(dimethylamino)piperidin-1-yl, a morpholin-4-yl, a 4-methylpiperazin-1-yl, a piperazin-1-yl, a 3,4-dimethylpiperazin-1-yl, a 5-methyl-2,5-diazabicyclo[2.2.1]hept-2-yl, a 4-methyl-1,4-diazepan-1-yl, an 8-methyl-3,8-diazabicyclo[3.2.1]oct-3-yl or a 1,4-diazabicyclo[3.2.1]oct-4-yl;

a piperidin-4-yl;

R₂ represents a chlorine, fluorine or bromine atom or a methyl;

R₃ represents a methoxy;

R₄ represents a hydrogen atom or a fluorine atom;

R₅ represents a hydrogen atom, a 5-methoxycarbonyl or a 5-hydroxymethyl;

R₆ represents a hydrogen atom, a methyl, a methoxy, an isopropoxy, an ethoxy, a butyloxy, a 1,1,2,2-tetrafluoroethyloxy, a 2,2-diethylureido, a difluoromethoxy, a trifluoromethoxy or a hydroxyl;

R₇ represents a hydrogen atom, a 2-methoxy, a 3-methoxy, a 3-methyl or a 3-fluoro;

in the form of the base or of an addition salt with an acid, and also in the hydrate or solvate form.

5. The compound as claimed in claim 1 of formula (I), chosen from:

5-chloro-1-[(2,4-dimethoxyphenyl)sulfonyl]-3-(2-fluorophenyl)-6-methoxy-3-(3-(piperidin-4-yl)propyl)-1,3-dihydro-2H-indol-2-one, dextrorotatory isomer;

5-chloro-1-[(2,4-dimethoxyphenyl)sulfonyl]-3-(2-fluorophenyl)-6-methoxy-3-(3-(piperidin-4-yl)propyl)-1,3-dihydro-2H-indol-2-one, levorotatory isomer;

5-chloro-3-[3-(dimethylamino)propyl]-3-(2-fluorophenyl)-1-[(4-isopropoxy-phenyl)sulfonyl]-6-methoxy-1,3-dihydro-2H-indol-2-one, dextrorotatory isomer;

3-{3-[(3R)-3-aminopyrrolidin-1-yl]propyl}-5-chloro-3-(2-fluorophenyl)-1-[(4-isopropoxyphenyl)sulfonyl]-6-methoxy-1,3-dihydro-2H-indol-2-one, dextrorotatory isomer;

3-{3-[(3S)-3-aminopyrrolidin-1-yl]propyl}-5-chloro-3-(2-fluorophenyl)-1-[(4-isopropoxyphenyl)sulfonyl]-6-methoxy-1,3-dihydro-2H-indol-2-one, dextrorotatory isomer;

3-{3-[(3R)-3-aminopyrrolidin-1-yl]propyl}-5-chloro-1-[(4-ethoxy-3-methoxyphenyl)sulfonyl]-3-(2-fluorophenyl)-6-methoxy-1,3-dihydro-2H-indol-2-one, dextrorotatory isomer;

3-{3-[(3S)-3-aminopyrrolidin-1-yl]propyl}-5-chloro-1-[(4-ethoxy-3-methoxyphenyl)sulfonyl]-3-(2-fluorophenyl)-6-methoxy-1,3-dihydro-2H-indol-2-one, dextrorotatory isomer;

5-chloro-1-[(2,4-dimethoxyphenyl)sulfonyl]-3-(2-fluorophenyl)-6-methoxy-3-(3-(piperidin-1-yl)propyl)-1,3-dihydro-2H-indol-2-one, dextrorotatory isomer;

5-chloro-3-[3-(4,4-difluoropiperidin-1-yl)propyl]-1-[(4-ethoxy-3-methoxy-phenyl)sulfonyl]-3-(2-fluorophenyl)-6-methoxy-1,3-dihydro-2H-indol-2-one, dextrorotatory isomer;

5-chloro-1-[(4-ethoxy-3-methoxyphenyl)sulfonyl]-3-(2-fluorophenyl)-3-[3-(4-hydroxypiperidin-1-yl)propyl]-6-methoxy-1,3-dihydro-2H-indol-2-one, dextrorotatory isomer;

5-chloro-1-[(4-ethoxy-3-methoxyphenyl)sulfonyl]-3-(2-fluorophenyl)-6-methoxy-3-(3-(morpholin-4-yl)propyl)-1,3-dihydro-2H-indol-2-one, dextrorotatory isomer;

5-chloro-1-[(2,4-dimethoxyphenyl)sulfonyl]-3-(2-fluorophenyl)-6-methoxy-3-[3-(4-methylpiperazin-1-yl)propyl]-1,3-dihydro-2H-indol-2-one, dextrorotatory isomer;

5-chloro-3-(2-fluorophenyl)-1-[(4-isopropoxyphenyl)sulfonyl]-6-methoxy-3-[3-(4-methylpiperazin-1-yl)propyl]-1,3-dihydro-2H-indol-2-one, dextrorotatory isomer;

5-chloro-1-[(4-ethoxy-3-methoxyphenyl)sulfonyl]-3-(2-fluorophenyl)-6-methoxy-3-[3-(4-methylpiperazin-1-yl)propyl]-1,3-dihydro-2H-indol-2-one, dextrorotatory isomer;

5-chloro-1-[(3,4-dimethoxyphenyl)sulfonyl]-3-(2-fluorophenyl)-6-methoxy-3-[3-(4-methylpiperazin-1-yl)propyl]-1,3-dihydro-2H-indol-2-one, dextrorotatory isomer;

5-chloro-1-[(2,4-dimethoxyphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-3-(2-fluorophenyl)-1-[(4-isopropoxyphenyl)sulfonyl]-6-methoxy-3-(3-(piperazin-1-yl)propyl)-1,3-dihydro-2H-indol-2-one, dextrorotatory isomer;

5-chloro-1-[(4-ethoxy-3-methoxyphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-1-[(3,4-dimethoxyphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-1-[(3,4-dimethylphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-3-(2-fluorophenyl)-6-methoxy-1-[(4-methoxy-3-methylphenyl)-sulfonyl]-3-(3-(piperazin-1-yl)propyl)-1,3-dihydro-2H-indol-2-one;

5-chloro-1-[(4-ethoxyphenyl)sulfonyl]-3-(2-fluorophenyl)-6-methoxy-3-(3-(piperazin-1-yl)propyl)-1,3-dihydro-2H-indol-2-one, dextrorotatory isomer;

5-chloro-1-[(4-ethoxy-3-methylphenyl)sulfonyl]-3-(2-fluorophenyl)-6-methoxy-3-(3-(piperazin-1-yl)propyl)-1,3-dihydro-2H-indol-2-one;

5-chloro-1-{[4-(difluoromethoxy)phenyl]sulfonyl}-3-(2-fluorophenyl)-6-methoxy-3-(3-(piperazin-1-yl)propyl)-1,3-dihydro-2H-indol-2-one, dextrorotatory isomer;

5-chloro-3-(2-fluorophenyl)-6-methoxy-3-(3-(piperazin-1-yl)propyl)-1-{[4-(trifluoromethoxy)phenyl]sulfonyl}-1,3-dihydro-2H-indol-2-one, dextrorotatory isomer;

5-chloro-3-(2-fluorophenyl)-6-methoxy-1-(phenylsulfonyl)-3-(3-(piperazin-1-yl)propyl)-1,3-dihydro-2H-indol-2-one, dextrorotatory isomer;

5-chloro-1-(2,3-dihydro-1H-inden-5-ylsulfonyl)-3-(2-fluorophenyl)-6-methoxy-3-(3-(piperazin-1-yl)propyl)-1,3-dihydro-2H-indol-2-one, dextrorotatory isomer;

5-chloro-1-{[3-fluoro-4-(1-methylethoxy)phenyl]sulfonyl}-3-(2-fluorophenyl)-6-methoxy-3-[3-(4-methylpiperazin-1-yl)propyl]-1,3-dihydro-2H-indol-2-one, dextrorotatory isomer;

5-chloro-3-(2-fluorophenyl)-6-methoxy-3-[3-(4-methylpiperazin-1-yl)propyl]-1-{[4-(1,1,2,2-tetrafluoroethoxy)phenyl]sulfonyl}-1,3-dihydro-2H-indol-2-one, dextrorotatory isomer;

3-(2-fluorophenyl)-6-methoxy-5-methyl-1-{[4-(1-methylethoxy)phenyl]-sulfonyl}-3-[3-(4-methylpiperazin-1-yl)propyl]-1,3-dihydro-2H-indol-2-one, dextrorotatory isomer;

5-fluoro-3-(2-fluorophenyl)-6-methoxy-1-{[4-(1-methylethoxy)phenyl]-sulfonyl}-3-[3-(4-methylpiperazin-1-yl)propyl]-1,3-dihydro-2H-indol-2-one, dextrorotatory isomer;

5-bromo-3-(2-fluorophenyl)-6-methoxy-1-{[4-(1-methylethoxy)phenyl]-sulfonyl}-3-[3-(4-methylpiperazin-1-yl)propyl]-1,3-dihydro-2H-indol-2-one, dextrorotatory isomer;

3-[4-({3-[3-(dimethylamino)propyl]-3-(2-fluorophenyl)-6-methoxy-5-methyl-2-oxo-2,3-dihydro-1H-indol-1-yl}sulfonyl)-2-fluorophenyl]-1,1-diethylurea, dextrorotatory isomer;

3-[4-({3-[3-(dimethylamino)propyl]-3-(2-fluorophenyl)-6-methoxy-5-methyl-2-oxo-2,3-dihydro-1H-indol-1-yl}sulfonyl)-2-methylphenyl]-1,1-diethylurea, dextrorotatory isomer;

5-chloro-3-(2-fluorophenyl)-6-methoxy-3-[3-(8-methyl-3,8-diazabicyclo[3.2.1]oct-3-yl)propyl]-1-{[4-(1-methylethoxy)phenyl]sulfonyl}-1,3-dihydro-2H-indol-2-one, dextrorotatory isomer;

5-chloro-3-(2-fluorophenyl)-6-methoxy-3-[3-(5-methyl-2,5-diazabicyclo[2.2.1]hept-2-yl)propyl]-1-{[4-(1-methylethoxy)phenyl]sulfonyl}-1,3-dihydro-2H-indol-2-one, dextrorotatory isomer;

5-chloro-3-(2-fluorophenyl)-1-[(4-hydroxyphenyl)sulfonyl]-6-methoxy-3-[3-(4-methylpiperazin-1-yl)propyl]-1,3-dihydro-2H-indol-2-one, dextrorotatory isomer;

5-chloro-3-(2-fluorophenyl)-6-methoxy-3-[3-(4-methyl-1,4-diazepan-1-yl)-propyl]-1-{[4-(1-methylethoxy)phenyl]sulfonyl}-1,3-dihydro-2H-indol-2-one, dextrorotatory isomer;

5-chloro-3-(2-fluorophenyl)-6-methoxy-1-{[4-(1-methylethoxy)phenyl]-sulfonyl}-3-(5-(piperidin-1-yl)pentyl)-1,3-dihydro-2H-indol-2-one, dextrorotatory isomer;

5-chloro-3-[5-(dimethylamino)pentyl]-3-(2-fluorophenyl)-6-methoxy-1-{[4-(1-methylethoxy)phenyl]sulfonyl}-1,3-dihydro-2H-indol-2-one, dextrorotatory isomer;

5-chloro-3-{3-[(3S)-3,4-dimethylpiperazin-1-yl]propyl}-3-(2-fluorophenyl)-6-methoxy-1-{[4-(1-methylethoxy)phenyl]sulfonyl}-1,3-dihydro-2H-indol-2-one, dextrorotatory isomer;

5-chloro-6-methoxy-1-{[4-(1-methylethoxy)phenyl]sulfonyl}-3-[3-(4-methylpiperazin-1-yl)propyl]-3-phenyl-1,3-dihydro-2H-indol-2-one, dextrorotatory isomer;

5-chloro-3-{3-[(5S)-1,4-diazabicyclo[3.2.1]oct-4-yl]propyl}-3-(2-fluorophenyl)-6-methoxy-1-{[4-(1-methylethoxy)phenyl]sulfonyl}-1,3-dihydro-2H-indol-2-one, dextrorotatory isomer;

1-[(4-butoxyphenyl)sulfonyl]-5-chloro-3-(2-fluorophenyl)-6-methoxy-3-[3-(4-methylpiperazin-1-yl)propyl]-1,3-dihydro-2H-indol-2-one, dextrorotatory isomer;

5-chloro-3-[3-[4-(dimethylamino)piperidin-1-yl]propyl]-3-(2-fluorophenyl)-1-[(4-isopropoxyphenyl)sulfonyl]-6-methoxy-1,3-dihydro-2H-indol-2-one;

1-[(3-fluoro-4-isopropoxyphenyl)sulfonyl]-3-(2-fluorophenyl)-5,6-dimethoxy-3-[3-(4-methylpiperazin-1-yl)propyl]-1,3-dihydro-2H-indol-2-one;

5-fluoro-1-[(3-fluoro-4-isopropoxyphenyl)sulfonyl]-3-(2-fluorophenyl)-6-methoxy-3-[3-(4-methylpiperazin-1-yl)propyl]-1,3-dihydro-2H-indol-2-one;

3-(2-fluorophenyl)-5,6-dimethoxy-1-[(4-methoxy-3-methylphenyl)sulfonyl]-3-[3-(4-methylpiperazin-1-yl)propyl]-1,3-dihydro-2H-indol-2-one;

methyl 3-[5-chloro-1-[(4-isopropoxyphenyl)sulfonyl]-6-methoxy-3-[3-(4-methylpiperazin-1-yl)propyl]-2-oxo-2,3-dihydro-1H-indol-3-yl]-4-fluoro-benzoate;

5-chloro-3-[2-fluoro-5-(hydroxymethyl)phenyl]-1-[(4-isopropoxyphenyl)-sulfonyl]-6-methoxy-3-[3-(4-methylpiperazin-1-yl)propyl]-1,3-dihydro-2H-indol-2-one;

in the form of the base or of addition salts with acids, and also in the hydrate or solvate form.

6. A process for the preparation of the compound of formula (I) as claimed in claim 1, wherein:
a compound of formula:

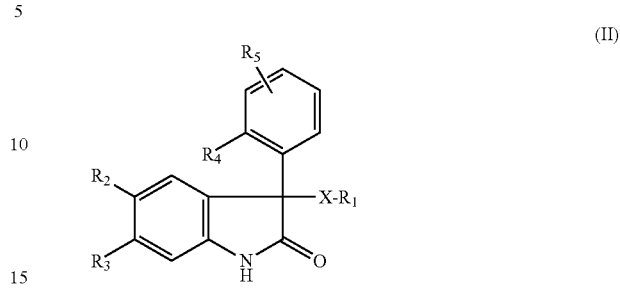

(II)

in which X, $R_1$, $R_2$, $R_3$, $R_4$ and $R_5$ are as defined for a compound of formula (I) in claim 1, is reacted, in the presence of a base, with a sulfonyl halide of formula:

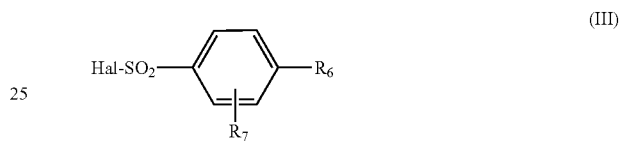

(III)

in which $R_6$ and $R_7$ are as defined for a compound of formula (I) in claim 1 and Hal represents a halogen atom.

7. A process for the preparation of the compound of formula (I) as claimed in claim 1, wherein:
a compound of formula:

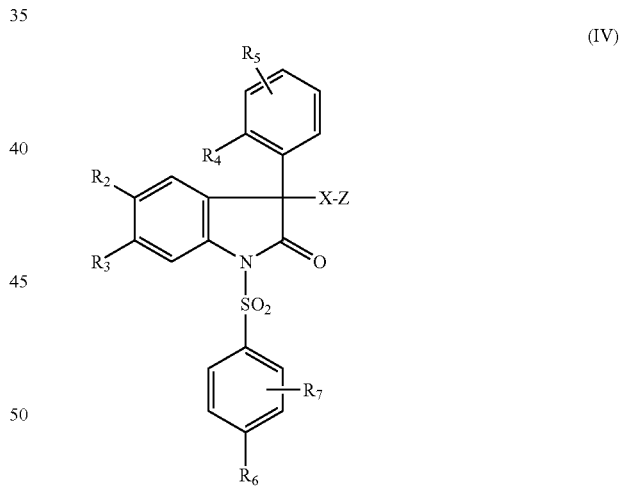

(IV)

in which X, $R_2$, $R_3$, $R_4$, $R_5$, $R_6$ and $R_7$ are as defined for a compound of formula (I) in claim 1 and Z represents a leaving group chosen from a halogen atom or a methanesulfonate or p-toluenesulfonate group, is reacted with a compound of formula:

$R_1$—H     (V)

in which $R_1$ is as defined for a compound of formula (I) in claim 1.

8. A pharmaceutical composition comprising a compound of formula (I) as claimed in claim 1, or a pharmaceutically acceptable salt, hydrate or solvate of this compound, and at least one pharmaceutically acceptable excipient.

* * * * *